(12) United States Patent
Young et al.

(10) Patent No.: US 6,419,636 B1
(45) Date of Patent: Jul. 16, 2002

(54) SYSTEM FOR THERMOMETRY-BASED BREAST ASSESSMENT INCLUDING CANCER RISK

(76) Inventors: David Ernest Young, Bowler's Piece, 16 Couching Street, Watlington, Oxfordshire OX49 5QQ; Colin Alfred Young, 20 North Quay, Abingdon Marina, Abingdon, Oxfordshire, OX14 5RY; Kevin Jenkins, 1 The Croft, Marsh Baldon, Oxfordshire OX44 9LN, all of (GB)

(*) Notice: Subject to any disclaimer, the term of this patent is extended or adjusted under 35 U.S.C. 154(b) by 28 days.

(21) Appl. No.: 09/710,603

(22) Filed: Nov. 9, 2000

Related U.S. Application Data

(63) Continuation-in-part of application No. 09/385,387, filed on Aug. 30, 1999, now Pat. No. 6,179,786.
(60) Provisional application No. 60/102,882, filed on Oct. 2, 1998.

(51) Int. Cl.[7] .............................. A61B 5/00; A61B 5/04
(52) U.S. Cl. ....................... 600/549; 600/388; 600/386; 600/382; 600/372
(58) Field of Search .................................. 600/549, 388, 600/386, 389, 390, 393, 382, 372, 306, 300, 551

(56) References Cited

U.S. PATENT DOCUMENTS

| | | |
|---|---|---|
| 3,830,224 A | 8/1974 | Vanzetti et al. |
| 3,847,139 A | 11/1974 | Flam |
| 3,960,138 A | 6/1976 | Doss et al. |
| 4,190,058 A | 2/1980 | Sagi |
| 4,524,778 A | 6/1985 | Brown, Jr. et al. |
| RE32,000 E | 10/1985 | Sagi |
| 4,624,264 A | 11/1986 | Sagi |
| 4,651,749 A | 3/1987 | Sagi |
| 5,301,681 A | 4/1994 | DeBan et al. |
| 5,813,404 A | 9/1998 | Devlin et al. |
| 5,830,159 A | 11/1998 | Netta |
| 5,941,832 A | 8/1999 | Tumey et al. |
| 5,999,843 A | 12/1999 | Anbar |
| 6,077,228 A | 6/2000 | Schonberger |
| 6,086,247 A | 7/2000 | von Hollen |

FOREIGN PATENT DOCUMENTS

| | | |
|---|---|---|
| EP | PCT/US90/02203 | 11/1990 |
| GB | 1 492 803 | 11/1977 |
| GB | 2 203 250 | 10/1988 |

OTHER PUBLICATIONS

Simpson, Griffiths et al., "The luteal heat cycle of the breast in health", 27 Breast Cancer Research and treatment, 239–45 (1993).

Sir James Young Simpson, Memorial lecture 1995 "Breast Cancer Prevention (a pathologist's approach)", J.R. Coll. Surg. Edinb., 41 (Jun. 1996).

Simpson, et al., "The luteal heat cycle of the breast in disease", Breast Cancer Research and Treatment (1995).

Simpson, et al., "A clinical test for brease pre–cancer", Journal of Chronobiological Research in Medicine 1, N.1 (1995).

*Primary Examiner*—Kevin Shaver
*Assistant Examiner*—Navin Natnithithadha
(74) *Attorney, Agent, or Firm*—Marshall, Gerstein & Borun.

(57) ABSTRACT

A system for thermometry-based breast assessment has an analog electronic sensor and an adjustable mechanical harness. In order to sample breast surface temperature, and to collect, store, and display data relating thereto, the system has remote data-logging control. The system allows breast temperatures to be measured, with great accuracy and reliability, for selected periods for up to seven days at any desired rational sampling rate. Collected breast surface temperature data may then be uploaded into a computer for elaboration using a dedicated computer program. Breast surface temperatures may be measured at a specific point during the menstrual cycle, determined by progesterone levels in the urine when the system is used to determine the risk of breast cancer occurring later in women who do not currently have the disease or it may be used at other times for other purposes.

12 Claims, 28 Drawing Sheets

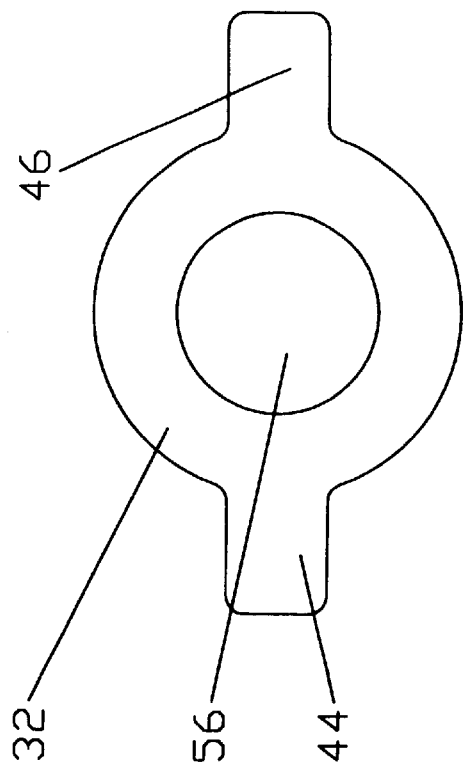
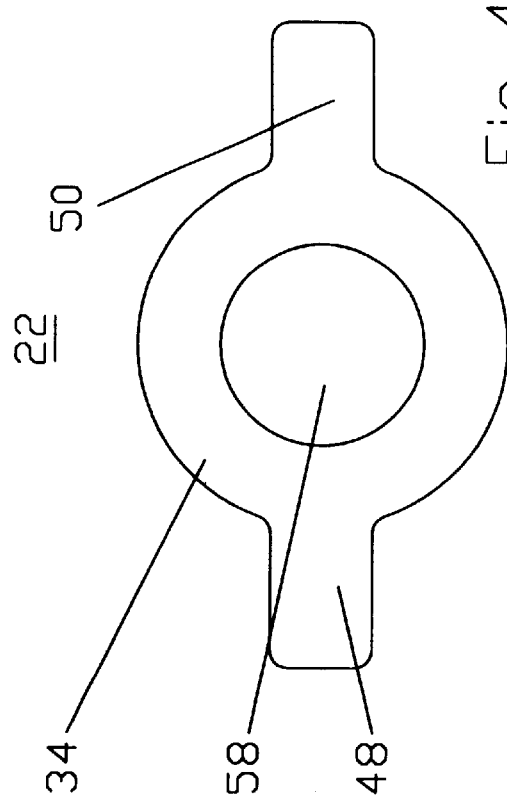
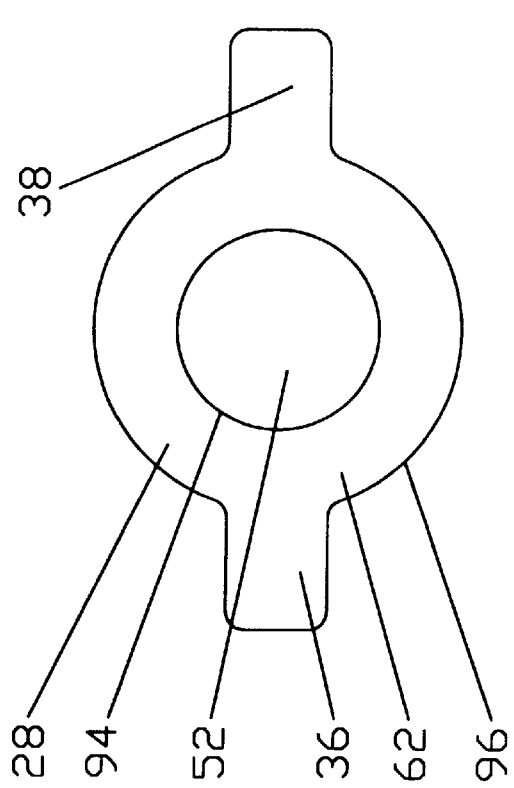
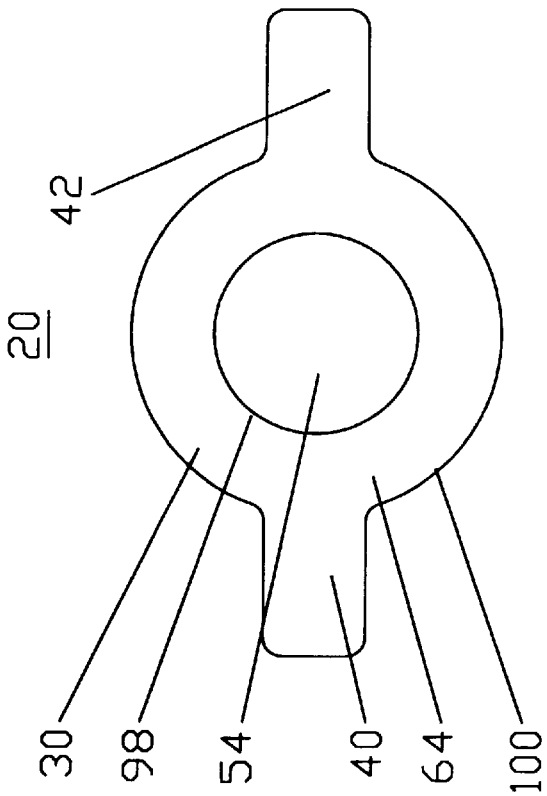
Fig 4

SYSTEM FOR THERMOMETRY-BASED BREAST ASSESSMENT INCLUDING CANCER RISK

REFERENCE TO RELATED APPLICATIONS

This application is entitled to the benefit of the filing date of U.S. patent application Ser. No. 09/385,387, filed Aug. 30, 1999, now issued U.S. Pat. No. 6,179,786, and Provisional Application No. 60/102,882, filed Oct. 2, 1998 with respect to all subject matter common to all applications.

FIELD OF THE INVENTION

The present invention is in the field of biotechnology and specifically relates to the field of breast assessment and breast cancer screening in women.

BACKGROUND TO THE PRESENT INVENTION—THE RELATED ART

For well over twenty years, thermometric assessment of the human female breast surface has been under investigation as a tool in the armamentarium of those concerned with the detection and treatment of breast cancer.

GB 1,490,803 (expired) and U.S. Pat. No. 4,055,166 (expired), both granted to Simpson and Green and of substantially identical content, describe a garment which is a brassiere upon and within which is mounted a plurality of sensors for the purpose of measuring breast temperature over the menstrual cyde. They referred to a menstrual cycle of breast heat amounting to a variation in surface temperature of about 1° C. which is maximal about three days before the onset of menstruation. In the preamble, it is made clear that the intention is to detect the presence of actual cancers based on the observation that areas adjacent to a cancerous growth may be "slightly warmer (say 1 or 2° F.) than unaffected areas of the other breast" and that comparison of the 24 hour temperature variation (circadian variation) between normal and cancerous breasts have shown clear differences in time structure.

In a subsequently abandoned application publication number GB 2,203,250 A, Simpson again teaches a garment in the form of a brassiere with a miniaturized electronic heat measuring device which has a number of cup temperature sensors. In a further embodiment there is disclosed another brassiere "having a single sensor net of high thermal conductivity wire centered on the nipple and extending for a few centimeters around each nipple".

In these disclosures Simpson and his colleagues make an important structural distinction between their brassiere device and the earlier breast surface measurements which had been made in hospital environments with sensors fixed on the skin. They taught the provision of a garment which would allow temperature measurements to be recorded over relatively long periods while the subject lives normally. They provide "apparatus for measuring surface temperatures at points in the region of the human body, including a garment having a plurality of temperature sensors located therein at spaced apart positions, and means for so storing signals representing output signals from the sensors that the relationship of each signal time of occurrence can be retrieved".

In particular, they indicate a preference for the storage means to be mounted on the garment. According to claim 1 of U.S. Pat. No. 4,055,166, the garment and the means for storing signals are integral. In Claim 1 of GB 1,490,803, the apparatus includes a garment and Claim 4, as well as other various other dependent Claims, describes a brassiere which includes sampling and storage means being integral with the brassiere.

Simpson and Green make it clear that, in relation to measurements of temperature on the breasts, the garment may be a brassiere. They teach a brassiere for measuring surface temperatures of the breasts at predetermined points, including a plurality of temperature sensors positioned in each cup of the brassiere, the sampling and storage means being integral with the brassiere.

Their underlying contention is that "The circadian rhythm of breast temperature is regarded as a normal feature of the mammary tissue differentiation—a response possibly of a target organ to tides of hormones in the circulation (e.g., 24-h variations in prolactin; menstrual variations in oestrogen). Consequently alterations of the circadian rhythm characteristics occur in breast pathology of which cancer is one example. In this situation the rhythm is sometimes absent and often of altered level and phase. It follows that monitoring breast temperature rhythm over daily and perhaps monthly intervals will be valuable in detection and characterization of disease, e.g. cancer." From this, and other statements in the specification, it is clear that these authors did not contemplate the application of their invention in the assessment of the future risk of developing cancer and that it was limited to detection of and characterizations of actual lesions.

The Simpson and Green patents teach a brassiere fitted with temperature sensors positioned at points where tumors have been shown to occur most frequently—at the one, two and three o'clock positions, over the nipple, and at the nine o'clock position on the left breast, and on the right breast there is a similar disposition of sensors over the upper outer quadrant, that is at nine, ten and eleven o'clock positions with a sensor over the nipple and one at the three o'clock position. They do contemplate different positioning of the sensors and that a different number may be deployed.

What is quite clear, however, is that their device, as described, is a garment fitted with temperature sensors and having means for storing signals from the sensors included with or integral with the garment. It is also quite clear from the detailed descriptions and claims that, when the apparatus is to be used on the human breast, the garment is to be a brassiere. They also clearly describe, in Claim 6 of each patent, the use of a heat shield to prevent outward heat flow through the sensor.

Simpson has since suggested that the device, which is the subject of the test described in the two patents, is subject to 'noise' and that this is due to other vasomotor phenomena. He has suggested that "The problem with the method is not the signal, but the noise from these sources." *Sir James Young Simpson Memorial Lecture, J. R. Coll. Surg. Edinb.*, 41, June 1996. He goes on to suggest that future developments could include Doppler ultrasonography applied to the internal mammary artery and volumetric analysis of the breast and its component tissue using magnetic resonance imaging.

In the source quoted above, Simpson makes it clear that his developments are nowadays directed at trying to predict, from temperature measurements, which breasts may develop cancer later.

Although Simpson and Green appear possibly to have been the first workers to make serious attempts at detecting breast cancer by observing breast surface temperatures, theirs is not the only work. Detectors for actual cancer lesions based on breast surface temperature are still being developed and this is somewhat surprising since most authorities believe that tumors large enough to find by this method are already likely to have progressed so far as to carry with them fatal consequences.

One example is BreastAssure™ made in the USA by HumaScan Inc of Cranford, N.J. The makers claim that this device is the subject of two US patents which expired on May $22^{nd}$ 1998 and a Canadian patent which expired on Aug. $24^{th}$ 1999; these are all believed to be to Z. L. Sagi. Financial literature on the company states the product " . . . consists of a pair of mirror-image, non-invasive, lightweight, disposable soft pads, each of which has three wafer-thin segments containing columns of heat sensitive chemical sensor dots that change color from blue to pink reflecting an 8.5° temperature range from 90° to 98.5° F. When placed over a woman's breasts, inside her brassiere for a period of 15 minutes, the device registers skin temperature variations due to heat conducted from within the breast tissue to the surface of the skin. By comparing the mirror-image temperature differences between the two breasts registered by the device, the physician can objectively quantify if there is abnormal unilateral breast thermal activity, which is considered significant if there is a 2° F. or more temperature difference between each breast in the same mirror-image location. Based on clinical studies at major medical centers, the threshold tumor size that resulted in significant skin temperature differences detectable with the device was as small as 5 mm in size." It may be worth noting that, according to some authorities, cancers of this size may well have already metastasized. Other experts to whom we have spoken doubt whether 15 minutes is an adequate time for any device placed on or over the breasts to equilibrate with breast temperature on a consistently reliable basis.

This manufacturer claims that, according to industry sources, the majority of breast tumors are, on average, at least 15 mm or larger before they are palpable by most experienced clinicians. Literature which we have seen suggests that 15–20 mm is the range in which most become tumors become palpable.

We subsequently obtained copies of a series of patents to Sagi, namely U.S. Pat. No. 4,190,058 and U.S. Pat. No. Re. 32000; U.S. Pat. No. 4,624,264 and U.S. Pat. No. 4,651,749. Generally these describe patches intended to aid in early detection of breast cancer based on thermography. The patches are substantially circular and comprise radially arranged strips of liquid crystal temperature indicators deposited upon a plurality of segments made of aluminum foil. No means are provided for measurement or display of actual temperatures and the patches are examined for areas of color change. The patches must be used with a brassiere. It is clear that the information which such a device could provide would be very limited and would, in addition, need a skilled physician in attendance to interpret the patches upon removal.

The solid metallic foil of these patches, especially when mounted on a support surface, is unlikely to conform reliably to the concavo-convex three-dimensional architecture of the human breasts and, as hereinafter described in relation to the Simpson device, this would result in non-contact regions. In the case of the Sagi device such an eventuality would lead to incorrect thermographic patterns and misinterpretation. In addition the device requires to be supplied in a multiplicity of sizes to accommodate the wide variation in breast sizes.

Another participant in this field is Biofield Inc of Roswell, Ga., USA, with its ALEXA™ 1000 system. According to material released by the company onto the Internet, this employs single-use sensors and a measurement device to analyze changes in cellular electrical charge distributions associated with the development of epithelial cancers such as breast cancer. Sensors are arranged on the skin surface in and around the quadrant of the breast where a suspicious lesion has been identified and in corresponding locations on the asymptomatic breast. Sensor readings are measured and analyzed using a pre-programmed algorithm. The technology is claimed to be based on the observation that epithelial cancers are characterized by uncontrolled recurrent cell proliferation of rapid cell division. As these cells divide, an electrical charge is released. This results in a disruption, or depolarization, of the charge distribution found in normal epithelial tissue. Moreover, the depolarization appears to be progressive as cell transformation and carcinogenesis occur. It is claimed that this depolarization is measurable at the skin surface in the form of electrophysiological differentials. The final output is a single numerical and objective value, from one to thirty. The result of this test is claimed to provide an indication of the proliferation level, which is related to the probability as to whether a lesion is malignant or benign. The manufacturer claims that a task force sponsored by the European School of Oncology has reported on the measurement of electropotentials from the breast as a possible method of detecting breast cancer. This report summarizes the background and early results and suggest that this technique may have a role in the diagnosis of both palpable and non-palpable breast lesions. U.S. Pat. Nos. 5,427,098; 5,560,357; 5,415,164; 5,217,014; 5,320,101 and 5,099,844 all appear to relate to this technology. We were unable to verify these claims from enquiries made with the European Institute of Oncology, which was the initial assessment center for the original embodiment of the instant invention.

Lifeline BioTechnologies Inc, another US company, has two products which are claimed to increase the chance of finding potential breast cancers at an early stage. The KELLY MONITOR is a detection aid for early breast cancer apparently intended for use as a non-invasive complement to mammography. It consists of sensors and a small portable data storage unit, worn for up to forty-eight hours in order to capture temperature patterns which are stored for later analysis. The device dynamically monitors the physiologic activity of the breast by means of circadian rhythm analysis. This monitor uses a sixteen sensor array: seven for each breast, one for the sternum, and one to measure ambient temperature and, like the Simpson and Green disclosure, calls for placement determined by occurrence data for breast cancer. This product uses a proprietary template for identical placement on each breast. The manufacturer's literature claims to use sensors which are considered "interchangeable", eliminating the need for insulation, adjustable resistors and continued calibration. This commercial claim appears to be directed in a negative manner at the Chronobra™, a device based on Simpson and Green's patents which does require the use of calibration and trimming resistors. It is not clear whether this product is the subject of either an issued patent or a patent application.

Unlike the other devices and products hereinbefore described, the FIRST WARNING™ product is claimed to identify women who will eventually develop breast cancer and be a 'Risk-Marker'. The literature indicates that, during the test, a custom-designed breast temperature sensor is integrated into a cup insert for use with the patient's brassiere, and she will be directed to place the sensors directly within her brassiere and thus on her breast. The patient would be required to wear the device for ninety minutes each night. The sensor is intended to measure surface temperature over the breast area for each breast throughout this period. The inserts are apparently presented in several sizes to fit the wide variation in breast sizes in the female population. According to the literature, each sensor will detect the unique temperature patterns of the breast. The sensors are described as connected to a miniature storage device which is worn concealed under the clothing. The literature indicates that, at the conclusion of the test, the device is plugged into a data storage unit which is small enough to be placed on a bedside table. The data are transferred to the base and the portable unit is recharged. An additional requirement described is for a sample of saliva to be taken on a daily basis. The saliva is placed in a small vial and stored in a refrigerator in a special calendar/date related container until the test concludes. The entire test lasts for thirty days. The results are then analyzed using proprietary techniques to assess the risk factor for the patient. The company claims that traditional statistical techniques are not accurate enough in their discrimination of the data. The ultimate result is an indication of high or low risk. The product is believed to be the subject of a U.S. patent application.

The practicality of this test seems to be questionable at least. It has to be done over thirty days and thus requires an enormous level of compliance in today's fast-moving world where many women do not have well ordered lives which allow them to be constantly at home. This test also has to be done for ninety minutes each night, followed by a procedure to recharge the monitor; it is surely rather likely that the subject would fall asleep. The most limiting factor, however, is likely to be the sheer cost of thirty hormonal assays for each subject. On top of this is the question of available laboratory capacity to carry out the tests—on the basis of the manufacturer's own figures, they hope to generate a level of business per 'developing family practice' which would produce a laboratory load of 3,100 hormone assays.

With the exception of the last product described, all the commercial prior art items which we have found may be called 'breast cancer detection aids'. As such, their use is limited, since any patient who already has cancer has a reduced risk of survival and a certainty of morbidity. On the other hand, any subject who tests negative, is only negative on the day of the test a nd ha s no idea of her future risk status.

In addition to the commercial items, immediately hereinbefore described, we have now become aware of a number of other patents which are considered relevant. We do not know if any of these disclosures have been commercialized.

U.S. Pat. No. 3,830,224, to Vanzetti et al, discloses means for detecting changes in temperature of the skin incorporating a plurality of multi layer packages comprising liquid crystals. No means for direct or relative measurement of temperatures is disclosed and the authors suggest that physiological phenomena such as ovulation or the presence of malignancy can be revealed by color differences between adjacent packages.

U.S. Pat. No. 3,847,139, to Flam, discloses another liquid crystal device, in this case the liquid crystal system is carried upon a fabric or textile made up into a garment worn between the neck and the waist, including the breast area. As with the Vanzetti et al patent, there is no means for direct or relative measurement of temperatures disclosed.

U.S. Pat. No. 4,522,778, to Brown, Jr. et al, shares with Flam the use of a cholesteric liquid crystal display which visually indicates areas of differential temperature with a chromatic display. Although color differentiated thermograms are generated, it is necessary to insert a strip thermometer between the device and the screen in order to measure actual skin temperatures. The thermograms must be traced by hand. As disclosed, both in the text of the specification and in the accompanying figures, it seems very unlikely that the breast scanning pad of the system could conform to the complex contours of the human breast which is necessary to ensure uniform contact. Similarly, it seems equally unlikely that this pre-requisite would be significantly assisted by an overlay web described as plastics such as polyvinyl chloride or polypropylene.

In U.S. Pat. No. 6,086,247, to von Hollen, there is disclosed a mushroom-like shaped pad. Despite the author's reservations concerning adhesive pads expressed in his discussion of the background, the disclosure calls for just such an adhesive arrangement. In addition, this patent calls for a device in multiple sizes whereas again, in the background to the invention, the inventor refers to this feature, in relation to the Sagi patents, as a limitation with regard to those disclosures. In any event, the device, as described with reference to a preferred embodiment, requires the close involvement of a skilled third party to fit, remove the device and to read and interpret color changes in the sensors. This is another liquid crystal device with no direct or relative temperature measurements. In common with all liquid crystal display devices, there is ample evidence that such devices are not sufficiently sensitive to detect the very small fluctuations in breast temperatures which may be crucial to useful breast assessment.

U.S. Pat. No. 6,077,228, to Schonberger, is directed to the detection of actual breast tumors which, by virtue of having developed a blood supply as a result of angiogenesis, are claimed to act as heat sinks leading to differential cooling when the breasts of a subject are iced. Structurally and morphologically, the device has similarities to the Sagi disclosures of a patch and to the von Hollen disclosure in that all are intended to cover most of the breast. In the case of the Schonberger device, it seems likely that compliance might be a significant issue since subjects are required to have their breasts iced during the test.

U.S. Pat. No. 5,999,843, to Anbar, is concerned with detection of actual breast cancer using what the author calls Dynamic Area Telethermometry and infra-red imaging. Anbar states that "unlike classical, thermography of the breast, the DAT test does not use the absolute temperature or temperature differences as the diagnostic parameter". This is in marked contradistinction to the instant invention hereinafter described.

U.S. Pat. No. 5,941,832 to Tumey et al and U.S. Pat. No. 5,301,681 to DeBan et al; are structurally substantially identical and share mostly the same inventor group. In FIG. 1 of both patents there is illustrated a template with four arms, each of which is adapted by the provision of a series of holes. The arms extend radially outwardly from a central portion and the template is of a sufficient size to accommodate numerous breast sizes. The central portion has an opening which is placed over the nipple to position the template and from both disclosures it is dear that the authors are teaching a template for marking purposes. Once the desired positions have been marked, the template is discarded and sensors, preferably thermistors, are adhesively attached directly to the breast skin of the subject. Signals from the sensors are used in conjunction with a neural network. The limitations of adhesively attached sensors on the human breast, particularly in regard to acceptability and compliance have been rehearsed hereinbefore with respect to various patents.

U.S. Pat. No. 3,960,138, to Doss et al, requires a thermally conductive sensor pad placed in the interior of breast receiving cups of a brassiere in good thermal contact with the wearers flesh. The requirement to use a brassiere is similar to that of the Simpson patents, as are the limitations. In this patent a thermistor is attached to each pad and forms part of a Wheatstone Bridge circuit. Temperature differences between sensor pads unbalance the bridge circuit.

U.S. Pat. No. 5,830,159, to Netta, is another brassiere-based device which the inventor calls a flat tell mammogram. It has a temperature sensor in each cup. The device also includes a pair of strain gauges each coupled to an associated cup of the brassiere. Such coupling is preferably afforded adjacent a central extent of the bottom edge thereof. In operation, each strain gauge is adapted to emit a pressure signal representative of a current pressure that is exerted by the breast on the associated cup. Such pressure is a direct function of the size of the breast. It should be noted that more than one temperature and pressure sensor may be coupled to each cup of the brassiere for providing a more accurate indication of the temperature and size of various areas of the breast.

A PCT patent application PCT/US90/02203 by Bio-Monitor Inc is published as WO 90/13092 and indicates that the inventor was Gautherie. The publication discloses a method and apparatus for analyzing information gathered from symmetric areas of a living organism. Recorded data are transmitted over a communications link to a remote data analysis center and ipsilateral and contralateral comparisons of selected temperature data are made along with a chronobiologic analysis of the temperature data. Although Gautherie did not restrict his disclosure to temperature measurement, this application is discussed and FIG. 1 and the supporting text illustrate a plurality of sensors, directly affixed to the breasts, including on the nipple/areolar area, with adhesive pads. These are connected with wires to a data collection device worn on a waist band or belt.

Gautherie makes no disclosure concerning a structure for control of the ten wires between the points of attachment on the breasts and his data acquisition device. This is particularly surprising since he states, on Page 7, that temperature data is recorded every five minutes over a twenty-four hour interval under ambulatory conditions. With multiple unconstrained wires, it is not realistic to confidently expect that all sensors would remain attached, for instance during sleep periods, even if a brassiere were to be used. There is no disclosure on the type of sensors nor the calibration thereof.

A further serious concern is that although Gautherie describes how data from the subject-worn acquisition device would be transferred to the remote analysis center, the crucial issue of secure attachment of subject identity to data is entirely in the hands of an operator with the attendant risk of disastrous human error. Such an event could lead to a sick patient being declared healthy and subsequently dying and a healthy subject being possibly subjected to disfiguring and inappropriate surgery.

A search conducted in October 2000 using the public resources of the European Patent Office did not reveal any issued patent to Gautherie or BioMonitor Inc on this or any related subject. It was also not possible to find any reference to BioMonitor Inc on the internet.

U.S. Pat. No. 5,813,400, to Devlin et al, is concerned with a connector connected to an electrode set and another connector connected to a patient monitor. Each electrode element of the connector is exclusively coded to identify it to the monitor. Such a solution would be useful in systems where a non permanent hard-wired connection between sensors and a monitor is possible or, optionally, disconnectable means would be desirable, such as where a monitor does not provide specific channel to specific sensor functions, such as calibration. The invention appears to be directed towards ensuring correct spatial configuration of electrodes particularly for purposes of EEG and EKG monitoring.

Work published by Simpson and others, well after the date of his patents, includes comparative microscopy data in cancer-associated breasts and age-matched normal breasts showing a gross excess of focal hyperplasias in premenopausal cancer-associated breast tissue. Additionally, epidemiological data are consistent with this finding in that such tissue is subject to a six-fold increased risk of further primary carcinogenesis. In addition, it is now known that premenopausal mammary tissue goes into a monthly pregnancy rehearsal with glandular proliferation and increased blood supply. These phenomena have been shown to produce a luteal heat cycle which produces a variation in breast surface temperature of about 1° C. in normal women (probably not at risk of cancer). Women with cancer-associated breasts exhibit only up to about half this amplitude. The pattern of temperature rise is also different insofar as the temperature rise curve in cancer-associated breasts is relatively steady and peaks earlier in the menstrual cycle than in normals. Normals exhibit a high correlation with and dependence upon endogenous progesterone levels during the luteal phase.

The differences in breast temperatures between 'normal' women and clinically normal women with cancer-associated breasts, measured during the luteal heat cycle, are maximal during the few days just after ovulation. Breast temperature variations may be associated, at least in part, with abnormal breast arterial blood flows at particular phases of the menstrual cycle. Significantly increased blood flow commences at the start of the luteal phase, some fourteen days prior to menses. The blood supply of the breast is from the axillary artery via the lateral thoracic and acromio-thoracic branches and also from the internal mammary (thoracic) artery via its perforating branches. In the female, the branches of the second, third and fourth intercostal spaces give branches to the breast which vary in size under hormonal bombardment. Thus, although the contribution to overall elevation in breast temperature may be greater by some arteries than others, all exhibit a menstrual cycle of breast blood flow and all contribute to the breast luteal heat cycle.

In any system or device for breast surface temperature measurement which is to have broad applicability for mass screening of populations, great attention has to be given to practicability. Any such entity which consumes large amounts of time in setting up will be unacceptable.

For this reason, the physical attachment of sensors to the breast surface of subjects has not proven popular. The need to apply each sensor separately, usually with adhesive tape, is not only time consuming but has obvious disadvantages for the subject at the time of removal. There is also the problem of ensuring that individual sensors do not become detached as a result of traction on cable connecting means employed to deliver the signal to whatever means is employed for temperature data collection.

The use of a sensor array, integral with a brassiere (this garment also having means for carrying a data-logging device) is, apparently, the preferred implementation of the Simpson and Green utilities. This device, which was never supplied commercially, had the name Chronobra™ and Simpson has published on this in the lay press as recently as September 1997. It is clear from other publications on this device that, although it has some functionality, there are inherent problems of poor signal, intermittent signal and sometimes a complete absence of signal, logged from certain individual sensors suggesting poor and inconsistent contact between these and the breast surface.

Analysis of the device, an example of which we obtained, suggested that the problems were unlikely to be truly electrical but are related to the structure and mechanics of the device. The manner in which thermal sensors and the garment are integrated involves the use of a sewn-in lining pad made of stiff material and provided with a plurality of perforations. A plurality of thermal sensors is each encapsulated within in a thick molding of silicone material which is in the shape of a cylindrical plug which is 'T' shaped in cross-section, each sensor being located in the 'leg' of a 'T'. The sensor moldings are disposed between the perforated lining pads and the cups of the brassiere. Each perforation in the lining pad accommodates the leg portion of one thermal sensor molding so as to present it to the breast surface.

We measured the thickness of the silicone mold material disposed about a number of sensors and in no case was this less than 2.0 mm. However, the least thickness measured at the end of a molding over that surface of the sensor directed towards the breast was 3.1 mm and in some cases over 4.0 mm. Since silicone rubbers are highly effective insulating materials with poor thermal conductivity, it is certain that this arrangement would lead to reduced effectiveness and possibly to repeated low readings. Simpson and Green's disclosures call for insulating means to prevent heat loss and this may be why they employed a large plug of the selected material behind the sensors.

However, to employ such a material over the face of the active thermal sensing element suggests a fundamental misunderstanding of the principal aim at hand, which is the measurement of small variations in temperature of a target in an ambient environment, the temperature of which is not vastly different from the target itself.

Under these circumstances, the principal aim is only likely to be met either when there is no barrier at all or, if there is one, it has high thermal conductivity and is of minimal thickness.

Further analysis of the subject Chronobra™ device, both on and off subjects, suggests other reasons why instances of intermittent or absent signal are encountered. First, the integral construction of the sensor array and brassiere called for by the Simpson and Green patents and embodied in the use of a lining pad, leads to a rather rigid cup construction which resembles a rounded modified cone. In most women, the breast surface is profoundly convex on the lower aspect and somewhat concave on the superior aspect. Such a mis-match of profiles explains why, in a number of cases, the sensor moldings of the upper aspect of the cups do not come into contact with the superior aspect of the breast surface at all.

Such a brassiere must, of course, be available in all rational sizes if a general population is to be tested. This inevitably increases the cost and level of inconvenience associated with this test and many others in the prior art.

Mounting the data-logging device on the brassiere—which reads for the Simpson and Green patents—between and below the cups, introduces traction on the brassiere and exacerbates the non-contact problem by pulling the upper surfaces of the cups away from the superior aspect of the breast surfaces. Each fine, twisted pair of sensor connecting leads extends from the sensor to the data-logging device separately and without further protection. This not only makes for an untidy appearance but also increases the risk of tangling and traction on individual sensors. Finally, this device does not use any form of true calibration and therefore it cannot be argued that the output from the sensors represents accurately any particular absolute temperature.

Despite a prolific prior art, it appears that a number of crucial factors have not been addressed in the collection of physiological signals from the surface of the human breast, particularly when it is the intention to apply any given solution to a large population.

First of all, no solutions in the prior art appear to deal adequately with the crucial issues of the subject interface. Any workable solution for mass application must meet the following requirements in this area:

1. Provide intimate and continuous contact, throughout any data collection period, between that part of the subject breast surface which is to be monitored and sensor means provided for the purpose of collecting the target physiological signals.

This is crucial since, if the subject interface is intermittent, collection of data will also be intermittent and may be useless. This, in turn, represents a waste of limited screening resources, a waste of the subject's time and also, quite possibly, increased stress;

2. Provide sensor means which are capable of reliably and accurately registering very small differences in absolute signal values.

This is crucial with respect to breast surface temperature signals since, as hereinbefore discussed, women with cancer-associated breasts may exhibit temperature variations of only up to about 0.5° C. and, in this context, sensors which measure absolute values with a sensitivity of at least 0.1° C., and preferably considerably greater sensitivity, are clearly necessary. This applies even if only inter-sensor relative values are required to be elaborated or interpreted post data collection;

3. Present no material physical or thermal barrier between the breast surface and the sensor means in order to ensure that signal attenuation does not occur.

As immediately hereinbefore discussed, variations in physiological signals, particularly breast surface temperature signals, may be of very low amplitude and place high demands on sensor means. Any physical or thermal barrier interposed between the target and the sensor could produce a thermal gradient leading to the collection of incorrect data which could, in turn, lead to an incorrect and potentially dangerous interpretation;

4. Provide an interface which does not intrinsically limit compliance with or management of the data collection process.

This is crucial because, notwithstanding the great threat which most women perceive breast cancer to be, they will not, on a population-wide basis, accept screening methods which are painful, cause loss of dignity, are overly time consuming, compromise hygiene or are clearly unreliable. Similarly, health care and diagnostic service providers will not implement screening programs which introduce tasks or functions, other than the screening process itself, which do not form part of the organization's core activities. Thus, solutions which require fixing of sensors directly to the breasts with adhesives, especially for long periods, are unlikely to be acceptable to the majority of women. Similarly, those solutions which require very many sizes of brassieres, whether dedicated to a particular test or general purpose, are unlikely to be acceptable to the majority of service providers since they introduce a manpower and cost requirement in respect of laundry or other cleaning means, together with extended inventory control.

Secondly, few solutions in the prior art appear to deal, at all, with the crucial issue of the integrity of measurements to be made by the sensor means. Those that do—Simpson and DeBan/Tumey—use an algorithm method for calibration of sensor means which, by itself, may not be safe when it is considered that the level of accuracy required for thermometric measurements, in the context of breast cancer diagnosis or risk, is measurement to better than 0.1° C.

Thirdly, none of the solutions in the prior art appear to disclose safe means for or to deal adequately with the crucial issue of ensuring that a unique identity of the subject is non-detachably linked to data collected from that subject in order to eliminate human error at the time collected data are transferred between a subject interface and any other storage or elaboration point. Furthermore, none of the prior art solutions addresses the issue of non-detachably linking the identities of any persons involved in attaching or detaching the subject interface, initiating or ending the collection of data, transferring or interpreting data or holding overall responsibility for the screening process and its consequences. Considering the importance and potentially life-threatening consequences of errors in this context, this seems remarkable.

Overall, the prior art teaches towards the desirability of a convenient method for breast screening based on thermometric data. However, none of the references we have been able to find, whether considered alone or jointly, teach a solution which is accurate, safe, acceptable and workable at both the subject and provider levels.

Since most authorities now accept that about one in twelve women in Europe and maybe as many as one in ten in the USA, dies from breast cancer and up to one in eight may develop the disease at some point in their lives, it would clearly be of enormous benefit to be able to identify which women are at risk and which are not. By such a means of risk-assessment, very great relief from stress could be imparted to the majority of women. Even women found to be at risk would be much better off since the health care system, whether public or private insurance based, would be able to release funds to enhance their surveillance, implement better avoidance strategies (perhaps involving diet and nutritional supplementation) and treat them better, should the disease eventually supervene. We estimate that in the U.K. alone, having an effective means for positively identifying those who are at risk and three quarters of those who are not at risk, would save £1.8 billion (US$ 2.7 billion) per annum, as well as avoiding a vast amount of human misery.

Clearly, there is room for substantial improvement in the management of breast cancer since the long term survival prospects, following diagnosis, are still not very encouraging, barely exceeding 50%. Mass campaigns directed at self-examination are not very successful since, even when regularly practised, women who find lumps which turn out to be malignant upon biopsy, generally detect these at a size which is lethal. This is particularly so in young women with dense breast tissue.

It may be that today's limited success in treating this disease is partly due to the failure to recognize pre-cancerous states in mammary tissue as a whole. The investigation, observation and tracking of these states would allow earlier diagnosis and would also permit potential intervention strategies to be exploited, perhaps with marked effects on ultimate survival rates.

Other documents considered relevant are:

Gautherie, M and Gros, C M, "Breast thermography and cancer risk prediction", 45: 51–56, 1980.

Simpson, H W and Griffiths, K. "The diagnosis of breast pre-cancer by the Chronobra", Chronobiology International Vol. 6, No. 4: 355–393, 1989.

Simpson, H W et al., "The luteal heat cycle of the breast in health", Breast Cancer Research and Treatment, 27: 239–45, 1993.

Simpson, H W et al., "A non-invasive test for the pre-cancerous breast", Eur. J. Cancer, Vol 31A, No. 11: 1768–1772, 1995.

Simpson, H W et al., "The luteal heat cycle of the breast in disease", Breast Cancer Research and Treatment, 37: 169–178, 1996.

Simpson, H W. Sir James Young Simpson, Memorial Lecture 1995: "Breast cancer prevention: a pathologists approach", J. R. Coll. Surg. Edinb., 41, 359–366 December 1996.

Simpson, H W et al., "A clinical test for breast pre-cancer", Policlinico (Chrono)., 1995; 1: 23–30

Hayes, L et al., "Increased breast temperature in the 'at risk' breast", B. J. Cancer., 83, Supplement 1, 41, July 2000; also presented at the British Cancer Research Meeting, Jul. 9–12, 2000.

OUTLINE OF THE PRESENT INVENTION

This invention is based on the observation that, in general, an increased risk of developing breast cancer later in life, pre-cancerous states of the breast and breast cancer may be recognized from accurate observations of breast surface temperatures using suitable apparatus and methods.

As hereinbefore noted, prior art thermometric breast assessment devices are in the form of sensors physically attached to the breast surface, brassieres with integral sensors or brassiere inserts which fit within, and which are retained by, the cups of a brassiere. Furthermore, with only one exception, all of those which we have been able to find are concerned with the detection of an actual cancerous lesion.

In marked contradistinction to prior art devices, the instant invention is neither physically attached to the breast surface and is also neither a brassiere nor a brassiere insert. Furthermore, it is primarily directed, by means of the function of its structural elements, towards the assessment and determination of the risk of developing cancer later in life by the measurement of breast temperatures, over a period normally of one and a half hours. Notwithstanding this, the instant invention may also be used to detect breast cancer and is useful in other areas, such as measuring the effect on breast temperatures of interventional strategies, including dietary strategies, in women at-risk, for instance those who carry genes associated with an increased breast cancer risk such as inter alia, BRCA1 and BRCA2.

In the original embodiment of the instant invention, a universal harness, only one size of which is needed to fit the great majority of subjects, comprises two flexible, flat, ring-like contactor pads, united anteriorly by a short, adjustable, elasticated strap and united posteriorly by a longer, adjustable and openable strap. The harness may be used in conjunction with the subject's own brassiere or without a brassiere, according mainly to the choice of the investigator. Each contactor pad comprises substantially similarly sized and shaped inner and outer layers of flexible, compressible and extensible material which, conveniently, may be neoprene, provided with suitable flexible facing fabrics, such as the nylon material known commercially as Lycra™.

Each contactor pad layer has two extension tabs, disposed about opposite ends of a diameter, for the attachment of the short anterior strap and the longer, openable, posterior strap. The contactor pad layers each have a central hole which is so sized that it will accommodate the areolar area of the majority of women and is conveniently about 50 mm in diameter. The outer diameter is conveniently about 100 mm. The inner and outer contactor pad layers are laid one over the other such that the extension tabs are aligned and are then stitched together around the circumference of the central hole.

An array of thermal sensors, preferably, but not necessarily, four in number, is disposed about the inner surface of the inner contact pad layer in a regular manner along the circular center line lying between the inner and outer boundaries. The sensors are preferably of the analog type which produce a current in proportion to temperature and are housed in a transistor can package. Each sensor of this type has three wire legs which are introduced through the material of the inner contactor pad layer. The neoprene material effectively self-seals against each sensor leg. The sensor cans are completely unsheathed, having no additional covering of any kind, in order to ensure contact with the breast surface and to maximize thermal transfer.

The three legs of each can package each engages a small disc-like molding, provided with through holes disposed, in its periphery, 120° apart. The legs are then bent over at the periphery of the disc providing initial securing means for this assembly. Cable connecting means are in the form of light, flexible, plastics-sheathed outers each provided with a plurality of twisted pairs of inner cables, the number of pairs being the same as the number of sensors provided on each contactor pad. It is strongly preferred that a different color outer cable covering is used for each contactor ring and that a convention is adopted, during use, that the first color is always used with a first breast and that the second color is always used with a second breast. Wiring is accomplished according to a novel strategy directed towards ensuring that individual sensors are never subjected to traction in normal robust use.

Flexible insulating and cushioning means are introduced intimately about the sensor legs and connections and between the contactor pad layers which are then sewn together to complete the contactor pads. These are soft and compressible and have a 'bulked' feel. The contactor pads are 'handed' and the sheathed outers of the cables are directed medially. A short, elastic, adjustable, anterior strap is sewn between medial tabs on each contactor pad. A longer elasticated, adjustable and openable posterior strap, is sewn to laterally directed tabs on each contactor pad.

The colored connecting cables terminate within the case of a monitor unit and preferably have a softness such that they drape readily under their own weight. This monitor is provided with electronic micro-circuitry which provides timing and memory means capable of polling each sensor, every sixty seconds, for one and a half hours and storing the data so collected. The sensors are, preferably, independently calibrated to within 0.01° C. using pre-set potentiometer means located within the monitor unit. This is a much greater level of accuracy than prior art thermometric devices and is necessary to fulfill the purpose for which the apparatus is intended. The monitor is preferably powered by a rechargeable nickel hydride battery. The monitor is provided with a series of colored LEDs which indicate status of the system under a variety of conditions.

The temperature sensing cycle is initiated by depressing a plunger and the monitor unit switches off automatically at the end of the sensing cycle.

Data stored within the monitor is downloaded to a host PC, via an interface unit to which it is attached, with suitable connecting cable and plug means. The interface also provides charging means and this function is activated upon connection, whether the monitor is downloading or not. Conveniently, the interface will provide charging services for a plurality of monitor units, typically twelve at one time. The original disclosure called for a host PC, which preferably had a 100 MHz processor or better and used the Windows 95™ operating system. However, it is in the nature of both processor development and operating system software development that they have been superseded by more powerful equivalents. The PC was to be provided with a dedicated program written, for instance, in Turbo-Pascal™ for Windows™, this program being capable, under keyboard or mouse command, of communicating with the monitor unit, initiating data download, capturing and saving downloaded data and displaying this in graphical and tabular form for each sensor. In addition the program provides means for pictorial graphic display of the temperature measured by each sensor, at each polling, displayed in its correct spatial position on each breast.

Re-setting the monitor unit for further use is normally carried out from Within the host computer, using software means, however, should there be a reason to abort a sensing cycle and start another, this is accomplished by depressing a re-start button mounted sub-flush with respect to the surface of the monitor case.

In use, the subject to be investigated, who will generally be between twenty and fifty years of age and, in any event, will not have reached the menopause, is counseled upon recruitment as to the nature of the test. Some time prior to the test, she is provided with a urine dip test kit which will indicate the day upon which she has a marked rise in luteinizing hormone. She is also provided with a series of sterile bottles in which to collect a series of at least three early morning saliva samples which, when the series is complete, are forwarded in the container provided, to a suitable laboratory equipped to carry out assays of salivary progesterone levels. These results are used to measure and predict the most suitable date in the subject's next cycle to carry out the breast temperature test.

On the appropriate day, the subject is called to the location where the test is to be conducted. In a warm environment, where the ambient temperature should be 24° C.±2° C., the subject is fitted with the harness of the instant invention. The subject may, in addition, wear her own brassiere if she wishes, or a sports type elasticated brassiere, or no brassiere. She should, however, wear a substantial and reasonably close-fitting over garment, to limit or prevent any generalized heat loss. It is essential that identification details relating to both the subject and the monitor unit are recorded together and that the integrity of this combined information is maintained. Only one size of the instant harness is normally provided and required.

The sheathed connecting leads between the harness and the monitor unit are led out from under the lower margin of the over garment. To start the test, the assistant, helper or other designated person depresses the plunger on the monitor unit, observing that the 'start' LED illuminates, to confirm initiation of the test. It will be found convenient if the subject is provided with a dressing gown in order that the monitor unit may be placed in a pocket during the test. Throughout the test period, the subject should be encouraged to sit quietly and avoid exertion and should not imbibe hot or stimulating liquids. At the end of one and a half hours, of which the first half hour is to allow that part of the apparatus in contact with the subject to equilibrate with the subject's surface temperature, the test will be complete and the subject may return to a private cubicle to doff the harness and dress in her normal clothing prior to departure from the test center.

The data from the monitor unit used with the subject is downloaded into the computer, as hereinbefore described, and evaluated by a skilled trained person capable of comparing the subject's breast temperature data with known norms with a view to reaching a conclusion concerning whether or not subject may be at risk of developing breast cancer at a future date.

In the event that this conclusion is positive, the subject would be informed promptly and invited back to participate first in a re-test and then in other tests. The purpose of these is to establish whether or not she may have existing cancer since, although the object of the test of the instant invention is not, primarily, to detect actual cancers, there will be some subjects who come forward who do have the undiagnosed condition. If she is negative to other tests for cancer, she will be informed that she is at a significant risk of developing breast cancer subsequently. This knowledge allows surveillance, prevention and future intervention strategies to be planned and implemented. These factors, in turn, improve the chances of preventing the disease or, should it prevail, successfully treating it at an early stage.

On the other hand, if the test is negative, the subject will also be so informed. In this event, the subject may well be reassured, however, she should be advised that she should return for retesting at a suitable interval which may be, say, two years. In any case, a follow up record and call-forward system should be maintained in order that any subjects which test negative can be called for a re-test after a suitable period.

The foregoing apparatus of the original embodiment of this invention underwent initial human trials at The European Institute of Oncology, Milan, Italy, according to a protocol which reflected the general method of use immediately hereinbefore described. These trials generally demonstrated that, in marked contradistinction to the Simpson and Green Chronobra™ device, the novel harness and sensor arrangement is capable of producing a continuous reliable signal throughout a data collection period. The apparatus was also used in a few subjects prior to but on the same day that they were diagnosed with breast cancer by a 'gold standard' method, such as biopsy, and, in some of these, temperature 'anomalies' were detected.

IMPROVEMENTS SINCE THE ORIGINAL DISCLOSURE

We have now made numerous improvements, which will be disclosed hereinafter, as a new and most preferred embodiment. The majority of our efforts have been directed towards non-obvious structural improvements with the intention of achieving enhanced reliability, durability, accuracy, acceptability for the test subject and service provider, effectiveness and security.

As in the original embodiment of the instant invention, a universal harness, only one size of which is needed to fit the majority of subjects, comprises two novel ring-like contactor pads. However, we now prefer not to unite the contactor pads anteriorly with direct means. The harness may be used in conjunction with the subject's own brassiere or without a brassiere, according mainly to the choice of the investigator.

Improved harness means includes improved contactor pads, each including a thin flexible printed circuit board (PCB) manufactured flat as a ribbon and having an overall shape somewhat reminiscent of a large inverted question mark with an extended tail. It is to be understood that in the improved harness, one design of PCB may be used by adopting both a right and a left orientation. A first portion forms, substantially, an incomplete circle, the inner margin of which, in the flat condition, largely encloses a circular area; a second portion, continuous with the first portion, is curved and extends over some 90° of arc; and a third portion, continuous with the second portion, is substantially straight to form a lead and extends to a second end.

A plurality of novel integral flexible primary tabs is provided about the inner margin of the first circular portion of the ribbon PCB, preferably but not necessarily disposed at intervals of 60° and which extend radially and inwardly. A further plurality of similar integral primary tabs may, optionally, be disposed about the greater part of the outer margin of the first circular portion of the ribbon PCB.

The ribbon PCB carries electrical connection means in the form of insulated copper tracks, adapted by the provision of suitable perforations, on each primary tab, to provide reception and mounting means for surface mounting thermal sensor means. Perforated reception and mounting means are adapted in such a manner as to allow thermal sensor means to be mounted on either side of the primary tabs.

A plurality of integral secondary tabs is provided, extending radially inwardly and outwardly, in pairs, at convenient positions around the first circular portion of the ribbon PCB. One pair of secondary tabs is preferably disposed near the top of the 'question mark shaped' ribbon PCB and a second pair is preferably disposed at that point where the first circular portion of the ribbon PCB adjoins the second curved portion.

All the secondary tabs are reinforced and also adapted by the provision of fold lines in the ribbon PCB material to allow them to each be formed into an outwardly directed flap. Each pair of secondary tabs is further adapted by the provision of one in each pair with a self-adhesive pad of hook closure material and the other with a pad of loop closure material in a corresponding desired position such that, when the flap formed by each secondary tab of one pair is folded and closure is effected, receiving means is formed for the releasable and slidable receival of body strap elements of the harness.

Each of the secondary tabs forming that pair positioned adjacent the second curved portion of the ribbon PCB, is further adapted in regions close to their origins from the inner and outer margins of the ribbon PCB by the provision of fixing means, conveniently in the form of soldering points exposed on both sides and incorporated at the time of manufacture. Similar fixing means are provided on small extensions formed on the inner and outer margins of the first end of the ribbon PCB. During assembly, soldering points located on the inner and outer margins of the first end of the first portion of the ribbon PCB and corresponding soldering points located on the inner and outer secondary tabs are drawn into apposition and wire and solder joints made, thereby forming a flexible annulus which is also, substantially, a frustum of a cone.

By drawing the soldering points located on the front aspect of the first end of the first ribbon PCB into apposition with those located on the rear aspect of the secondary tabs, the frustum will be formed in such a manner as to provide a novel accommodating structure for a left breast. Conversely, by drawing the soldering points located on the rear aspect of the first end of the second ribbon PCB into apposition with those located on the front aspect of the secondary tabs, the frustum will be formed in such a manner as to provide an accommodating structure for a right breast. Two of these structures may be combined in a compound structure which, with suitable cleanable, permanent covering means, forms a pair of contactor pads suitable for accommodating a pair of human female breasts.

Each primary tab is provided with a thin layer of closed cell foam of similar size and shape, adhesively applied on both aspects to prevent heat loss and damage to the covers from soldering points.

Body strap elements of the harness comprise multiple elasticated strapping elements which include releasable attachment and adjustment means for attachment to the human female body in the breast area. In particular, two transverse anterior straps are joined at both ends and at each end to a posterior strap forming a 'Y' configuration with an enclosed angle conveniently of about 40°. A short vertical anterior elasticated strap is non-releasably secured centrally and at right angles to one transverse anterior elasticated strap and releasably and adjustably to the other.

The relationship between the body strap elements of the harness and the flexible contactor pad elements is important and the width of the transverse anterior elasticated straps is selected so that the latter may be readily and releasably engaged, in a slidable manner, with the folded flap closures formed by the secondary tabs on the contactor pads. Fundamentally precise positioning of each contactor pad over each breast, concentric with the nipple, is possible partly by virtue of the provision of the second curved portion of the ribbon PCB and partly due to the fact that the contactor pads may be freely located with respect to one another over any rational range. The dispositions on the first circular portion of the ribbon PCB of the secondary tabs forming securing means for the transverse anterior straps and the geometry of the mutual permanent attachments between these straps are selected to optimize contact between the contactor pads and the subjects breasts. The short vertical anterior strap provides further adjustment directed towards optimizing pad-to-breast contact, particularly on the medial aspects, by allowing the transverse anterior straps to be gently drawn towards one another in the central area between the breasts. Both the contactor pad sub-assemblies and the body strap elements are intended to provide a one-size-fits-all solution for the great majority of the population, however, it is recognized that there will be a need for a low use variant for extremely large subjects and another for extremely small subjects. This is a significant improvement over prior art systems which depend upon a multiplicity of sizes of brassiere or brassiere inserts.

However, more important than any of these factors is the provision of the primary tabs for sensor mounting. These are so sized and shaped that, whatever breast size or shape the first circular portion of the ribbon PCB is drawn against, with the breasts protruding through the flexible frustum structure, primary tabs will tend to be splayed gently but firmly into compressive contact with the breast surface.

We now prefer to use seven sensors in each array, preferably six sensors disposed symmetrically on primary tabs on the inner margin of each contactor pad and one further sensor disposed on the outer margin on a primary tab directed towards the axilla. We prefer a precision temperature monitor integrated circuit of analog type which produces a current in proportion to temperature though there are now available temperature-voltage based types which could be used with little difference in performance in general use. All primary tabs are provided with second exposed grouped multiple soldering points, which constitute bridging wiring connection means for most preferred sensor means and also connection means for micro-miniature trimming components and bridging wiring connection means for alternate versions of this most preferred embodiment which employ temperature-voltage based type sensors.

The most preferred sensor has cylindrical, flanged, metal can package with a flat-topped upper surface having a curved periphery. Each sensor has three stiff wire legs for engagement with a thin plastics insulating spacer washer and perforated soldering points on primary tabs. The plastics washer prevents any risk of short circuiting the metal can on the soldering points and raises the exposed profile of the sensor above the cover of the PCB. The functional surfaces of sensors are used unsheathed, in order to ensure intimate contact with the breast surface and to maximize thermal transfer. Each sensor is individually resistance calibrated to ±0.01° C.

Thin closed cell foam layers cover both sides of each primary tab. Those on the sensor mounting side have a die cut substantially circular hole which registers with and passes over the flange of the can package so that it fits intimately over the plastics disk washer. A circular die cut hole in the cover fits intimately around the cylindrical body portion of the metal can package and also lies intimately above and upon the flange. On that side of each primary tab facing away from the breast, the primary function of the closed cell foam layer is to prevent radiant and conductive heat loss from the primary tab and, most especially, from the associated sensor and the secondary function of mitigating the potential for any residual solder nibs or trimmed wire ends to abrade or pierce the cover.

On the breast facing side, the primary function of the closed cell foam layer is to prevent any damage residual solder nibs or trimmed wire ends and to prevent any undesirable breast contact with these.

The secondary function is prevention of heat loss and this is important because, if the closed cell foam layer were not interposed between the cover and the PCB, the proximity of copper tracking within the PCB could lead to undesirable lateral conductive heat loss. This would be unacceptable in the context of an apparatus intended to measure temperature differences to ±0.01° C.

It will now be appreciated that, in this improved version of the harness of the instant invention, we have disclosed structural and functional improvements, eliminated a number of components and numerous manufacturing steps and, additionally, the weight has been reduced. Furthermore, the drape characteristics of covered ribbon PCBs are considerably improved when compared to the sheathed cables of the original embodiment, which each carry eight twisted wire pairs, and advantage is taken of this in the straight portions of the ribbon which constitute connection leads to a data-logger.

Data-logging means are provided in the form of a data-logger having significantly improved functionality, safety and security over that which we disclosed in the original embodiment of the instant invention as a monitor unit. An exposed area near the second end of the PCB is adapted in each case by the provision of discrete exposed soldering points. This portion of the two PCBs is each received, respectively, into the data-logger where they are provided with both mechanical securing means and electrical connection means preferably in the form of permanently soldered connections. The data-logger is lightweight and has a substantially oblong plastics case, and preferably is worn suspended from the neck of a subject on a light adjustable strap having quick release connection means.

The data-logger, which provides significantly improved functionality, safety and security over the monitor unit disclosed in the original embodiment of the instant invention, is provided with electronic microcircuitry based around a microprocessor which is used to control data collection, storage and subsequent downloading of recorded data to the host PC. The data-logger is a sixteen-channel device, of which fourteen channels are used to monitor outputs from each sensor comprising the two seven-sensor left and right breast sensor arrays. Two channels are used to confirm the integrity of harness. The data-logger is provided with clock timing means and the processor is capable of polling every sensor at selected intervals for periods of up to seven days. Individual sensors are each calibrated to ±0.01° C. at the time of manufacture of the data-logger by adjusting the calibration resistance. This high level of accuracy, which is not found in the prior art, is essential in this apparatus in order to fulfill the purpose of breast thermometry testing in the context of breast cancer risk and breast cancer. Each of the sensors is polled in rapid sequence, using analog multiplexers. Each of the sensor readings is fed into an operational amplifier, which conditions the signal so that it can be processed. This is achieved by converting the analog signal into a digital one using an analog to digital converter. Once in digital form, the data from a set of readings are stored in non-volatile flash memory until the microprocessor is instructed to upload data to the host PC. The operations of writing and addressing, the duration of the readings, as well as the time between readings, are all controlled by the microprocessor. The data-logger is powered using rechargeable batteries. Separate voltage levels are used for the analog and digital parts of the circuit in order to reduce interference and these are controlled using regulator chips to maintain correct values. A separate control amplifier is provided to monitor an ambient temperature sensor mounted on the data-logger case. A further separate control amplifier is provided to monitor an additional sensor used to measure a non-breast body surface reference temperature and attached to the data-logger by a flying lead.

The data-logger is provided with display means in the form of light emitting diodes (LED) which indicate 'power on', 'thermometric test running' and 'low battery status', respectively. Further display means are conveniently in the form of a multi-line, multi character, liquid crystal display (LCD) which indicates electrical status of the data-logger and harness under a variety of conditions and also shows test-critical and test subject security data, including unique test subject identifiers. Push button switches control 'power on/off', 'function display' and 'test initiation', respectively. Provided that the data-logger has been brought to readiness according to a carefully controlled protocol, a temperature sensing cycle can be initiated by pressing the 'test initiation' button. The data-logger switches off automatically at the end of a sensing cycle.

Interaction between the data-logger and the host PC is managed with serial interface means integral with the host PC and in the form of an internal PC card which includes a single upload/download data port. The interface also has multiple charging ports for the automatic battery charging of data-loggers attached to it.

At an appropriate time, stored data within the non-volatile flash memory are uploaded to the host PC via the upload/download data port. After uploading data from any particular subject and until the download of security data from the PC to the data-logger for the next test, the LCD display shows the subject name and test number from the last performed test. Other information can be read from LCD display by toggling the 'function display' button and by noting the condition of LEDs.

The host PC includes an entry level motherboard and microprocessor, or better, suitable operating system and a dedicated software program. Commands which control the flow of data to the host PC are set from the keyboard and mouse of the host PC and sent to the microprocessor of the data-logger via the upload/download data port. Data are date-stamped using an internal real time clock (RTC) within the data-logger. System variables, such as test period and time between sensor readings, are set and downloaded in a similar manner and new values are stored in the non-volatile flash memory of the data-logger for controlling subsequent test parameters. PC software is protected by a hardware security device which, if not connected to the host PC, will prevent all operational access. The security device may, optionally, incorporate means for integrating a credit system for levying a monetary charge for each test.

Access to the dedicated software program is subject to multi-level password access and also time-out control and all operators are required to log a unique password, and then other suitable unique identifier details, such as name, status and, if applicable, employee number, to a designated field displayed on an opening screen on the VDU of the host PC. Access will time-out at a predetermined time at the end of each work day unless temporarily defeated by a task in progress, following the completion of which, access time out will prevail so that if continued access is required it will be necessary for operators to log on once more, thus ensuring that any out-of-hours access is logged to the system. Time out occurs, in any event, at midnight each day.

The dedicated software program provides improved screen data displays and these range from the simple numerical display of temperature data in spreadsheet style to elaborated graphics. All displays follow an informal international standard used by surgeons to reference landmarks on the human breast. This involves representation of the breast from a 'within-subject' viewpoint and then addressing first the upper outer quadrant and proceeding clockwise to the upper inner quadrant.

Since the disclosure of the original embodiment of the instant invention, we have gained a much fuller appreciation of the importance of providing women with better and earlier information on their breast health status. Furthermore, we have encountered press reports of occasional, but disastrous, examples of patient records which have become mixed up, leading to inappropriate surgery or non-diagnosis. We also now know that other important applications include monitoring responses to dietary and other intervention strategies for high risk women, improving the quality of counseling to those considering prophylactic mastectomy and optimizing the time of surgery in very large tumors.

These additional uses support the use of a greater number of sensors in each breast sensor array. However, the primary use of the new and improved embodiment is the assessment of risk in subjects, who appear to be generally healthy, of developing breast cancer later in life. In this large group of women the aim is to collect temperature data generated by a general physiological response to the tidal hormonal flow throughout the menstrual cyde, at a particular point in that cycle. On this basis it would seem that there is no need to collect data from any specific point or points on the breast. However, breast cancer is highly prevalent in the subject population and it is not possible to tell, in advance, whether any given subject, presenting for routine risk assessment, may actually be harboring breast cancer. In mass applications of the instant invention, this scenario will be quite common and there is an implicit duty of care upon any service provider to collect not only general indicative data but also more specific data which may help to localize a lesion, if present.

The method of use of the harness and data-logger of the new and most preferred embodiment will usually be the same, regardless of the application. In the primary application the approach is also, in general, similar to that employed with the original embodiment. In the new applications, the use of serial progesterone assays may or may not be used to determine a specific test day. Where progesterone assays are used, they will be substantially the same as those used in conjunction with the original embodiment.

At any test location, on any test day, for any application of the new and improved embodiment of the improved instant system, authorized operators both of the host PC and data-loggers must log on to the host PC system by entering passwords and identifier details. Access will time-out at a pre-determined time at the end of each work day. A strict protocol involving the input of mandatory entries, concerning the subject, to a new subject record which has a unique alpha numeric identifier must be followed before the host PC can generate a unique test number and then ready a data-logger for use. Providing the data-logger holds no data and has an adequate power reserve, it will be readied for use and the test number, subject surname and first name appear on data-logger LCD display until any upload of collected data. The data-logger will time out if the test is not started within a pre-set time. System variables, including test parameters, may only be varied by an authorized person, such as system engineer, having a higher level of password controlled access.

In a room maintained at 22° C.±2° C., a female helper who is also the data-logger operator assists the subject who doffs her upper garments in privacy. The subject must confirm her first name and surname verbally and must check the spelling of both her names by inspection of the data-logger LCD display. In the event of any discrepancy, the data-logger must not be used until the error has been corrected. This involves postponing the test and readying the data-logger once more. If the subject identity confirmation procedure is not followed, and more than one subject is present at the test location, the entire security of the system could be compromised.

The data-logger is suspended from the neck of the subject on light adjustable strap. The breast accommodating structures of the contactor pads and the body strap assembly are then fitted on to the subject and adjusted so that each contactor pad is located concentrically about a nipple and the primary tabs are splayed into gentle compressive contact with the surfaces of the breasts. It should be noted that, as with the original embodiment, the subject may wear her own brassiere, or a sports type elasticated brassiere, or no brassiere according to her wishes and the professional guidance of the operator helper. It is important that the subject wears a substantial and reasonably close fitting over-garment to limit or prevent any generalized heat loss and the data-logger rests outside this, adjusted so that it rests in a position of comfort on the upper chest just above the breasts. The operator helper depresses the test initiation switch on the data-logger to initiate the test cycle. Subject data collection commences, automatically, after a thirty minute period for temperature equilibration between the subject and the harness. Ambient and body reference temperatures are monitored during the test. At the end of a test period, the data-logger LCD displays the message test finished—upload data. The subject may now doff the over-garment and harness, dress in her normal clothing and leave the test location.

The data-logger and permanently attached harness are returned to the host PC and connected both to the charging port and the data-port, which initiates a diagnostic test on the integrity of the data connection. If the connection is satisfactory, the host PC automatically interrogates the data-logger to identify the test number, uses this to identify the subject record, which is in turn used to open the associated file to which test data are automatically uploaded from the data-logger. Once uploading is complete, the host PC erases the data-logger memory.

Subject test data is evaluated by a person suitably skilled and trained to interpret it and reach conclusions concerning the breast status of subjects. These may vary according to the specific purpose for which the collected data is intended to be used. If the subject requires further investigation, treatment or follow up, she is informed promptly, possibly on the day the test is carried out, especially when strategies need to be implemented urgently. Further investigation may well involve an early retest with the instant system, as well as other tests, to confirm whether or not she may have existing cancer, or the extent of existing cancer, or the optimal time for surgery. It is statistically likely that if the instant test is deployed on a large scale for the assessment of breast cancer risk, the subject population will include women who have the undiagnosed condition. Even when test results indicate no cause for significant concern, this information is desirably communicated to subjects as quickly as possible in order to alleviate or prevent any unnecessary stress. The dedicated program of the host PC incorporates an automatic review and call-back routine by default with interval period parameters constituting one of the system variables.

It will be appreciated that the stringent password and personal identifier security measures introduced in the new and improved embodiment of the instant invention ensure that all reasonable measures have been taken to provide an audit trail for responsibility for data collection, management and interpretation in this potentially life-critical mass screening test.

Accordingly it is a first object of the present invention to provide apparatus capable of making accurate measurements of temperatures on the surface of the human breast, particularly the female breast;

It is a second important object of the present invention to reliably record and store measurements of temperatures on the surface of the human breast;

It is a third important object of the present invention to manipulate and display temperature data collected from the surface of the human breast;

It is a fourth important object of the present invention to provide a method for the assessment of the risk of subsequent development of breast cancer in women who do not currently have the disease;

It is yet another object of the present invention to provide a method for the detection of breast cancer in women;

It is yet another object of the present invention to provide a method for monitoring the effect of intervention strategies on women who have been diagnosed as being at an increased risk of developing breast cancer;

It is yet another object of the present invention to provide apparatus for monitoring a second breast in women who have undergone mastectomy of a first breast for breast cancer.

It is yet another object of the present invention to provide a method for improving the quality of counseling to women considering prophylactic mastectomy of a second and apparently unaffected breast.

It is yet another object of the present invention to provide apparatus for monitoring the breast of a woman with a very large tumor with a view to optimizing the time of intended surgery and for assessing surgical outcomes.

Other features, objects and advantages will become apparent from the specification and drawings in which:

DESCRIPTION OF THE DRAWINGS

Drawings Relating to the Original Embodiment

FIG. 4, is a plan view of four annular contactor pad layers, employed in the construction of two contactor pad assemblies, which are deployed in the harness of the present invention;

Drawings Relating to the New and Most Preferred Embodiment

Figure 11:
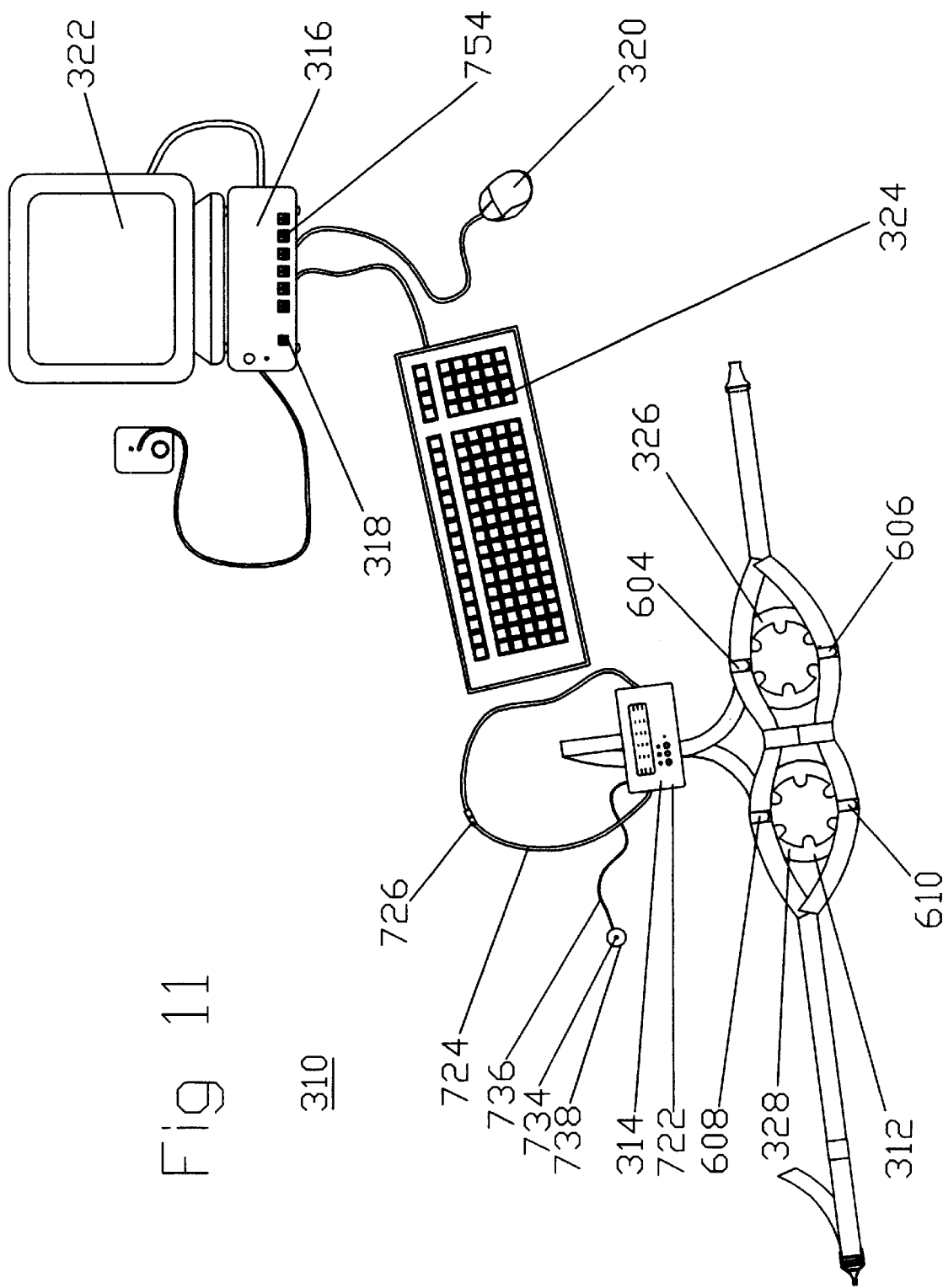
Figure 12:
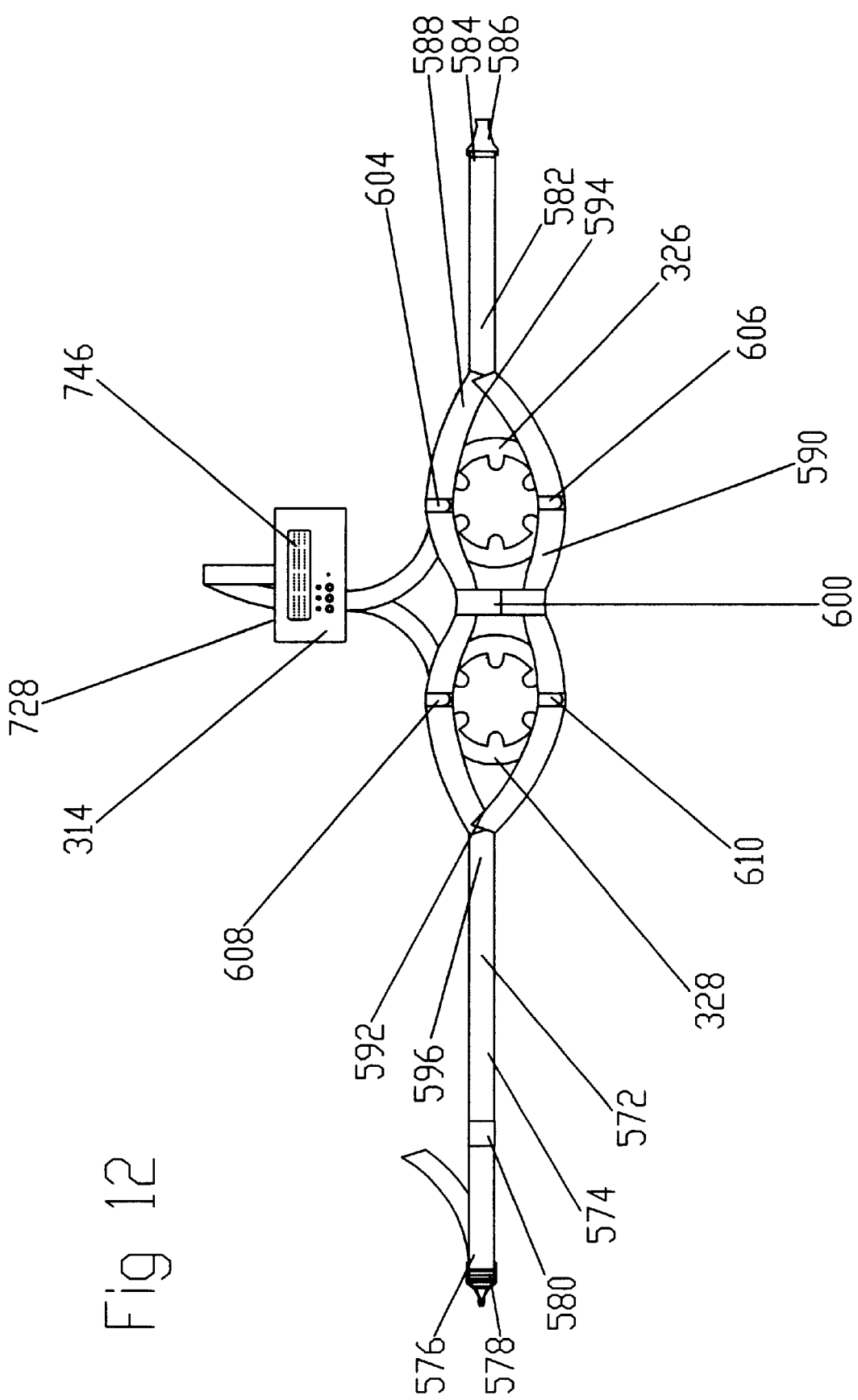
Figure 13:
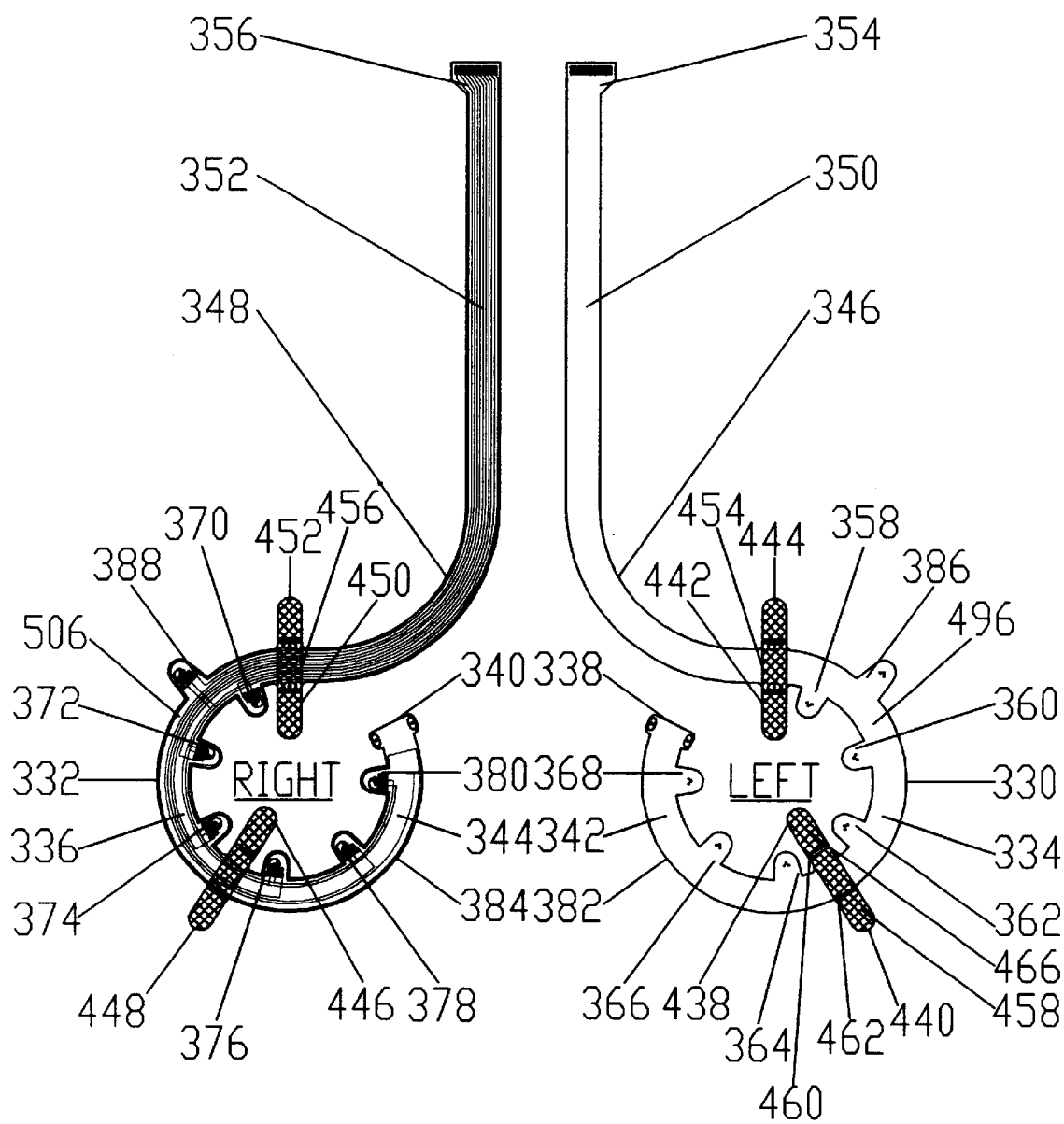
Figure 14:
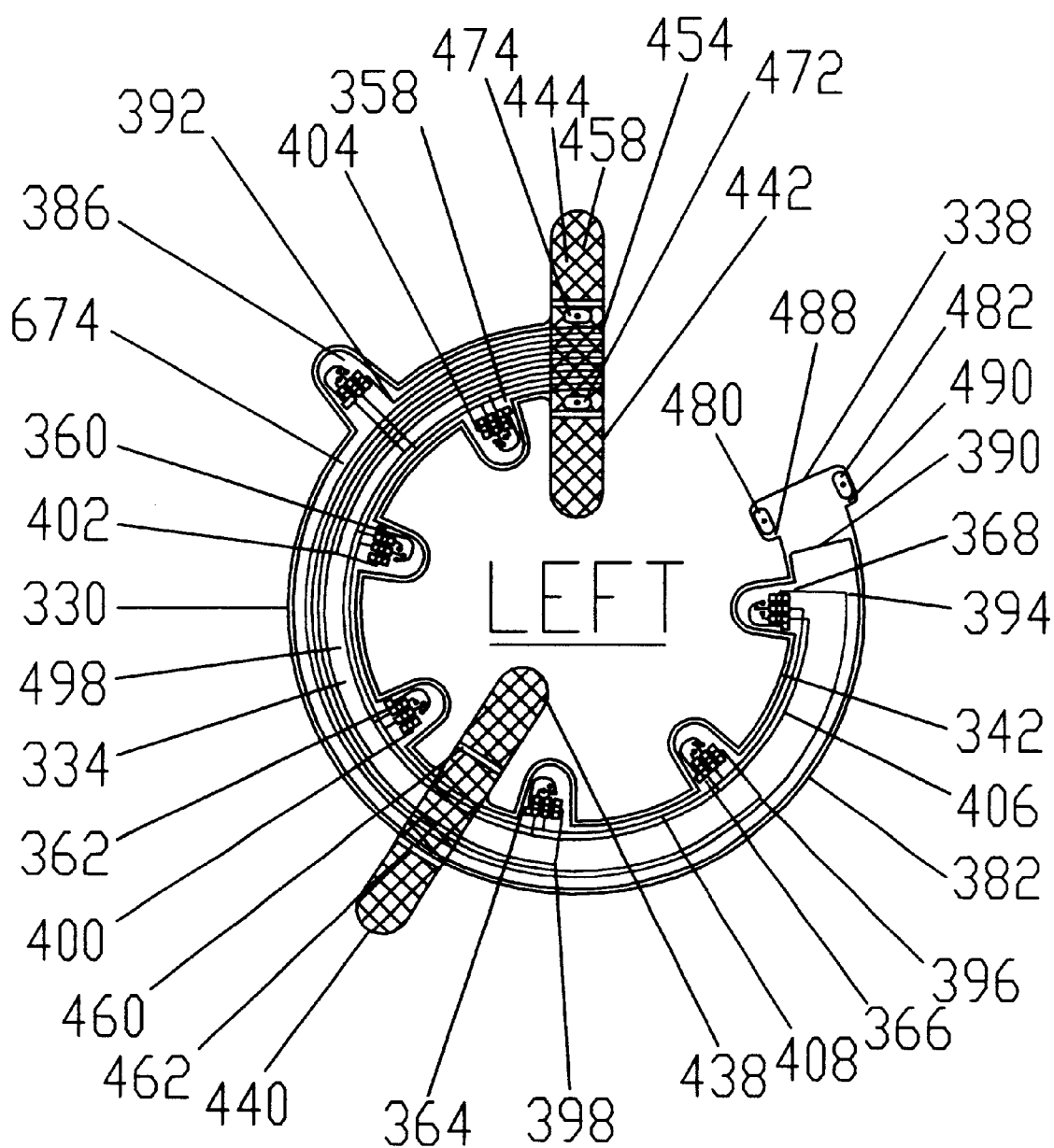
Figure 15:
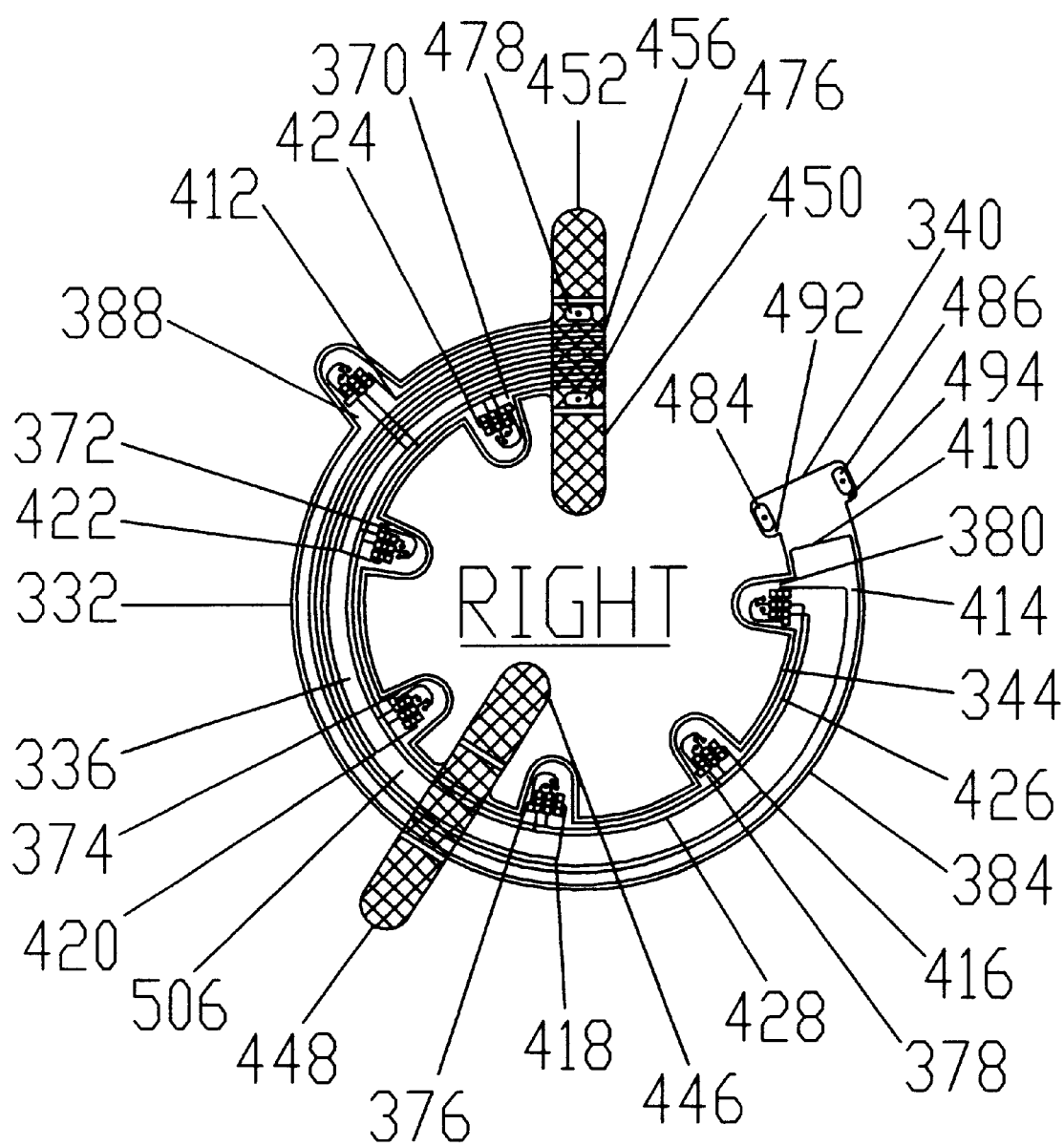
Figure 16:
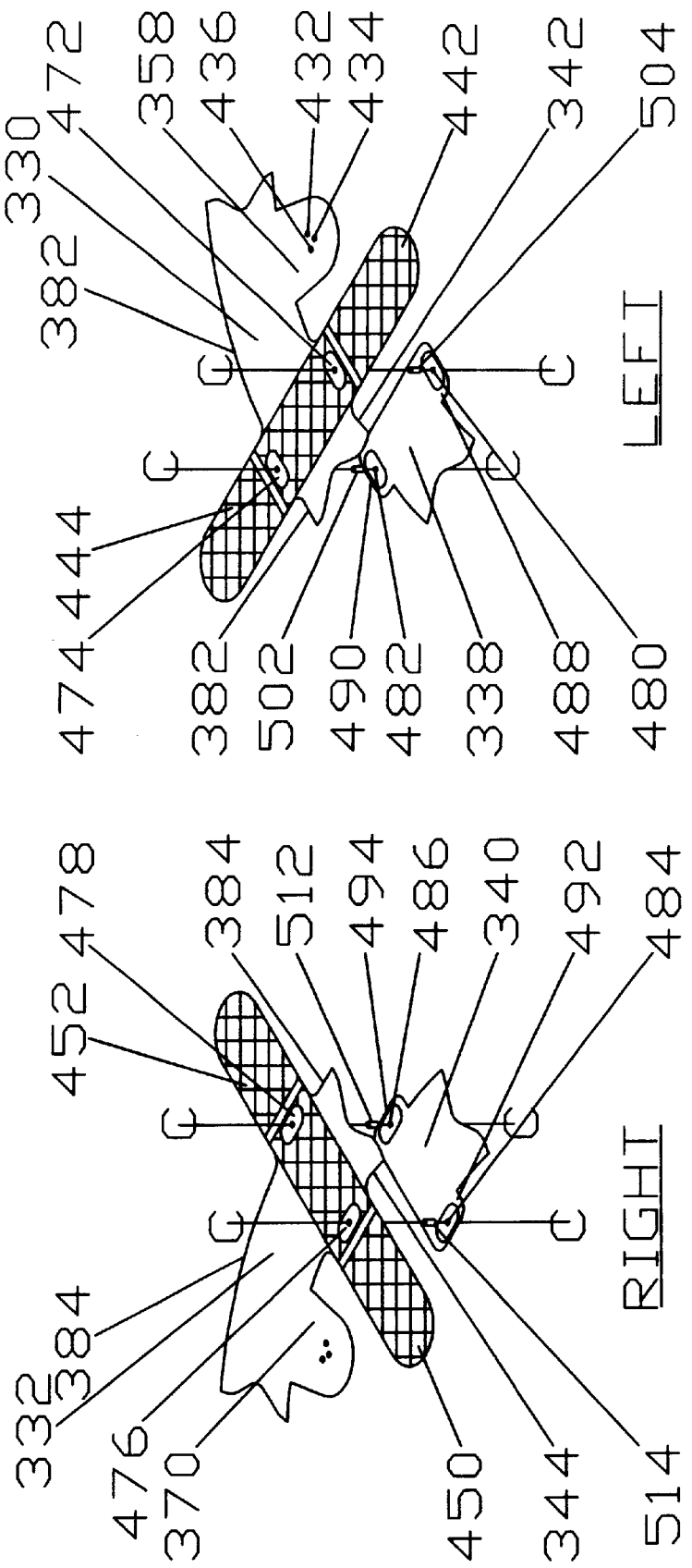
Figure 17:
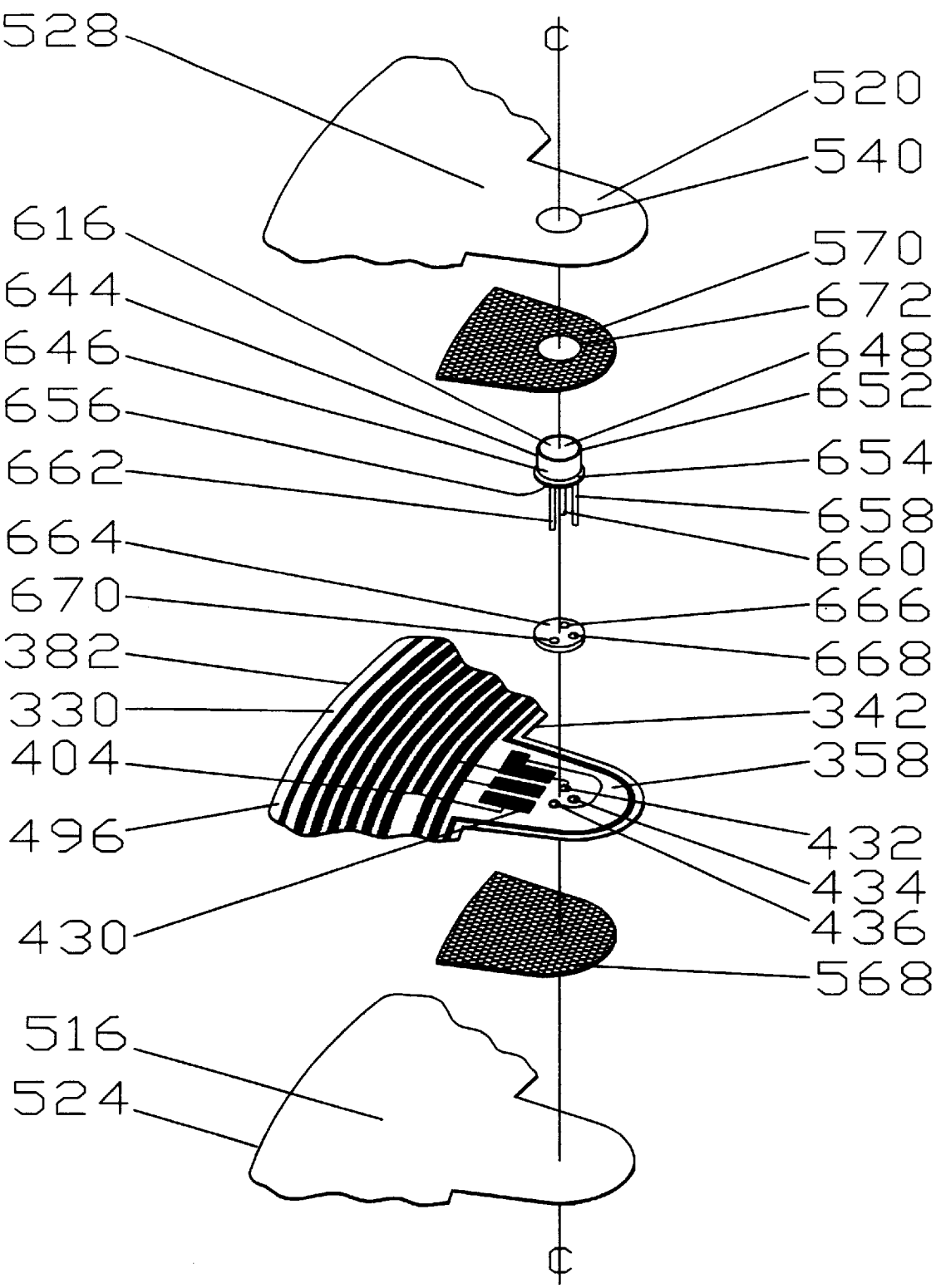
Figure 18:
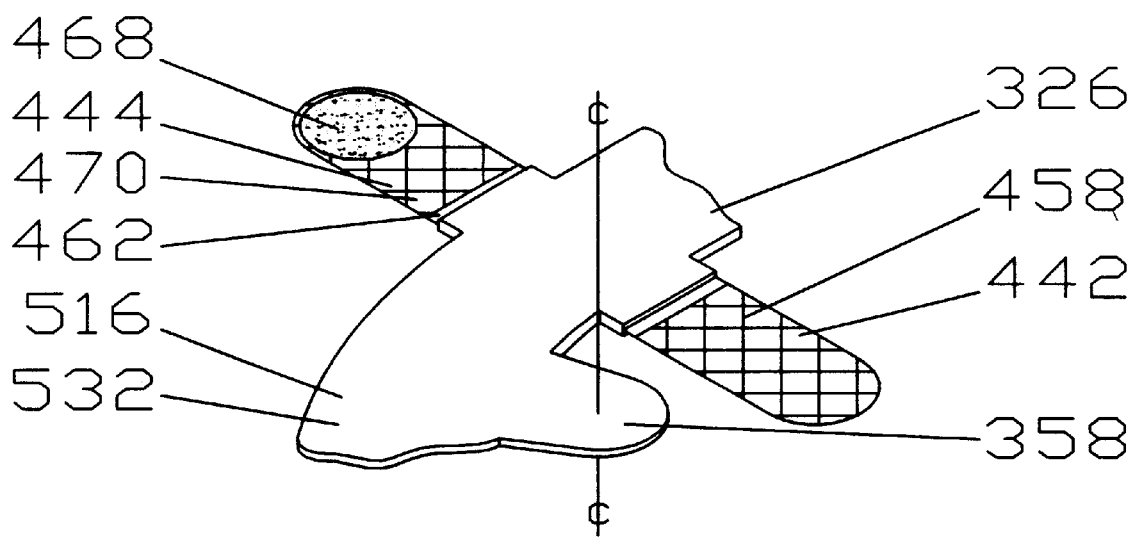
Figure 18A:
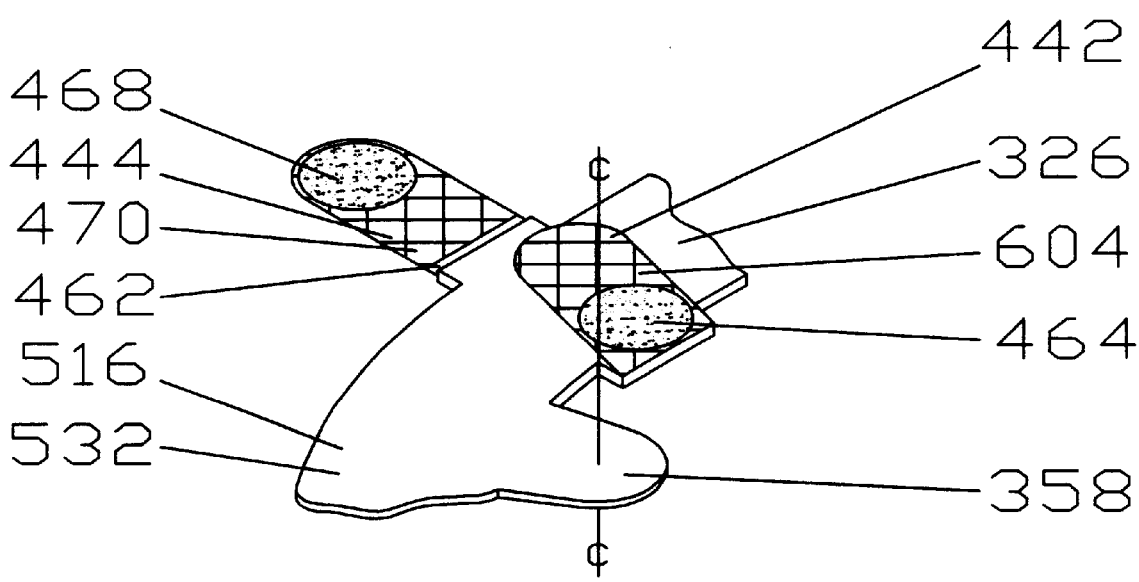
Figure 19:
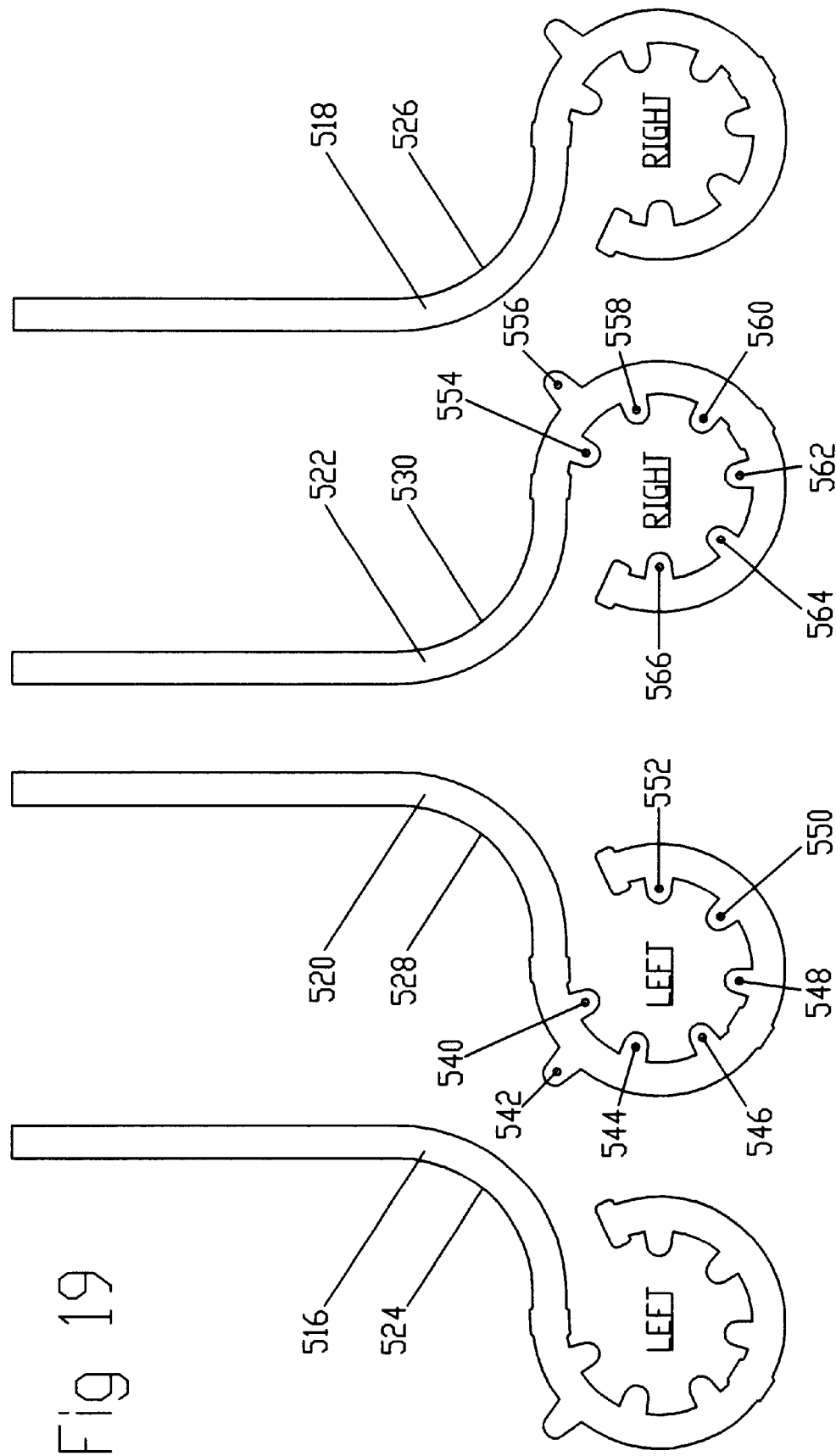
Figure 20:
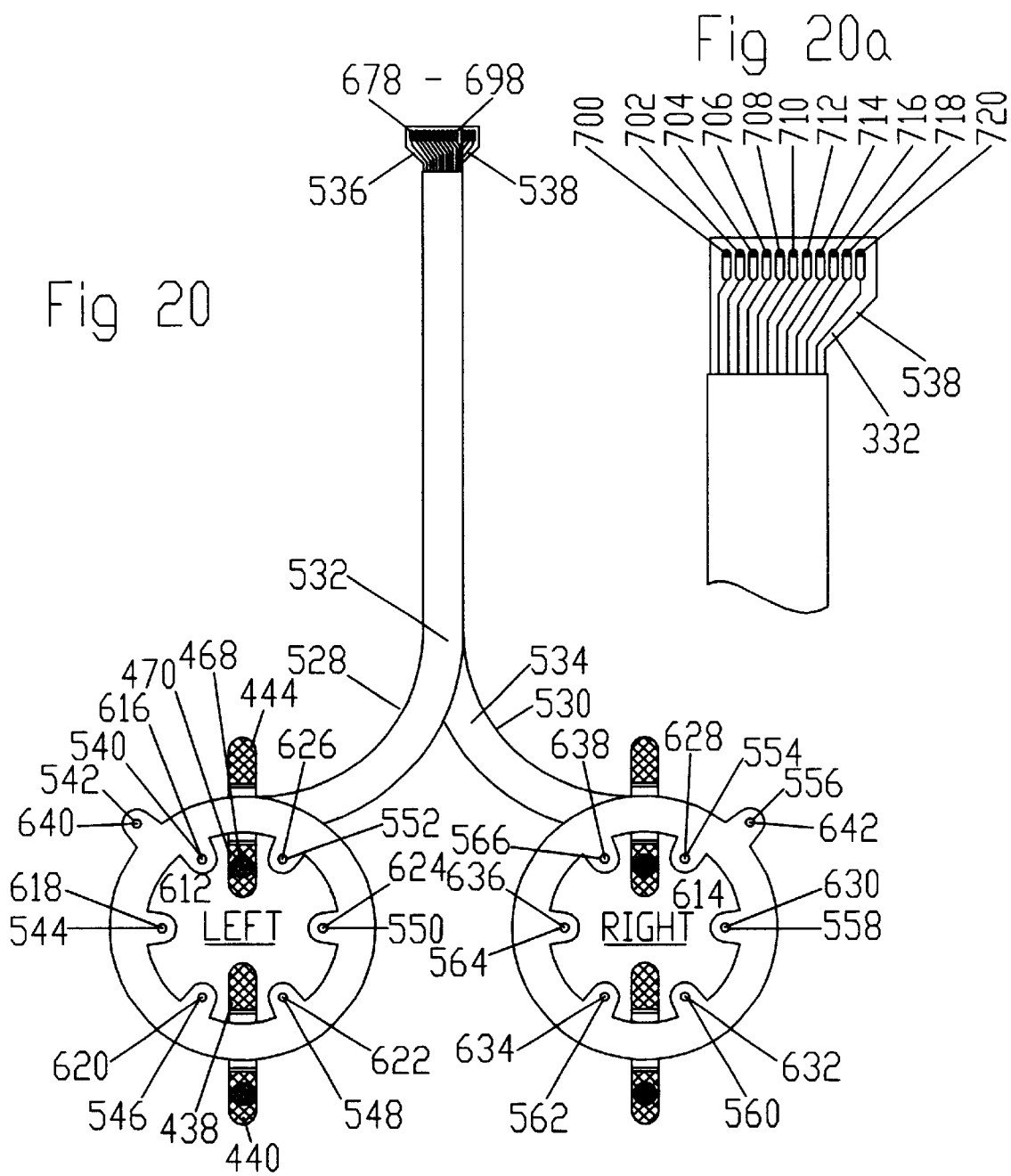
Figure 21:
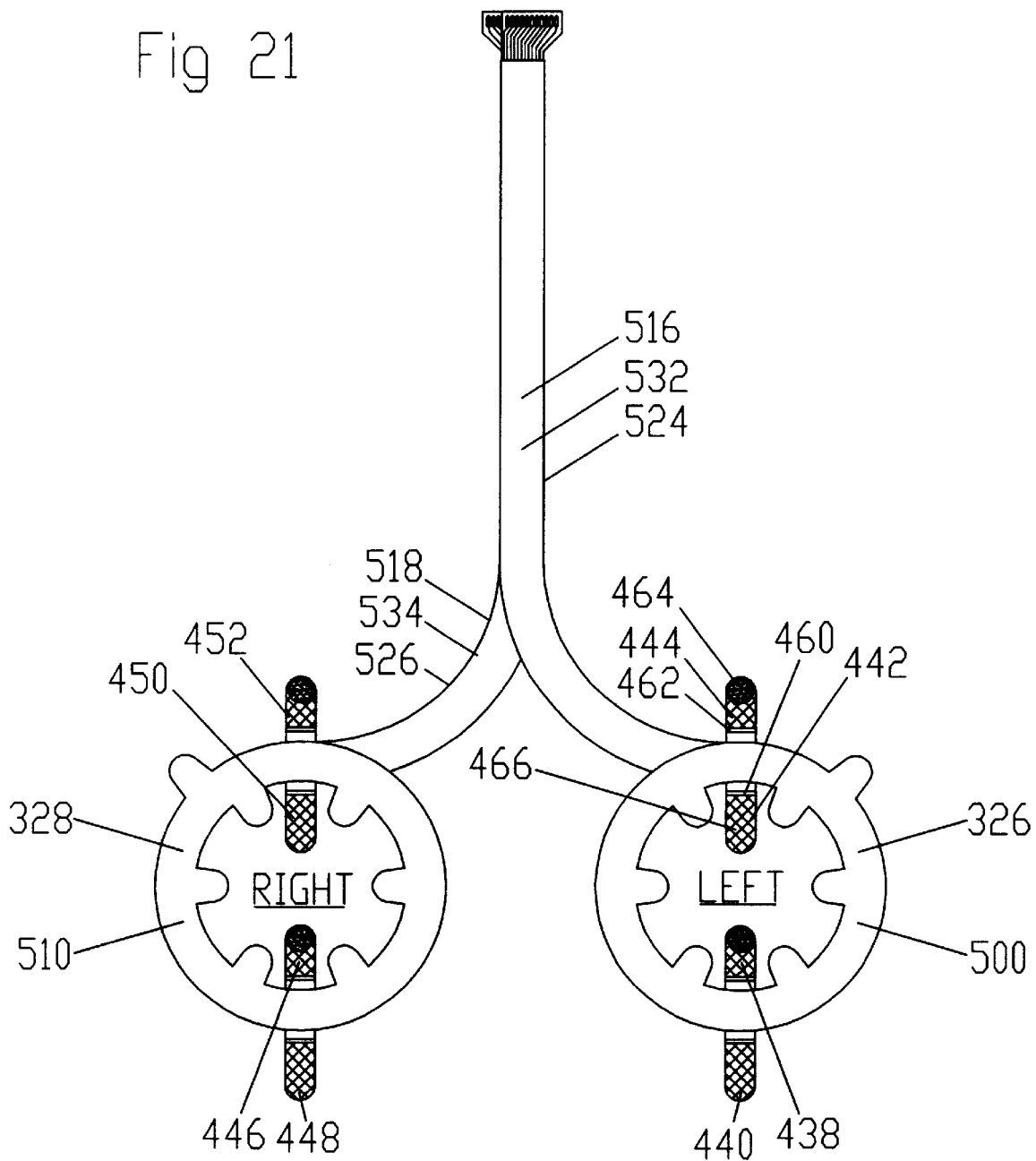
Figure 22:
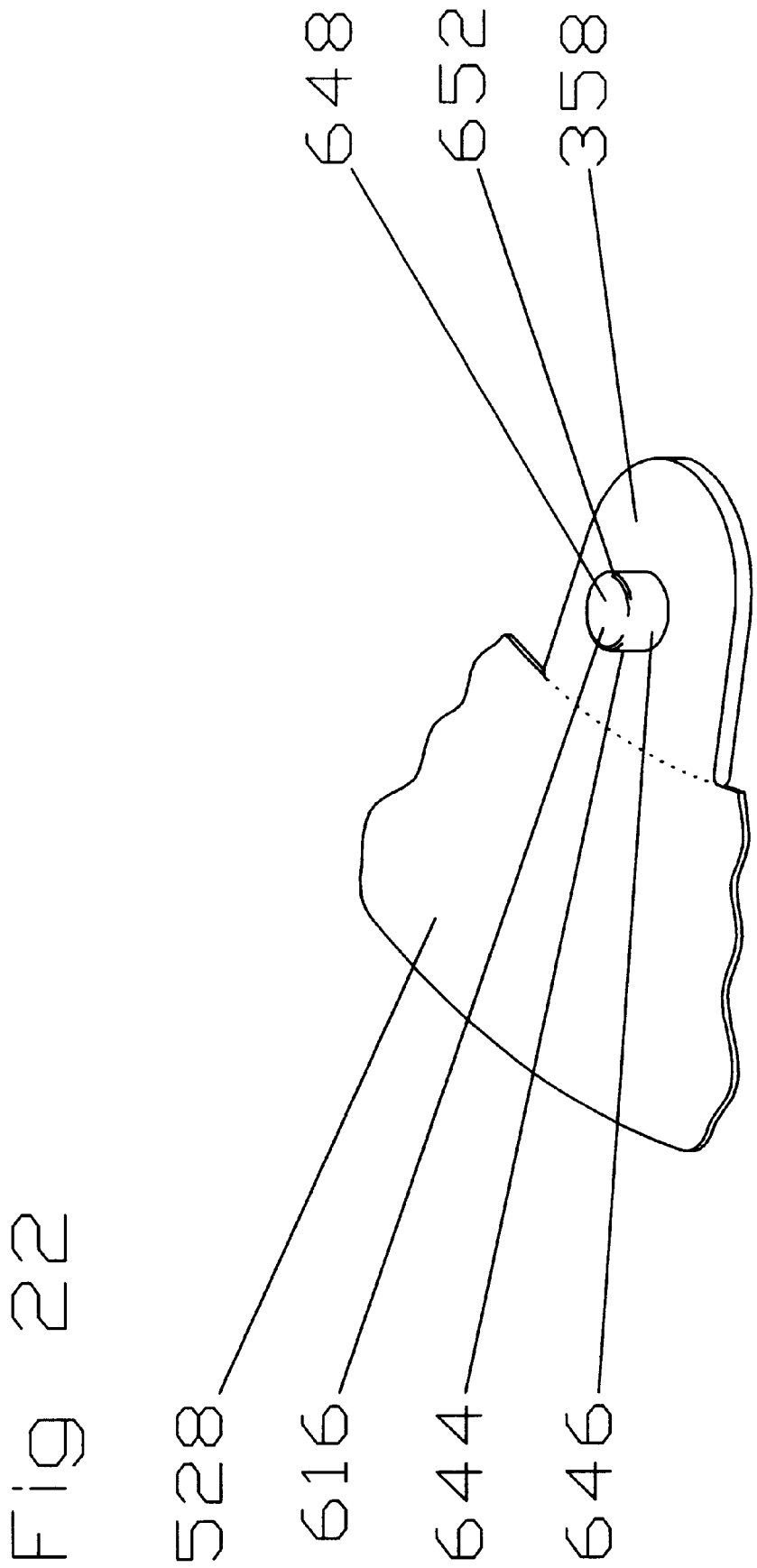
Figure 23:
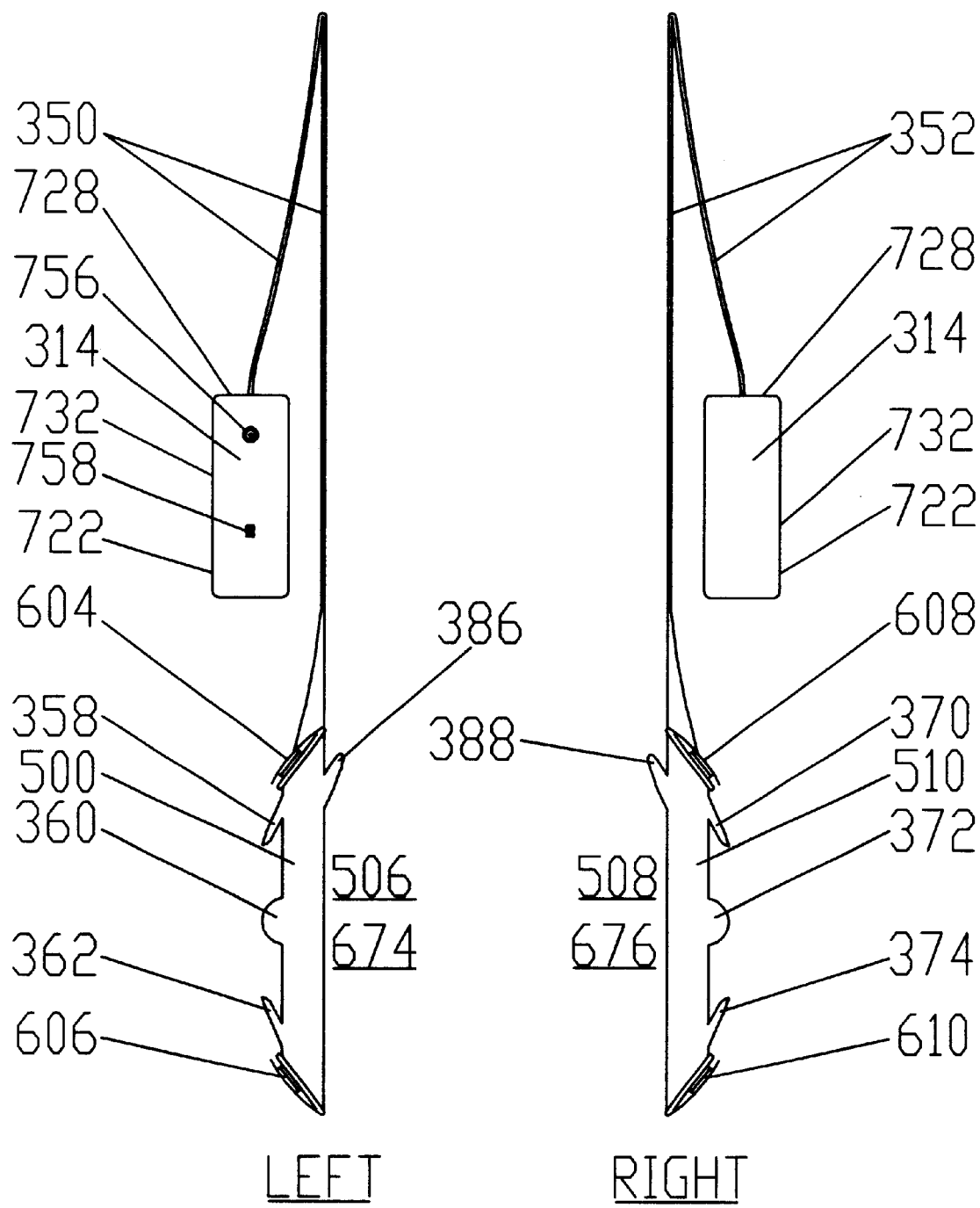
Figure 24:
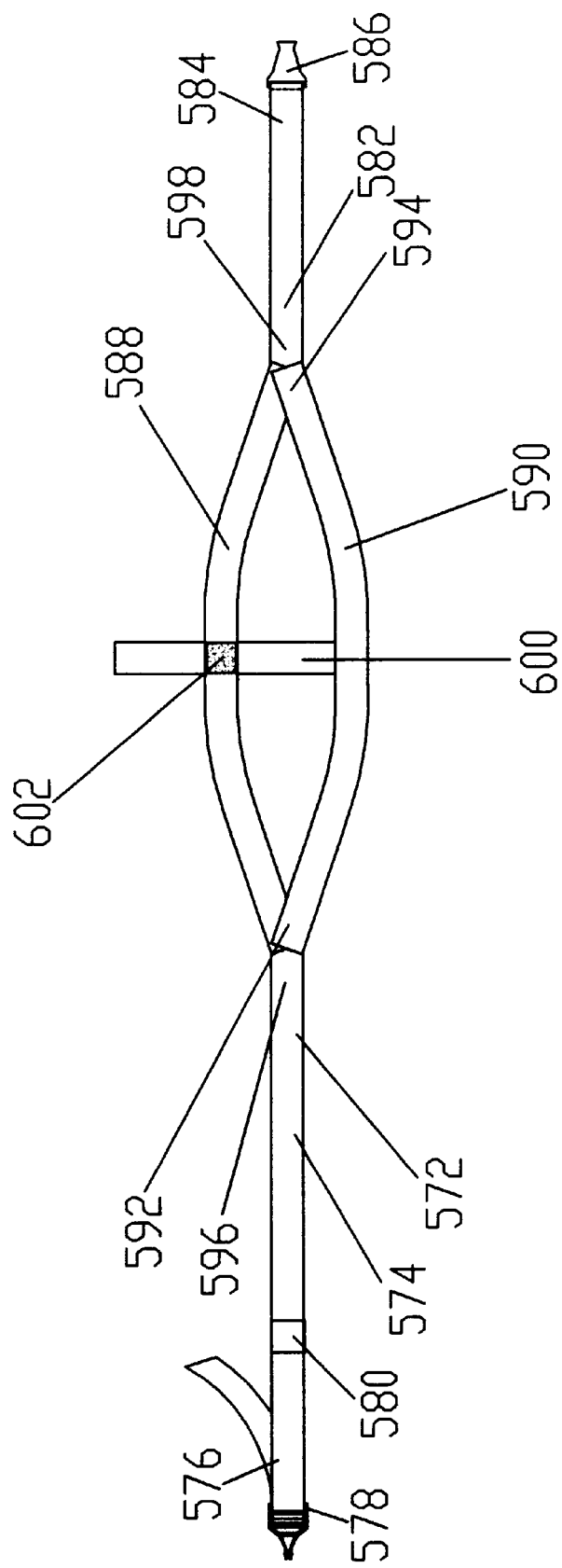
Figure 25:
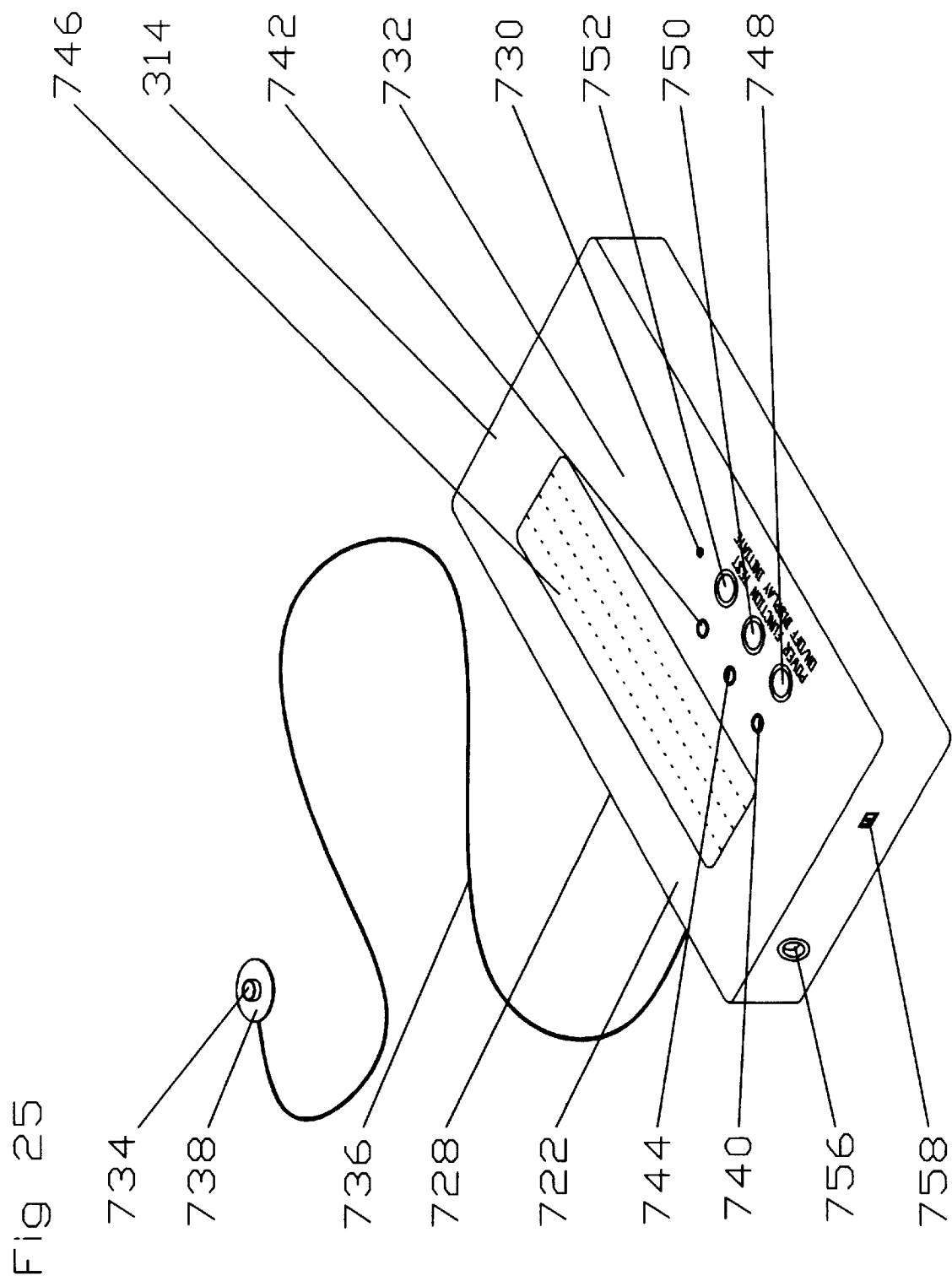
Figure 26:
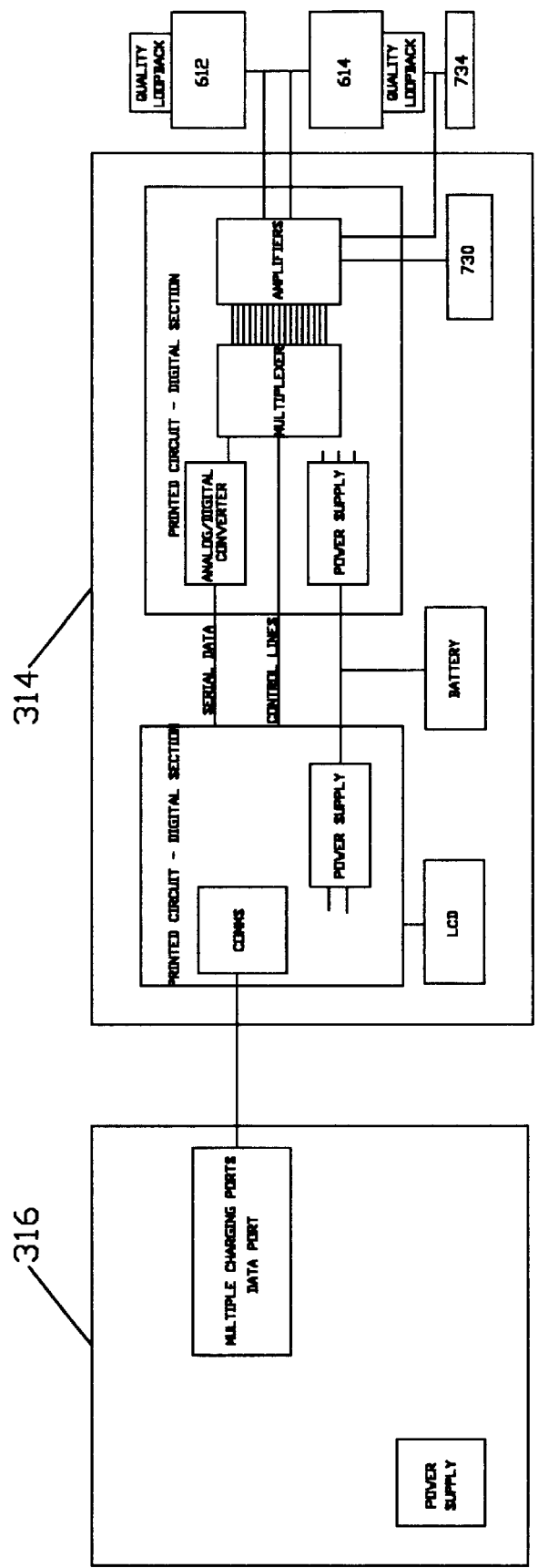
Figure 27:
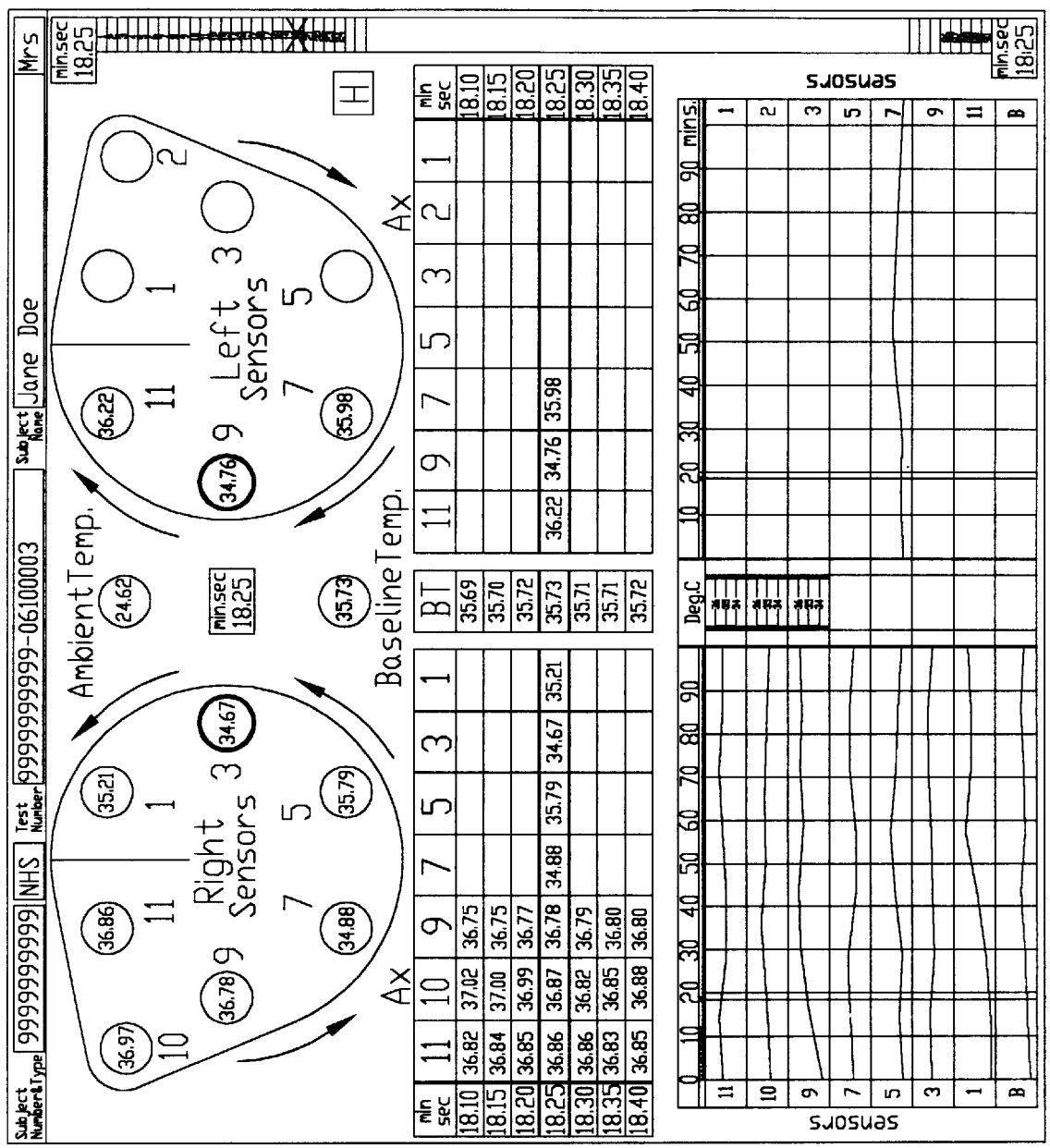

FIG. 11, is a diagrammatic perspective view indicating the principal elements of the system of the new and most preferred embodiment of the instant invention;

FIG. 12, is a diagrammatic view of a new and most preferred embodiment of harness means and data-logger means, showing the outward-facing surface of the harness;

FIG. 13, is a front outward-facing view of two thin, flexible, printed circuit boards deployed in left and right orientation, for a left and right breast, in the construction of two contactor pad assemblies forming part of the harness;

FIG. 14, is an enlarged rear, or breast-facing view of a first, substantially circular portion of a flexible printed circuit board deployed in left orientation for a left breast;

FIG. 15, is an enlarged front or outward-facing view of a first, substantially circular portion of a flexible printed circuit board deployed in right orientation for a right breast;

FIG. 16, is a partial perspective view indicating assembly details for assembling left and right frustum breast accommodating structures formed from right and left oriented printed circuit boards;

FIG. 17, is an exploded perspective view of sensor means and primary tab means of a contactor pad assembly;

FIGS. 18 and 18a, are perspective views of folded flap means of a contactor pad assembly, comprising secondary tab means;

FIG. 19, is a front view of left and right elements of attachable cleanable covering means for frustum contactor pad assemblies;

FIG. 20, is a rear, or breast-facing view of the temperature sensing surface of a complete assembly of two covered frustum contactor pads;

FIG. 20a, is an enlarged detail of data-logger connecting means of one contactor pad assembly of FIG. 19;

FIG. 21, is a front, or outward-facing view of the non temperature sensing surface of a complete assembly of two frustum contactor pads;

FIG. 22, is a perspective view of a detail of an assembled contactor pad, according to the new and most preferred embodiment, showing a primary tab and a single sensor;

FIG. 23, is a pair of side views of contactor pads, for a left and right breast, connected to data-logging means according to the new and most preferred embodiment;

FIG. 24, is a front flat view of a body strap assembly of the harness;

FIG. 25, is a front perspective view of a data-logger and body reference temperature sensing means;

FIG. 26, is a block circuit diagram of data-logging means, according to the new and most preferred embodiment;

FIG. 27, is a diagrammatic representation of a screen print, produced on a visual display unit (VDU) by a dedicated computer program, showing a graphical and numerical representation of breast surface temperature data produced.

DETAILED DESCRIPTION OF THE INVENTION AND METHOD OF USE

With general reference to FIGS. 1–10, there is provided an original embodiment of a system 10, which allows breast surface temperatures to be measured, with great reliability, for periods of one and a half hours, or more, at any desired rational sampling rate. Collected breast surface temperature data may then be downloaded into a computer, which forms part of the system, for elaboration using proprietary software which is also part of the system.

With general reference to FIGS. 11–27, there is provided a new and most preferred embodiment of improved system 10.

Original Embodiment

In the original embodiment, system 10, comprises the principal elements of a mechanical adjustable harness 12, having a permanently connected remote monitor unit 14, an interface unit 16 and a host personal computer (PC) 18. Host PC 18, comprises a normal processor, VDU, mouse and keyboard (not illustrated).

It is important to note that mechanical adjustable harness 12, is not physically attached to the breast with adhesives or tape. Neither is harness 12, a brassiere, since it cannot provide support for the breasts and does not contain them, nor is it a brassiere insert since it is not necessary to use it in conjunction with a brassiere. Finally, harness 12, is not a garment, since it has no purpose or use as apparel and is used only in relation to its specific function, immediately hereinafter described.

System 10, is directed, by means of the function of its structural elements, towards the assessment and determination of the risk of developing cancer later in life, by the measurement of breast temperatures over a period normally of one and a half hours. Notwithstanding this, the instant invention may be used to detect breast cancer.

Harness 12, only one size of which is needed to fit almost all subjects, comprises two flexible, flat, ring-like or annular contactor pads 20 and 22, united anteriorly by a short, adjustable, elasticated strap 24 and united posteriorly by a longer, adjustable and openable strap 26. Harness 12, may be used without a brassiere or in conjunction with the subject's own brassiere, if she indicates that she is discomforted without a supporting undergarment, according to the decision of the investigator. Each annular contactor pad 20; 22, comprises substantially similarly sized and shaped inner and outer layers 28; 30 and 32; 34, of flexible, compressible and extensible material preferably neoprene sheet 2.5 mm to 3.00 mm in thickness and provided with suitable flexible facing fabrics, such as the nylon material known commercially as Lycra™.

Each of annular contact pad layers 28–34, has two extension tabs 36–50, disposed about opposite ends of a diameter, for the attachment of anterior strap 24, and posterior strap 26. Contact pad layers 28; 30 and 32; 34, which are cut-out blanks, each have a central hole 52–68, preferably of 40 mm of diameter prior to assembly. During assembly, hereinafter described, this diameter increases to about 45 mm, which is adequate to accommodate the areolar area of the majority of women. The outer diameter is preferably 100 mm before assembly and this decreases minimally upon assembly.

Annular contactor pad layers 28–34, are laid one over the other, in pairs, for sewing, such that extension tabs 36–50, are aligned. By way of example, with particular reference to FIGS. 6 and 7, contact pad layers 28; 30, would be laid one over the other, aligned and then stitched together around the circumferences of central hole 52; 54. This is preferably accomplished with a zig-zag sewing machine set to a relatively large stitch and relatively low tension. The general appearance of the stitching is represented at 60. With some care and practice it will be found by those skilled in the art, but not this novel technique, that the annular contactor pad layers, for example 28 and 30, may be pulled together in such a manner that the facings, two of which are indicated at 62 and 64, oppose at a join lying centrally between them, such that the neoprene itself is not exposed. This novel arrangement, together with other measures described hereinafter, imparts a pleasing 'bulked' feel to the construction of annular contactor pads 20 and 22.

Eight sensors 66–80, are arranged as two arrays 82 and 84, each of four sensors 66–72 and 74–80, respectively, on each of the inner contacting surfaces 86 and 88, of annular contactor pads 20 and 22, respectively Sensor arrays 82 and 84, are disposed about inner contacting surfaces 86 and 88, in a regular manner, 90° apart along the circular center lines 90 and 92, lying between inner and outer boundaries 94; 96 and 98; 100, of 20 and 22, respectively. If, for reasons of explanation only, the upper portion of the vertical mid-line of each breast is regarded as North, the sensor positions are at North-East, South-East, South-West and North-West. By virtue of this arrangement, sensing means are provided to each of the well recognized anatomical quadrant of the breasts.

Sensors 66–80, are of the type AD590 supplied in a transistor can package of the generic type TO-92 and described in more detail, hereinafter.

Figure 5:
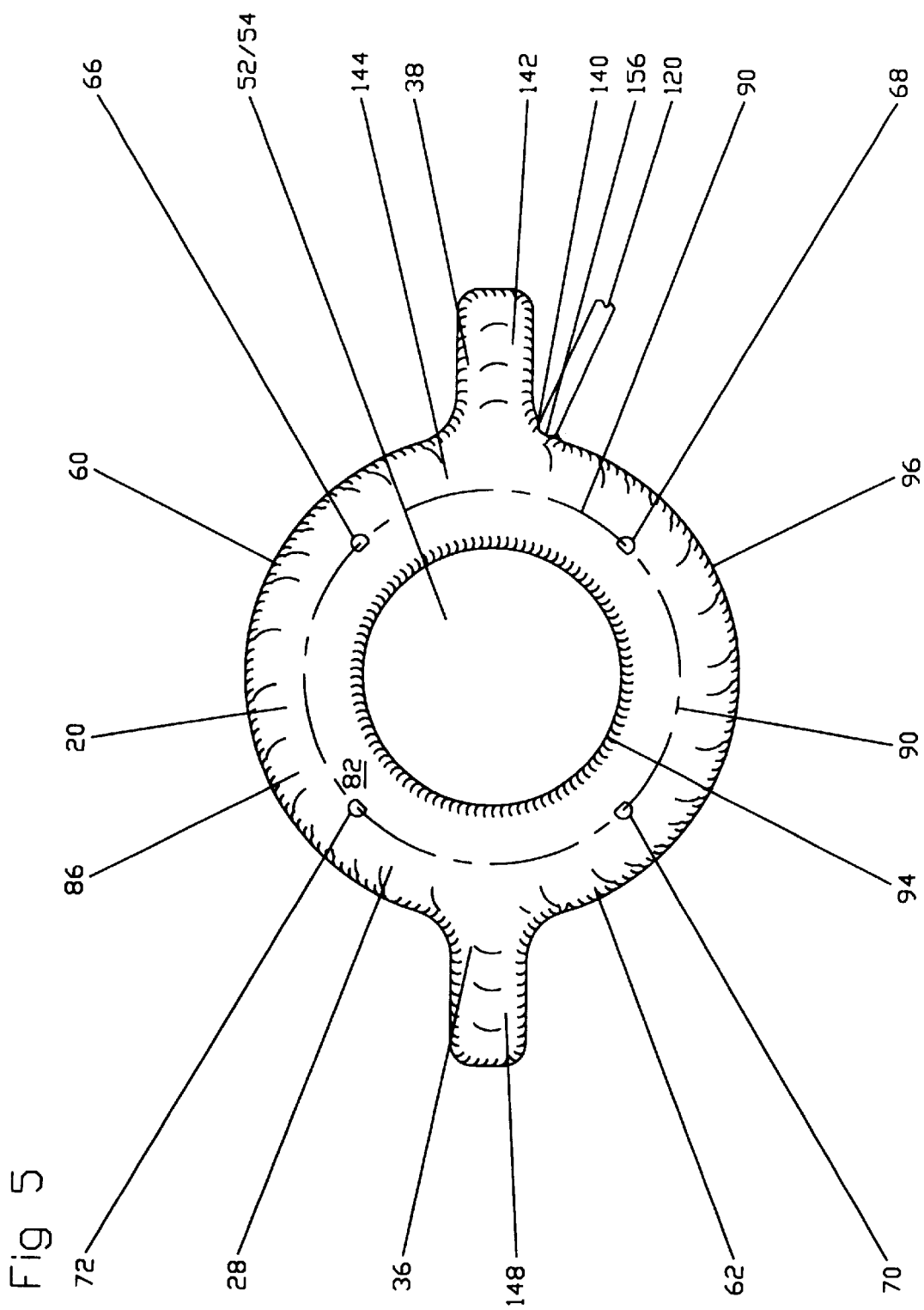
FIG. 5, is a plan view of the surface of one annular contactor pad assembly, according to the present invention, showing a thermal sensor array.
Figure 6:
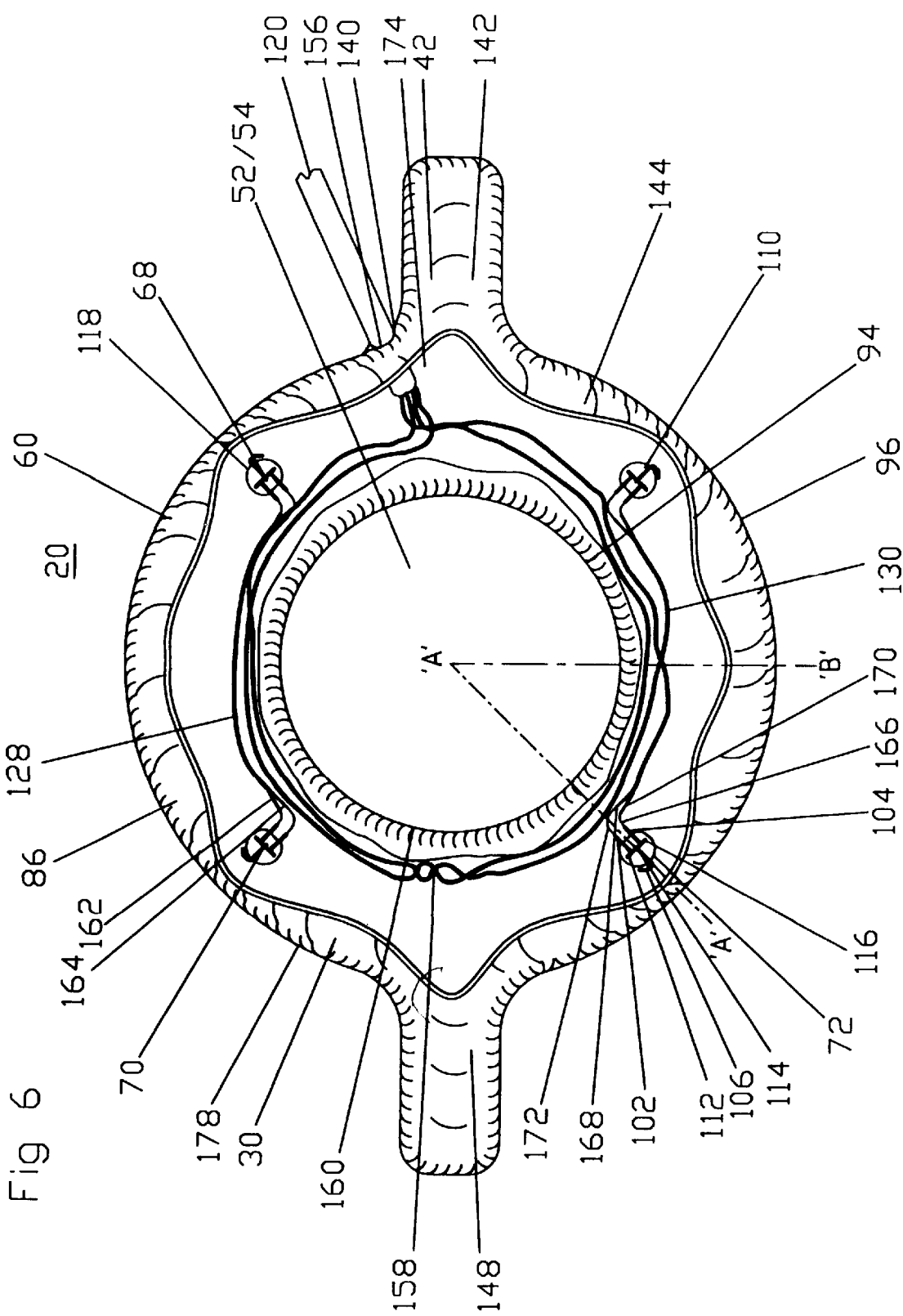
FIG. 6, is a cut-away plan view of one annular contactor pad assembly, from the outside or non-contact surface, showing sensor securing means and wiring arrangements.
Figure 6A:
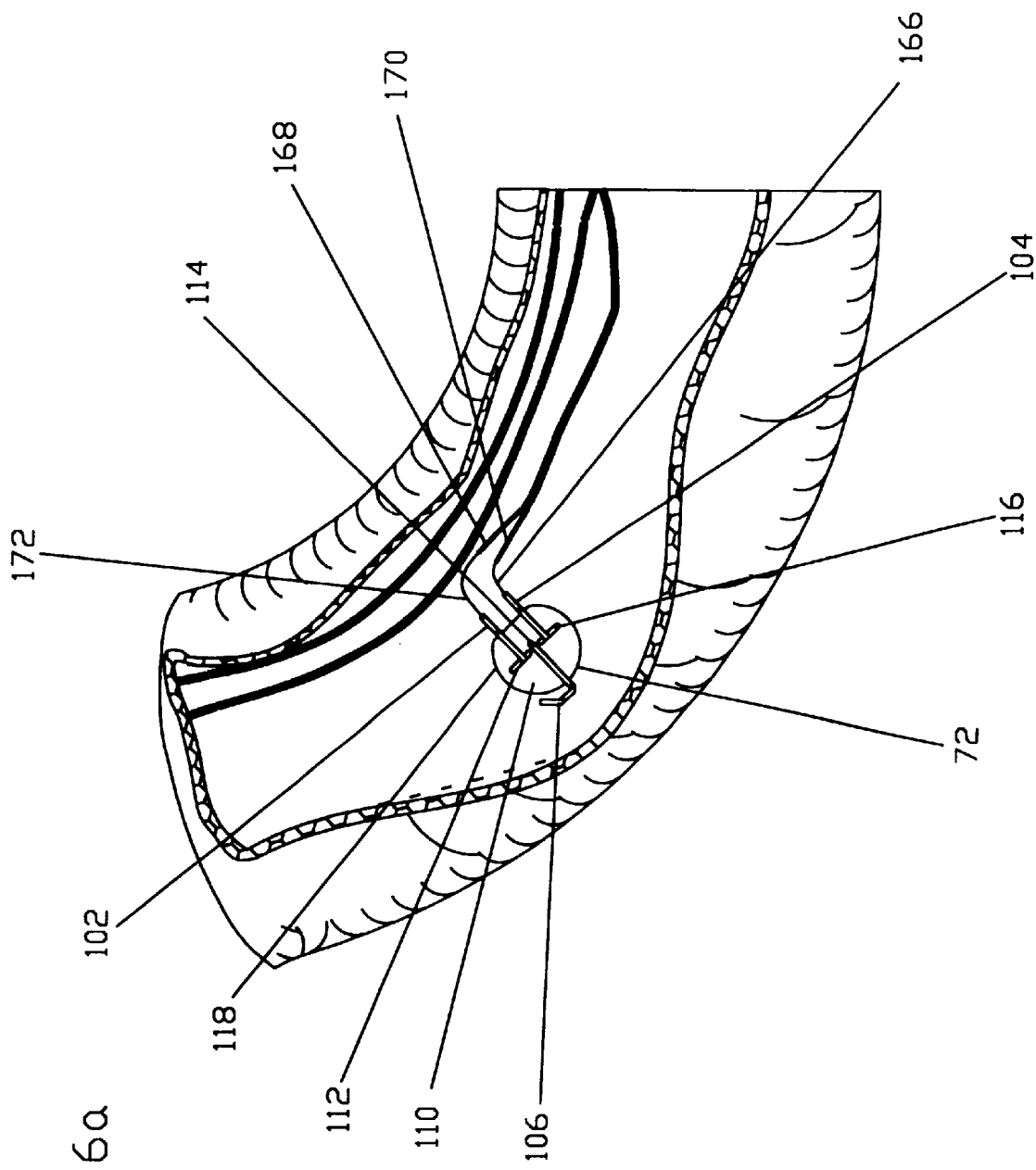
FIG. 6a, is an enlarged portion of FIG. 6, showing more clearly the wiring arrangements for sensor means.
Figure 7:
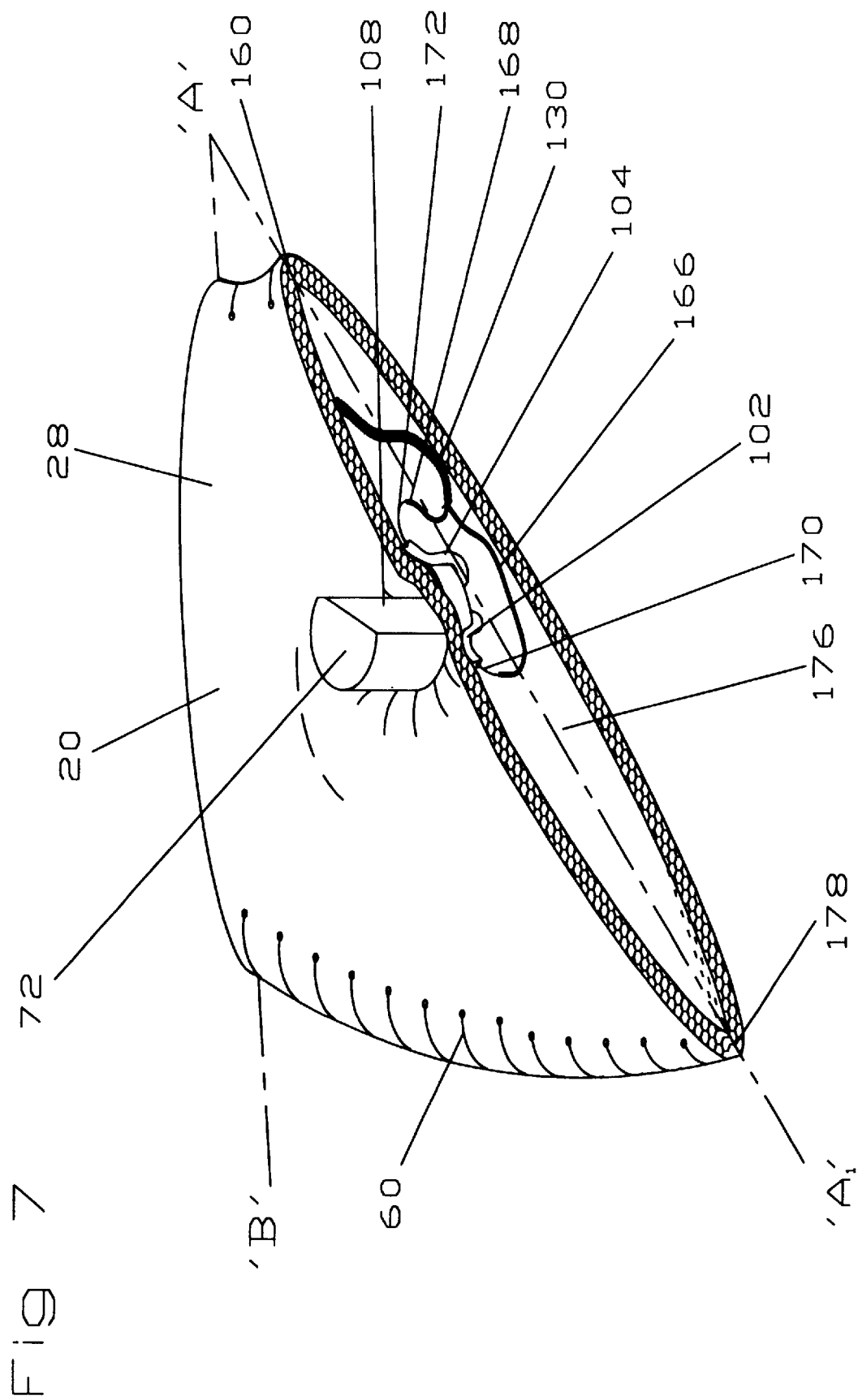
FIG. 7, is a partial, perspective, pseudo-section view of a segment of a contactor pad assembly, along line $A_1$–A and $A_1$–B showing construction details, a sensor and capture means therefor.
Figure 8:
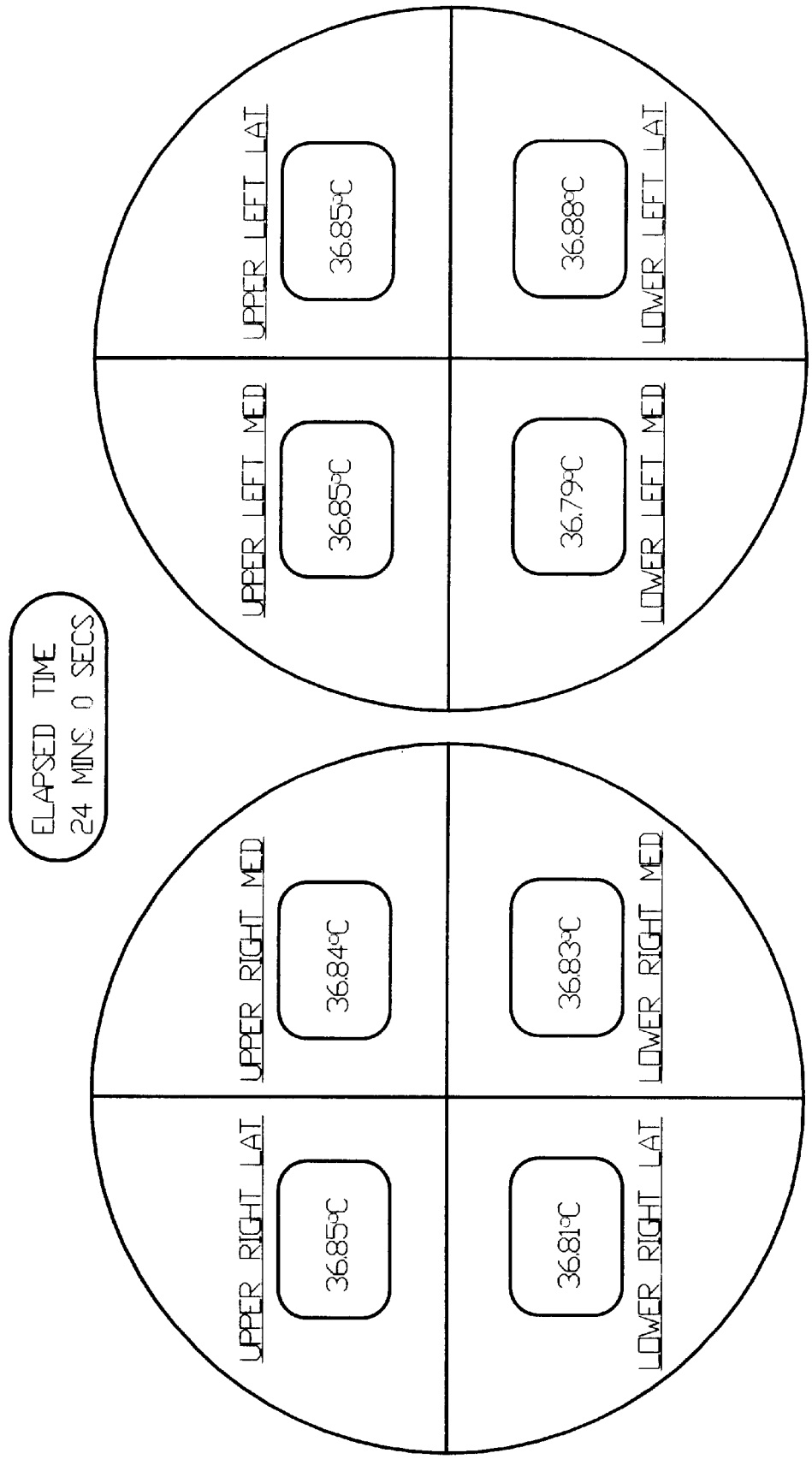
FIG. 8, is a diagrammatic view of a screen print, produced on a visual display unit (VDU) by a dedicated computer program, showing a pictorial and graphical representation of breast surface temperature data produced according to the present invention.

The method of deployment of sensors 66–80 and novel features of the associated wiring will be described with particular reference to FIGS. 5, 6 and 7, especially in respect of sensor 72. Each of sensors 66–80, has three stiff fine wire legs each about 1 mm wide, 0.5 mm thick and 10 mm long, closely disposed, 120° apart, those of sensor 72, being indicated at 102, 104 and 106. Each of legs 102, 104 and 106, is pushed carefully and firmly right through the material of inner annular contactor pad layer 28. Advantage is taken of the small dosed cell structure of the neoprene material which effectively renders the punctures of the material self-sealed by close compressive contact against each of legs 102, 104 and 106. All faces of type TO-92 sensor can package 108, are active and this is completely unsheathed, having no covering of any kind. This is in order to maximize contact with the breast surface and thermal transfer.

When correctly assembled to inner annular contactor pad layer 28, legs 102, 104 and 106, of can package 108, protrude through the neoprene, and engage a small disc-like molding 110, adapted by the provision of through holes 112, 114 and 116, disposed 120° apart near its periphery 118, to receive each of them, respectively. Disc molding 110, is slightly larger than can package 108 and this causes legs 102, 104 and 106, advantageously to splay somewhat (not shown). By gently compressing disc molding 110 and can package 108, together, against the neoprene of inner contact pad layer 28, the available length of legs 102, 104 and 106, protruding through holes 112, 114 and 116, in disc molding 110, may be extended. Legs 102, 104 and 106, may then be bent over at periphery 118, of disc molding 110, providing initial securing means for this assembly. As previously indicated, this method of introduction and assembly is applied to all of sensors 66–80, of both annular contactor pads 20; 22.

Cable connecting means between sensors 66–80, and monitor unit 14, are in the form of light, flexible plastics sheathed outer cables 120 and 122, each provided with four twisted pairs of inner cables 124–130 and 132–138, the number of pairs being the same as the number of sensors provided on each contactor pad. For reasons of clarity, it has been necessary to exaggerate the size of inner cables 124–130 and 132–138, in FIGS. 6 and 7.

A different color outer is used for each of sheathed outer cables 120 and 122. This is to serve an important convention, during use, according to which the same first color is always used for the sheathing outer of the cable serving the left breast and similarly the same second color is always used for the sheathing outer of the cable serving the right breast. In the preferred embodiment we have used gray for the sheathing outer of the cable serving the left breast and violet for the sheathing outer of the cable serving the right breast, however, the important point is that the color difference must be obvious.

Sheathed outer cable 120, is secured, ultimately, in the angle 140, formed between extension tab 142 and the main body portion 144, of annular contactor pad 20, emerging along a generally medial path between layers 28 and 30. Similarly, sheathed outer cable 122, is secured, ultimately, in the angle 146, formed between extension tab 148 and the main body portion 150, of annular contactor pad 22, also emerging along a generally medial path between layers 32 and 34.

Extension tabs 142 and 148, provide anchor points for first and second ends 152 and 154, respectively, of adjustable, elasticated strap 24. First and second ends 152 and 154 of adjustable, elasticated strap 24, are secured in place by sewing.

Wiring details will be described with particular reference to FIGS. 6 and 7 and especially contactor pad 20. However, it is to be noted that wiring routing is accomplished according to a novel strategy directed towards ensuring that individual sensors are never subjected to traction in normal robust use. In particular, connections to those sensors which lie medially namely 66 and 68, in the case of contactor pad 20, are closest to the point of entry/emergence 156, of sheathed outer cable 120, in angle 140. Connections to sensors 66 and 68 are provided by twisted pairs 124 and 126, of sheathed outer cable 120, from which a sufficient length of sheathing is stripped away to allow them to be extended, in opposite directions, right around inner surface of inner sewn seam 160, disposed between annular contact pad layers 28; 30 and about central hole 52/54, before being routed back to sensors 66 and 68. At the point furthest away from point of entry/emergence 156, twisted pairs 124; 126, are twice passed under and over one another, indicated at 158 and then drawn gently against the inner surface of seam 160, in such a manner that the tension applied does not cause distortion of central hole 52/54.

The restraint provided by routing twisted pairs 124 and 126, 'out and back' and by doubly overlapping them, before redirecting them to sensors 66 and 68, together with other measures shortly hereinafter described, provides such a high level of protection against traction on the sensors that it is not necessary to apply this strategy to remaining two twisted pairs 128 and 130, which are connected to sensors 70 and 72, which although furthest away from point 156, are shorter The routing strategy may, however, be applied to twisted pairs 128 and 130, in full or in part, if so desired.

Sensor connection details will be described with particular reference to sensor 72. In FIG. 6, it may be seen that, by way of example, twisted pairs 128 and 130, each have a short section untwisted to provide single line connecting portions, indicated at 162; 164 and 166; 168, for sensors 70 and 72, respectively. As may be seen with brief reference to FIG. 7, very short bare wire ends, indicated at 170; 172, are provided on each of 166;168, respectively. Bare wire ends, 170; 172, are soldered to legs 102 and 104, respectively of sensor 72, leg 106, not being required in the circuitry employed.

Insulating means, which are also flexible cushioning means and adhesive means, are in the form of a hot melt insulating and sealing compound, such as that supplied by Messrs Bosch AG, Germany, which is soft-setting and also translucent when initially cured. With contactor pad layer gathered and held clear, the compound is introduced intimately about sensor legs 102–106, and soldered bare wire ends 170 and 172. This process is repeated for all sensor connections on both contactor pads 20 and 22. The process is extended by spreading a layer, several millimeters thick, over and about twisted pair connecting wires 124–130, and then, all over the interior of contactor pad layer 28. Particular attention is paid to the area about and around the inside of seam 160, about central hole 52/54. Annular contactor pad layer 30, is the released and the compound applied carefully in the area indicated at 174, in FIG. 6, where sheathed outer cable 120, upon sewing, comes to lie within the outer margins 96 and 100, of annular contactor pad layers 28; 30. The compound mass is indicated at 176, in FIG. 7. At a point when compound 176, has begun to cure but is still generally extrudable, annular contact pad layers 28; 30, are pressed together and then sewn around outer margins 96 and 100, to form outer seam 178, in a manner substantially similar to that hereinbefore described with reference to seam 160, of central hole 52/54. When constructed with the materials and assembled according to the method immediately hereinbefore described, annular contactor pads 20 and 22, are soft, flexible and formable and have a pleasing, compressible, 'bulked' feel.

Completed annular contactor pad assemblies 20 and 22, are 'handed' left and right by virtue of differently colored sheathed outer cables 120 and 122, each being directed medially. Annular contactor pad assemblies 20 and 22, are fitted with a short elasticated and adjustable anterior strap 24, by sewing respective first and second ends 152; 154, thereof, to medially directed tabs 142 and 148, respectively, on annular contactor pads 20 and 22. Medially directed tabs 142 and 148, are formed during the sewing together of 34; 38 and 42; 46; according to the procedure referred to in the preceding paragraph.

A first portion 180, of a longer elasticated, adjustable and openable posterior strap 26, is sewn to laterally directed extension tab 182, on contactor pad 20. Free end 184, of 180, is oversewn to prevent fraying. A second portion 186, of strap 26, is fitted with a slot-ring ring adjuster buckle 188. Second portion 186, is sewn to remaining laterally directed extension tab 190, on contactor pad 22, to complete the construction of harness 12.

Colored sheathed outer cables 120 and 122, are preferably about 900 mm in length and are of a softness such that they drape readily under their own weight. Cables 120 and 122, terminate within the case 192, of monitor unit 14.

Figure 9:
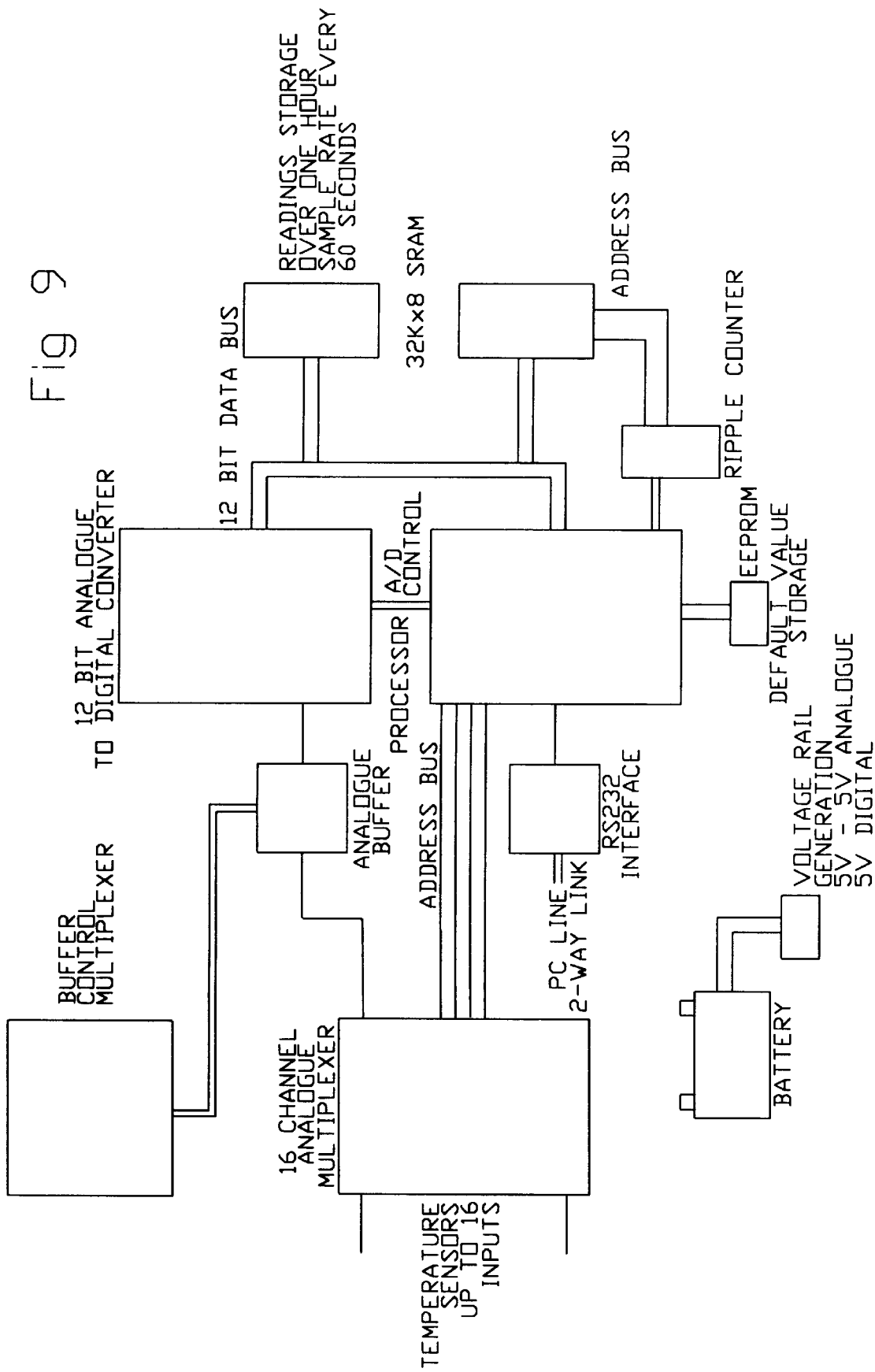
FIG. 9, is a block diagram of the circuitry employed in the instant system.
Figure 10:
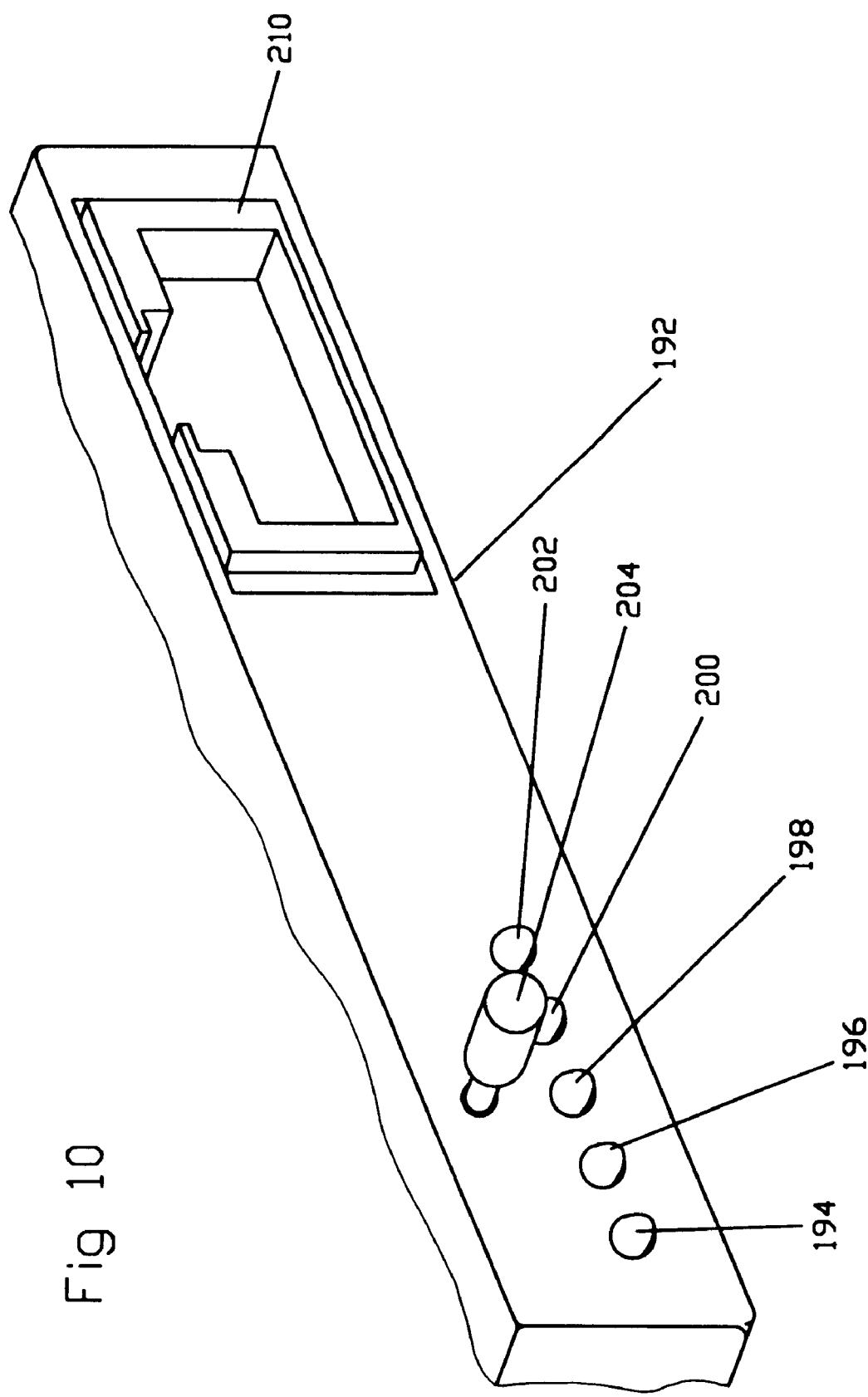
FIG. 10, is a diagrammatic representation of the LED display used on the monitor unit of the instant system.

With particular reference to FIGS. 9 and 10, monitor unit 14, has electronic microcircuitry based around a PIC16C65 microprocessor. This is used to control the data collection, storage and subsequent downloading of the recorded data. Monitor unit 14, receives input from sensors 66–80, which are precision temperature monitor ICs, type AD590 (Analog Devices Inc., Mass., USA) having three fine wire connecting legs, only two of which are used in the electrical circuit. This type of IC is of the 'temperature in—current out' type and has excellent linearity and stability over the required operating range. Although up to sixteen AD590 sensors can be monitored and information from them recorded and stored in monitor unit 14, only eight are used in this preferred embodiment. Each of sensors 66–80, is polled in turn and this is achieved by multiplexing each of them in sequence, though this occurs with extreme rapidity. Analogue multiplexers, type AD504 (Analog Devices Inc., Mass., USA) are used to achieve this and the polling routine is run every sixty seconds and continued for one hour. Each of the sensors are individually calibrated using analogue multiplexers to switch in two calibration resistors for each individual sensor. The calibration resistance values are set by an independent calibration reference laboratory, prior to supply to any end user, to establish both zero and absolute current values against calibrated reference temperatures, to within 0.01° C. By these means, and in contradistinction to prior art devices intended for mass screening of breast surface temperatures, it is established that temperatures measured with the device are both accurate and absolute. The use of absolute calibration in the instant system is the underlying reason for the permanent connection between harness 12 and monitor 14, via cables 120 and 122. Each of the readings from sensors 66–80, are fed into an operational amplifier, which conditions the signal so that it may be processed. This is achieved by converting the analogue signal into a digital one using a 12-bit analogue-to-digital converter. Once in digital form, the data are stored in two 32K static RAM chips; the operation of writing and addressing being controlled by the microprocessor.

The time between readings and their duration is controlled by the microprocessor. After a set of readings has been taken, the readings are stored in the static RAM until the microprocessor is instructed to download data to host PC 18. The interaction between host PC 18 and monitor unit 14, is achieved by using a serial RS232 interface link. Commands are sent to the microprocessor of monitor 14, which controls the outflow of data to host PC 18.

System variables, such as duration of the testing cycle and time between readings, can be set from within host PC 18, and downloaded, via the RS232 link to monitor unit 14, where they are stored in a non-volatile EEPROM. Once in the EEPROM, these new values will be applied to the taking of readings. These are protected 'system engineer' functions and cannot ordinarily be accessed by persons using system 10, for measuring breast surface temperatures.

Power for monitor unit 14, is provided by a rechargeable PP3 9 volt Nickel hydride battery and voltage levels are controlled using regulator chips to set the correct voltage levels. Separate voltage levels are used for the analogue and digital parts of the circuit in order to reduce interference.

Monitor unit 14, is provided with a series of coloured LEDs, best seen in FIG 10. LED 194, is green and is lit briefly when the test cycle is started and every sixty seconds, thereafter, when sensors 66–80, are being polled for the purpose of taking readings, LED 196, is red and is lit steadily during the process of downloading data to host PC 18, and briefly during the process of resetting, both hereinafter described. LED 198, is also red and is lit steadily in the event that monitor unit 14, is faulty and flashes regularly when a test cycle is completed. LED 200, is amber and is illuminated briefly when a manual reset operation is carried out. LED 202, is green and is lit steadily when the battery of monitor unit 14, is being charged.

A temperature sensing cycle is initiated by depressing a plunger 204, and keeping it depressed for two seconds. Thereafter, depressing plunger 204, again has no effect. Although resetting is normally carried out from within host PC 18, should there be a reason to abort a sensing cycle and start another, this may be accomplished by depressing a sub-flush manual re-set button 206, mounted in case 192, of monitor unit 14.

Figure 1:
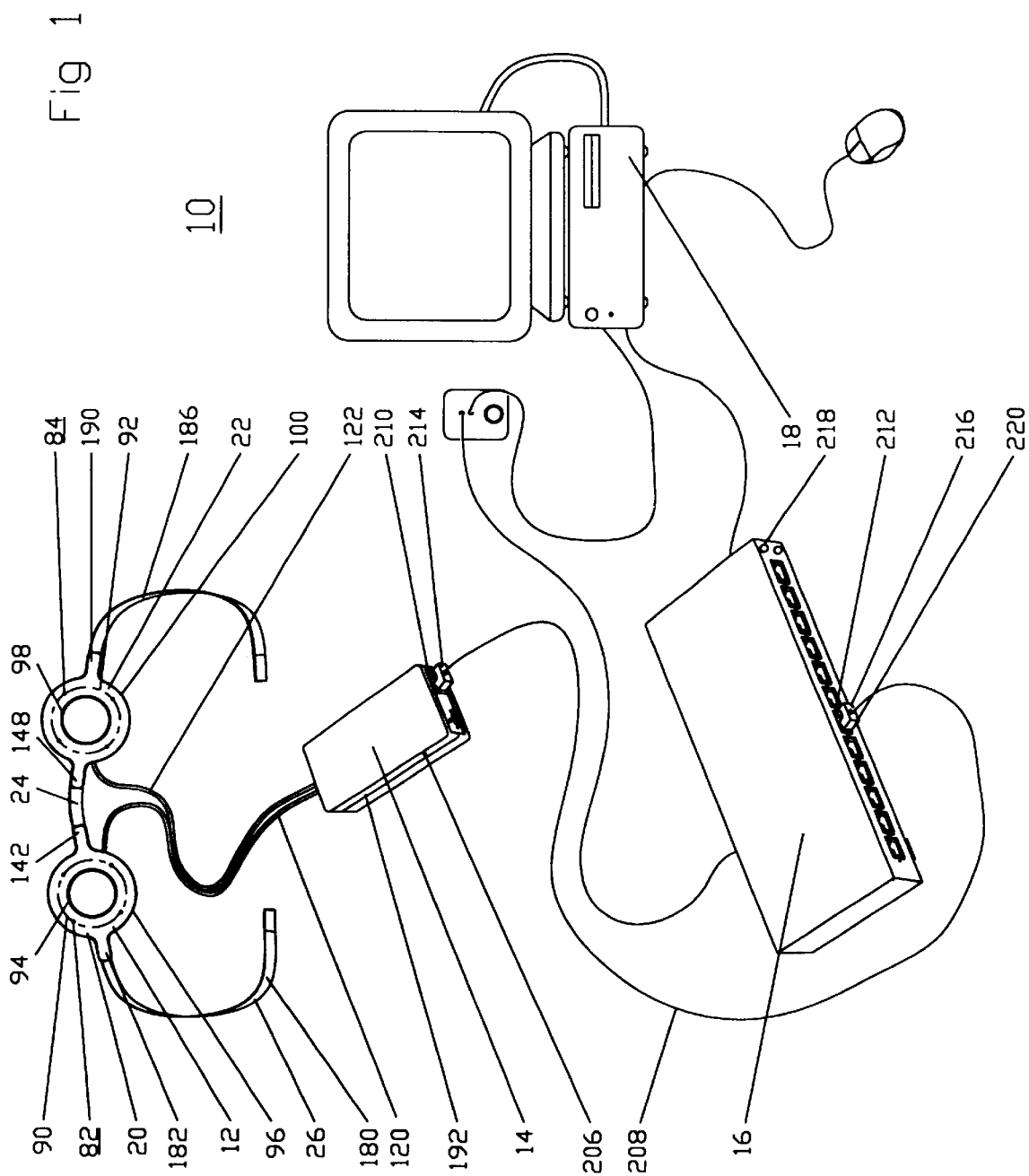
FIG. 1, is a diagrammatic perspective view indicating the principal elements of the system of the instant invention.
Figure 2:
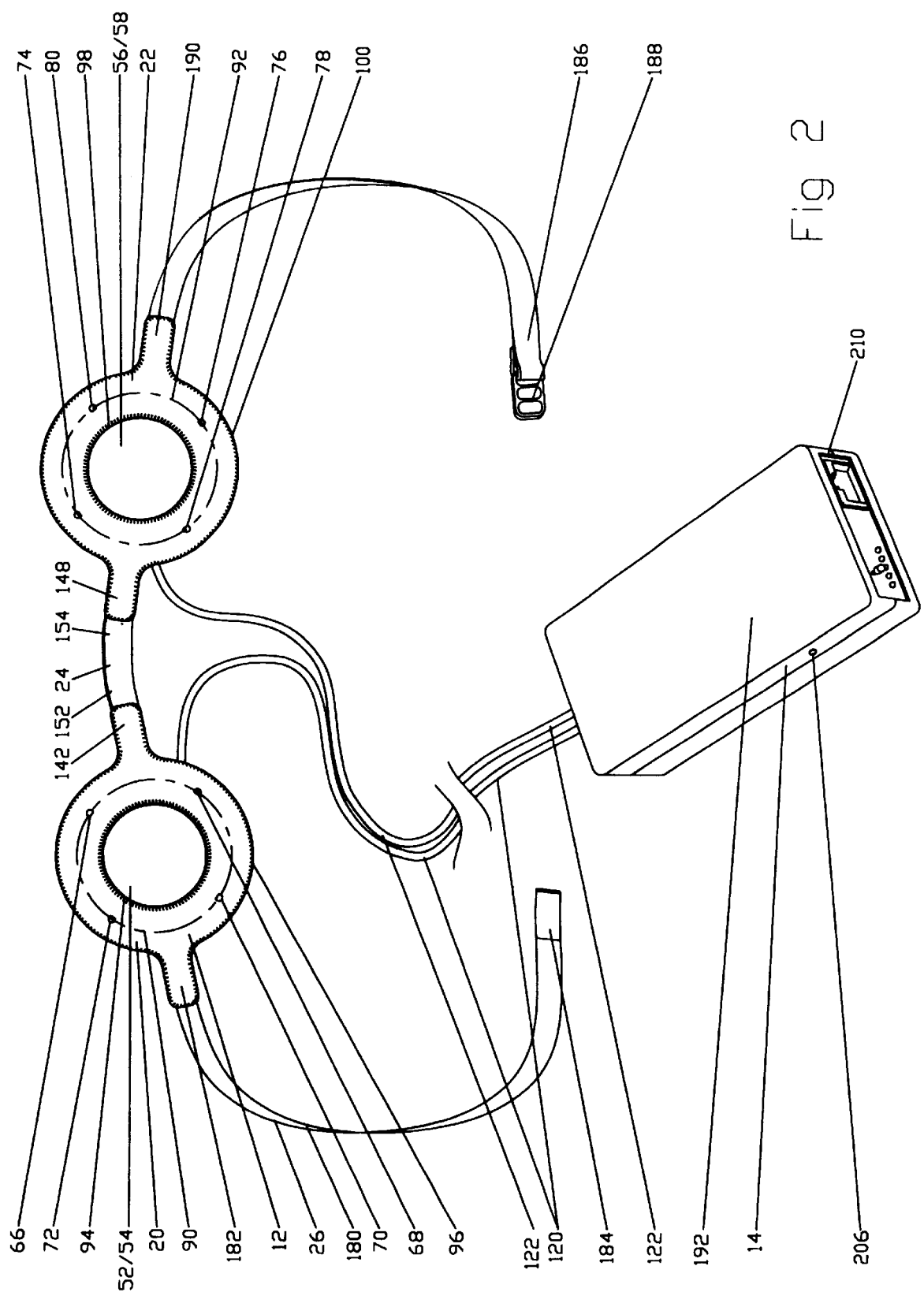
FIG. 2, is a diagrammatic perspective view of a most preferred embodiment of a harness and monitor unit according to the present invention, showing the inner, functional surface of the harness.
Figure 3:
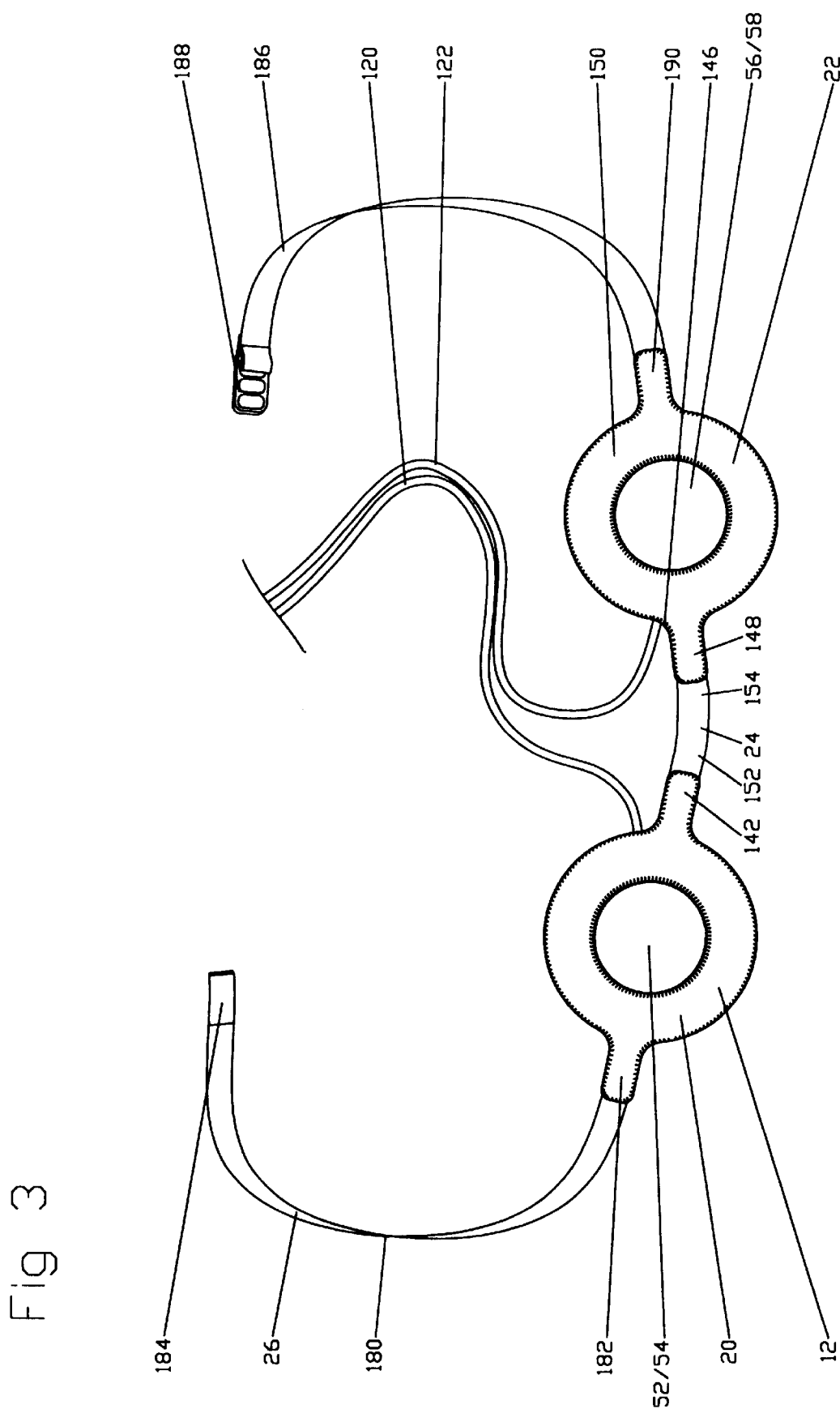
FIG. 3, is a diagrammatic perspective view of the outer surface of the harness of FIG. 2, with connecting cables foreshortened for clarity.

Upon completion of a testing cycle, monitor unit 14, is attache d, Via a connecting cable 208, which extends from socket 210, in case 192, to one of a series of substantially similar sockets exemplified by 212, on interface unit 16, as may be seen with reference to FIG. 1. Connecting cable 208, has substantially similar plugs 214 and 216, at both ends and is thus fully rever sible. Interface unit 16, is permanently linked to host PC 18, by cable means. Interface unit 16, provides charging means for monitor unit 14, and this function is activated upon connection and continues whether monitor unit 14, is downloading or not.

Interface unit 16, provides plug-in charging and download services for a plurality of monitor units, typically up to twelve at one time, thereby facilitating the use of system 10, in high traffic clinic-based breast screening programs.

Downloading of data stored within monitor unit 14, is accomplished by first selecting the channel to which socket 212, provides access. This is achieved by serially depressing a selector push-switch 218, until a reference LED 220, adjacent to socket 212, illuminates. As this is done it will be noticed that green LED 202, on monitor unit 14, illuminates and remains lit until 14, is disconnected from interface unit 16. Host PC 18, used for development, has a 100 MHz Pentium™ processor although most PCs having a 484, 100 MHz processor or better and capable of running the Windows 95™ operating system are adequate and the fact that most entry level machines are now much faster than this has no deleterious effect. Host PC 18, is provided with a dedicated program written in Turbo-Pascal™ for Windows 95™. This program provides, under keyboard or mouse command, communication with monitor unit 14, via the RS232 link. Simple commands initiate data download, capture and saving of downloaded data, and display of the data in graphical and tabular numerical form for each of sensors 66–80. In addition, the program provides means for pictorial graphic display of the temperatures, measured by each of sensors 66–80, at each polling, displayed in their correct spatial positions on each breast.

Preferred Method of Use in Screening for Risk of Breast Cancer and Detection of the Disease—Original Embodiment The primary intended use for system 10, is in screening women between twenty and fifty years of age and who have not reached the menopause, to detect whether or not they may be at risk of developing breast cancer at some future date. System 10, is so designed that it may be readily used in large populations of women, within short time scales and involves the accurate measurement of breast surface temperatures.

Reliable epidemiological data exist on the incidence of breast cancer which suggest that as many as one in twelve women in Europe and perhaps one in ten women in the USA, dies from breast cancer. It is inevitable that in any large scale screening program, numerous subjects will be tested who actually have the disease. Since it is also now known that breast surface temperature data, collected accurately at the appropriate point in the menstrual cyde, using progesterone assay to determine that point, are substantially similar in both the at-risk-but-with-no-disease-currently-present group and the active-disease group and further, that those data are different from the not-at-significant-risk group, the instant system 10, has potential for secondary use in confirmation of the presence of active disease.

In use, the subject to be investigated using the instant system, is counseled upon recruitment as to the nature of the test. At least one month prior to the test, she is provided with a home-use urine dip test kit and a saliva collection kit. The urine dip test kit is in the form of a series of paper strips impregnated with a suitable agent which reacts to the surge of luteinizing hormone in the urine which occurs at ovulation, by a color change from green to yellow. Such a test may be obtained commercially under the name Unipath™. The test is carried out by placing the strip into an early morning urine sample, collected shortly after waking each day, starting on the eighth day from the first day of bleeding of the last menses and continuing until the color change is observed upon testing. If the subject has a notional twenty-eight day cycle, the color change will normally occur on day fifteen.

The saliva sample kit (not shown) is in the form of a series of three screw cap sterilized 5 ml saliva tubes and a strong, small, divided container suitable for transmission by post. On the day the color change is observed with the urine test, the subject collects a first saliva sample by dribbling a small amount into the first bottle which she then reseals. The subject then collects a further two saliva samples on the morning of each of days 18 and 21. The samples should be kept in a domestic refrigerator until the series is complete.

If the color change in the urine dip test occurs earlier, probably indicating a shorter cycle, the first saliva collection is still made on the day the color change is observed, the second on the third morning thereafter (leaving two clear, non-collection days) and the third on the third morning after the second collection (also leaving two clear, non-collection days). Once the third and last saliva sample has been collected, the container containing all three samples is sealed and sent, by post, to a suitable laboratory equipped to carry out radio-immunoassay for progesterone levels. These results are used to measure and predict the most suitable date in the subject's next cycle to carry out the breast temperature test. One such commercial laboratory is BioClinical Services Ltd (BioClin International), Willowbrook Laboratories, St Mellons, Cardiff, Wales, UK.

Based on the results of the saliva progesterone assays from the laboratory, the investigator or investigating group select the appropriate day for the subject to attend a test center and invite her to do so. In a subject with a normal twenty-eight day cyde this will normally be day seventeen of the next cycle; in women with differing cycles it will normally be the 'day seventeen equivalent'.

In a warm environment, where the ambient temperature should be maintained at 22°C.±2° C., the subject is provided with privacy and requested to doff her upper garments. With assistance of a female helper or nurse, the subject is fitted with harness 12, of the system 10. Harness 12, is secured in place with posterior adjustable strap 26. Anterior strap 24, is adjusted so that, when 24, is under tension, the pitch of central holes 50; 52 and 54; 56, in annular contactor pads 20 and 22, correspond with the pitch of the subject's nipples. Harness 12, is then adjusted on the breasts such that central holes 50; 52 and 54; 56, of annular contactor pads 20 and 22, are disposed concentrically about the nipples. The subject may, in addition, wear her own brassiere if she wishes, or a sports type elasticated brassiere or no brassiere. It is mandatory, however, that she wear a substantial and reasonably close-fitting over garment, such as a high-neck, medium-weight shirt, to limit or prevent any generalized heat loss. It is essential that identification details for both the subject and monitor unit 14, are recorded together and that the integrity of this combined information is maintained. It will be appreciated that only one size of the instant harness 12, is provided and required. The subject should be provided with a lightweight dressing gown having large pockets. We prefer to have these gowns modified so that there is a slit in the dressing gown material, parallel to and somewhat below the upper margin of the pocket and extending for most of its width. The edges of this slit should be oversewn with tape to prevent fraying and tearing.

Connecting cables 120 and 122, which extend between harness 12 and monitor unit 14, are led out from under the lower margin of the over garment and monitor unit 14, is passed through the slit in the dressing gown. Monitor unit 14, is supported until the test cycle is started. The subject is seated comfortably in the clinic setting and this should provide as welcoming and stress-free an environment as possible. It is helpful to provide her with reading materials.

The structure, design and sizing of annular contactor pads 20 and 22 and harness 12, in general, are such that not only is a good fit obtained on both large and small breasts with large and small areolar areas but excellent contact is also maintained between sensors 66–80 and both the superior and inferior aspects of the breast surfaces. Because contactor pads 20 and 22, are soft and conformable they readily mould to breast curvature, even on the concave upper aspect, unlike many prior art devices which, whatever their functional basis, are somewhat rigid and have a consequent tendency to 'tent' over the upper aspect, often holding functional surfaces away from the breast surface. It might be thought that the presence of small hard sensor cans 66–80, protruding from contactor pads against the breast surfaces would be uncomfortable or painful, however, contra-intuitively, tests under confidentiality arrangements on numerous subjects having breast sizes which varied from very small, through moderate, to very large, have all indicated that there is little awareness of the sensors at all and if any, it was usually only brief and immediately followed donning the harness. The term 'awareness' is chosen carefully since no subject reported pain or even discomfort. In all of these subjects, readings were obtained from all sensors throughout a one hour test cycle.

To start the test, the assistant, helper or other designated person, depresses plunger 204, on monitor unit 14, for two seconds, observing that green 'start' LED 194, illuminates briefly, to confirm initiation of the test. Once this has been done, monitor unit 14, is placed in a pocket of the dressing gown. Since plunger 204, is inactivated once the test has commenced accidental or deliberate interference with it has no effect. On the other hand, if there is a valid reason for interrupting the test, particularly if this involves removing or significantly readjusting harness 12, monitor unit 14, may be manually re-set by depressing sub-flush button 206, in case 192. The tip of a ball point pen is a convenient implement for accomplishing this and it will be noticed that amber LED 200, is lit briefly when this is done.

Throughout the test period, the subject should be encouraged to sit quietly and avoid exertion and should not imbibe hot or stimulating liquids. At the end of one hour, the test will be complete and this may be confirmed by the person in charge of the test observing that red LED 198, is flashing regularly. The subject may then be taken back to the private cubicle to doff harness 12, and dress in her normal clothing, prior to departure from the test center.

At the end of a test cycle, data from monitor unit 14, derived from the subject is downloaded into the host PC 18, as hereinbefore described during which process red LED 196, is lit steadily. As a general rule, data collected during the first thirty minutes or so of the test should be discarded, since this period of time is necessary for the annular contactor pads 20 and 22, sensors 66–80, over garment and brassiere, if worn, to equilibrate and stabilize. Thereafter, a relatively stable pattern of temperature response from each of sensors 66–80, is a normal finding. These data are then evaluated by a skilled, trained person capable of comparing the subject's breast temperature data with known normal and abnormal data with a view to reaching a conclusion concerning whether or not the subject may be at risk of developing breast cancer at some future date.

In the event that the conclusion concerning the risk of developing breast cancer at some future date is positive, the subject would be informed promptly and invited back to participate first in a re-test and then in other tests. The purpose of these is to establish whether or not she may have existing cancer since, although the object of the test of the instant invention is not, primarily, to detect actual cancers, there will be some subjects who come forward who do have the undiagnosed condition. If she is negative to other tests for cancer, she will be informed that, according to the instant test, she may well be at a significant risk of subsequently developing breast cancer. This knowledge, far from being a prophecy of doom, allows surveillance, prevention and future intervention strategies to be planned and implemented with improved chances of preventing the disease or should it prevail later, successfully treating it, at an early stage. Handled well at counseling, it is eminently possible to engender a strongly positive psychological response in the subject. Alternatively, if the subject has already had other tests which suggest that she may have breast cancer or has physical signs which suggest breast cancer, the results from tests using the instant system may be used to confirm or deny previous findings.

On the other hand, if the test is negative, the subject will also be so informed. In this event, the subject may well be reassured, even to the point of euphoria and it is incumbent upon those who carry out the test to abjure such subjects that it is very much in their own interests to return for re-testing at a suitable interval, which may be, say, two years. In any case, a follow-up record and recall system must be maintained in order that all subjects tested can be called for a re-test after a suitable period, no matter how short or long this may be.

In a few subjects which we encountered, the areolar areas were exceptionally large and although this phenomenon has not been seen in very small breasts, it has been seen in some of relatively moderate size. Therefore, we made and tested examples of harness 12, wherein the nominal external diameter of contactor pads 20 and 22, has been made 150 mm and the diameter of central holes 52; 54 and 56; 58, has been made 80 mm. This variant is, in other respects, substantially similar to the preferred embodiment and has, therefore, not been further separately described.

From the foregoing, it will now be apparent that the original embodiment of the present invention provides a system capable of making accurate measurements of temperatures on the surface of the human breast that is clearly differentiated from the prior art by its structure and which incorporates means to reliably record and store measurements of these temperatures and to manipulate and display them. Further, that use of the instant system, according to the method hereinbefore disclosed, constitutes a method for the assessment of the risk of future development of breast cancer in women who do not currently have the disease and for the detection of breast cancer in women who may have the disease.

New and Most Preferred Embodiment

In the new and most preferred embodiment, we have made numerous improvements directed at improving functionality, reliability, durability, accuracy, acceptability for the test subject and service provider, effectiveness and security. Most of these aims have been achieved by structural improvements.

System 310, is an improved apparatus for thermometric breast assessment, directed, by means of the function of its structural elements, towards the mass screening of the human breast, including the assessment of breast cancer risk, and comprises the principal elements of a mechanical adjustable harness 312, having a permanently connected datalogger 314, and a host personal computer (PC) 316, having an integral interface 318. Host PC 316, is provided with a mouse 320, VDU 322 and keyboard 324.

System 310, is intended for the measurement of breast temperatures, over a period normally comprising thirty minutes for temperature equilibration of harness 312, with the subject and one hour for data collection. Notwithstanding this, the instant invention may be used to detect breast cancer and for other breast thermometry applications over different periods which may be up to, for instance, seven days.

It is important to note that mechanical adjustable harness 312, is not physically attached to the breast with adhesives or tape. Neither is harness 312, a brassiere, since it cannot provide support for the breasts and does not contain them, nor is it a brassiere insert since it is not necessary to use it in conjunction with a brassiere. Finally, harness 312, is not a garment, since it has no purpose or use as apparel and is used only in relation to its specific function, hereinafter described.

Harness 312, only one size of which is needed to fit almost all subjects, includes two discrete improved and novel ring-like or annular contactor pads 328 and 330, each of which includes a thin flexible printed circuit board (PCB) 330; 332, manufactured in the flat condition as a multiple-layer polyimide laminate ribbon and conveniently having a thickness of about 0.20 mm overall and a width of about 22 mm and further having a novel overall shape somewhat reminiscent of a large inverted question mark with an extended tail. Ribbon PCBs 330; 332, are substantially identical and are so designated to differentiate left and right orientation.

In each of ribbon PCBs 330; 332, first portions 334 and 336, respectively, extend from first ends 338 and 340, to form, substantially, an incomplete circle, the inner margins 342 and 344, of which, in the flat condition, each largely endoses a circular area, preferably of about 100 mm diameter. Second portions 346 and 348, continuous respectively with first portions 334 and 336, are curved and extend upwards over some 90° of arc; and third portions 350 and 362, continuous respectively with second portions 346 and 348, are substantially straight to form leads and extend upwards to second ends 354 and 356, of ribbon PCBs 330; 332. It will thus be appreciated that a ribbon PCB 330, in an unmodified or preassembly state, may be converted into a ribbon PCB 332, by rotating it through 180° about an axis disposed centrally along the length of third straight portion 350.

A further novel structural feature is the provision of a plurality of integral flexible inner primary tabs 358–368 and 370–380, is provided about inner margins 342 and 344, of first circular portions 334 and 336, of ribbon PCBs 330; 332, preferably but not necessarily disposed at intervals of 60° and extend radially and inwardly, preferably for about 18 mm. Additional, similar integral primary tabs may optionally be disposed about the outer margins 382 and 384, of first circular portions 334 and 336, and, in this embodiment, outer primary tabs 386 and 388, are deployed.

Each of ribbon PCBs 330; 332, carries electrical connection means in the form of ten parallel insulated copper tracks, 390–408 and 410–428, respectively. Insulated copper tracks 390 and 410, are thinner than other tracks and constitute means, in conjunction with other means, described hereinafter, for long term monitoring of the electrical integrity of ribbon PCBs 330; 332. Insulated copper tracks 390 and 410, are disposed entirely peripherally around inner margins 342 and 344 and outer margins 382 and 384, of ribbon PCBs 330; 332, respectively.

Insulated copper tracks 392 and 412, extend into outer primary tabs 386 and 388, and provide electrical connection means thereon. Insulated copper tracks, 394–404 and 414–424, extend into inner primary tabs and provide electrical connection means thereon. Insulated copper tracks 406 and 426; 408 and 428, provide first common and alternate common electrical connection means extending into all primary tabs of ribbon PCBs 330; 332, respectively.

Each of inner primary tabs 358–368 and 370–380 and outer primary tabs 386 and 388, is provided with a first and second series of exposed soldering points, formed within ribbon PCBs 330; 332, at the time of manufacture. As may best be seen by brief reference to FIG. 17, first series of exposed soldering points is perforated and is indicated, by way of example, at 432–436. Second series of exposed soldering points comprises grouped multiple points (not numbered separately in the drawings), not perforated and is indicated, by way of general example at 430. First series of perforated exposed soldering points 432–436, constitutes adaptations of ribbon PCBs 330; 332, to provide reception and mounting means for surface mounted thermal sensor means, hereinafter described, on all primary tabs 358–368; 386 and 370–380; 388.

A plurality of pairs, conveniently two pairs, of integral flexible secondary tabs 438; 440, 442; 444 and 446; 448; 450; 452, is provided, extending radially inwardly and outwardly, at convenient positions around inner margins 342 and 344 and outer margins 382 and 384, of first circular portions 334 and 336, of ribbon PCBs 330; 332, respectively. When ribbon PCBs 330; 332, respectively are viewed in front elevation in the flat condition, first pairs of secondary tabs 438; 440 and 446; 448, are seen to be disposed in corresponding lower positions near but not at the bottom of first circular portions 334 and 336. When viewed from the same vantage point, second pairs 442; 444 and 450; 452, of secondary tabs are seen to be disposed on first circular portions 334 and 336, at points 454 and 456, which adjoin second curved portions 346 and 348, in corresponding upper positions.

As may best be seen by brief exemplary reference to FIGS. 18 and 18a, which are enlarged perspective views of 442; 444, secondary tabs are preferably strengthened by the provision of hatch pattern reinforcing material within the polyimide laminate, indicated at 458. Exemplary secondary tabs of 442; 444, are adapted by the provision of fold lines 460 and 462, also formed in the laminate, to allow them each to be formed into a flap which, in fully assembled contactor pads 328 and 330, are outwardly directed for use as elements of folded flap closure means. Secondary tab 442, is adapted by the provision of a pad 464, of hook closure material, secured by self-adhesive means, at a suitable position on its outer surface 466, and secondary tab 444, is similarly adapted by the provision of a pad 468, of loop closure material, also secured by self-adhesive means, at a corresponding position on its inner surface 470. When secondary tab 442, is folded to form a flap and apposed to a similar flap formed by folding secondary tab 444, such that hook closure materials pads 464 and 468, are brought into contact, closure is effected and receiving means is formed for the releasable and slidable receival of body strap elements, hereinafter described, of harness 312.

Second upper pairs 442; 444 and 450; 452, of secondary tabs are additionally adapted by the provision of fixing means, conveniently in the form of soldering points 472; 474 and 476; 478, exposed on both sides and incorporated during the manufacture of ribbon PCBs 330; 332. Similar soldering point fixing means 480; 482 and 484; 486, are provided on small extensions 488; 490 and 492; 494, formed on inner margins 342 and 344 and outer margins 382 and 384, of first ends 338 and 340, of ribbon PCBs 330; 332, respectively.

During assembly, soldering points 480; 482, exposed on the outward or front-facing aspect 496, of first end 338, of PCB 330; are drawn into apposition with soldering points 472; 474, exposed on the rear or breast-facing aspect 498, of upper secondary tab pair 442; 444, of PCB 330, thereby forming an annulus which is also a flexible frustum of a cone, so as to provide a novel breast accommodating structure 500; for a left breast. Frustum breast accommodating structure 500, is completed and secured by forming wire and solder joints, the wire elements of which are indicated at 502 and 504. Conversely, by drawing soldering points 484; 486, exposed on the outward or front-facing aspect 506, of first end 340, of PCB 332, into apposition with soldering points 476; 478, exposed on the rear or breast-facing aspect 508, of upper secondary tab pair 450; 452 of PCB 332; there is formed, in a novel manner, a flexible frustum of a cone so as to provide a novel accommodating structure 510; for a right breast. Wire elements of wire and solder joints, securing structure 510, are indicated at 512 and 514. Details of wire and solder joints may be noted by brief reference to FIG. 16.

With the exception of special areas, shortly hereinafter described, formed novel breast accommodating structures 500 and 510, second curved portions 346 and 348 and straight lead portions 350 and 352, of ribbon PCBs 330; 332, are provided, so as to substantially cover the greater part of their front-facing aspects 496; 506, with first outward or front-facing elements 516; 518, of adhesively attached, deanable, permanent covering means, advantageously made in plastics. Similarly ribbon PCBs 330; 332, are provided on their breast-facing aspects 498; 508, with second similar breast-facing elements 520; 522. Advantageously, elements 516; 518 and 520; 522, have similar margins elements 524; 526 and 528; 530, which preferably in all cases extend a small distance beyond inner margins 342 and 344 and outer margins 382 and 384, respectively, of ribbon PCBs 330; 332, in order that they may be permanently edge-sealed by suitable sealing means such as adhesive means or radio frequency sealing means, thereby forming covers 532 and 534. Covers 532 and 534, are preferably made from a soft, thin, polyvinyl chloride or similar flexible fabrics material cover which is relatively inert to mild antiseptic solutions used in low-risk clinical environments for hygienic wipe-cleaning of human contact items.

Front-facing elements 516; 518, of covers 632 and 534, are preferably die-cut and entire, extending over the whole of front-facing aspects 496; 506, of ribbon PCBs 330; 332, except for regions 536; 538, near second ends 354 and 356, which are uncovered and over secondary tabs 438; 440, 442; 444 and 446; 448, 450; 452, which are, optionally, uncovered. Breast-facing elements 520; 522, of covers 532 and 534, are also preferably die-cut and, though generally similar to elements 516; 518, are not entire in that they are provided with additional die-cut shapes 540–552, and 554–566, which register centrally over each instance of first series of exposed perforated soldering points exemplified by 432–436. In general, covers 532 and 534, are directly adhesively attached to ribbon PCBs 330; 332. However, advantageously, each aspect 496; 506, 498; 508, of each of novel primary tabs 358–368; 370–380, 386 and 388, is provided with a very thin layer of adhesively applied closed cell foam having substantially the same size and shape and indicated, by way of example at 568 and 570, in FIG. 17. It will now be appreciated that, whereas the overall thickness of fully assembled contactor pads 328 and 330, may be held to a preferred thickness of about 1.5 mm throughout their greater parts, in the areas of primary tabs 358–368; 370–380, 386 and 388, the thickness will be about 2.5 mm due to the presence of closed cell foam layers exemplified by 568 and 570. This arrangement is a significant improvement over the original embodiment in that heat loss prevention structures 568 and 570, in the new and most preferred embodiment are confined to those areas where they are needed, namely in the immediate regions of sensor locations on primary tabs. This has the advantageous consequences of reducing overall bulk and the promotion of enhanced flexibility and conformability in breast accommodating structures 500 and 510. The further effect of reducing bulk and mass is that the new and most preferred embodiment does not, of itself, tend to act as a heat sink.

A body strap assembly 572, of harness 312, includes a first element which is in the form of a first longer posterior elasticated strap 574, provided at a first end 676, with releasable attachment means and adjustment means in the form of a male portion of a quick-release buckle 578, combined with slide adjustment means for strap 574, and also with parking means in the form of a slidable strap loop 580, for parking excess strap length. A second element is in the form of a shorter second posterior elasticated strap 582, adapted at a first end 584, with releasable attachment means in the form of a female portion of a quick-release buckle 586, for releasable engagement with male buckle portion 578, of the first element.

Additional body strap assembly elements are in the form of first and second transverse anterior elasticated straps 588 and 590, each of similar length and non-releasably secured to one another at both ends so as to form 'V' joins 592 and 594, each having an enclosed angle which is conveniently about 40°. A second end 596, of first longer posterior strap 574, is non-releasably secured to 'V' join 592, of joined transverse anterior straps 588 and 590, to form a symmetrical 'Y' arrangement. Similarly, a second end 598, of second shorter posterior strap 582, is non-releasably secured to 'V' join 594, of joined transverse anterior straps 588 and 590, also forming a symmetrical 'Y' arrangement.

A final body strap assembly element is in the form of a short vertical anterior elasticated strap 600, made of loop closure material, non-releasably secured centrally and at right angles to transverse anterior elasticated strap 588. Anterior elasticated strap 590, is provided with releasable securing and tension adjustment means in the form of a length of hook closure material 602, preferably extending over its full width and having substantially the same length as the width of vertical anterior strap 600. With regard to all body strap assembly elements, non-releasable securing means are conveniently provided by sewing.

The relationship between the elements of body strap assembly 572 and flexible fully assembled contactor pads 328 and 330, of harness 312, is important and the width of transverse anterior elasticated straps 588 and 590, is selected so that they may be readily releasably engaged, in a slidable manner, with upper folded flap closures 604; 608, formed from upper secondary tab pairs 442; 444 and, 450; 452 and lower folded flap closures 606; 610, formed from lower secondary tab pairs 438; 440, 446; 448, respectively.

Fundamentally precise positioning of annular frustum contactor pads 328 and 330, over each breast, concentric with the nipple, regardless of breast size or shape is possible partly due to the novel, open, flexible breast accommodating frustum structures 500 and 510, partly due to the shape imposed by the provision of second curved portions 346 and 348, of ribbon PCBs 330; 332 and partly due to the fact that annular frustum contactor pads 328 and 330, may be freely located with respect to one another other over any rational range. The additional advantageous effects of achieving low bulk in structures 500 and 510, and locating heat loss prevention materials only on primary tabs will also have been noted.

The dispositions on flexible breast accommodating frustum structures 500 and 510, of folded flap closures 604; 608 and 606; 610, forming securing means for elasticated transverse anterior straps 588 and 590, and the geometry of mutual permanent attachments 592 and 594, between these straps, are selected to optimize contact between frustum contactor pads 328 and 330 and the subject's breasts. Vertical anterior strap 600, provides further adjustment directed towards optimizing breast contact, particularly on the medial aspects of both breasts, by allowing straps 588 and 590, to be gently drawn towards one another in the central area between the breasts. Both frustum contactor pads 328 and 330 and body strap assembly 572, are intended to provide a one-size-fits-all solution for the great majority of the population, however, it is recognized that there will be a need for a low use variant for extremely large subjects and another for extremely small subjects. This is a significant improvement over prior art systems which depend upon a multiplicity of sizes of brassiere or brassiere inserts.

It is important to note the functional advantage conferred upon improved harness 312, by the provision of the novel structural feature of primary tabs 358–368; 386, 370–380; 388, for mounting thermal sensor means. Primary tabs 358–368; 386, 370–380; 388, are so sized and shaped that, whatever breast size or shape novel annular frustum structures 500 and 510, are drawn against, such that the breasts protrude through the structures, primary tabs 358–368; 386, 370–380; 388, will tend to be splayed, thereby being pressed gently but firmly into intimate contact with the breast surfaces.

Since the superior aspect of the female breast is typically concave, it is important to take all reasonable steps in apparatus used in a test of this importance, to ensure that good contact is achieved in this region. Accordingly, further advantageous cooperation between the body strap assembly 572, and breast accommodating frustum structures 500 and 510, is achieved by disposing first pairs of secondary tabs 438; 440 and 446; 448, in positions on first circular portions 334 and 336, of ribbon PCBs 330; 332, respectively, such that when structures 500 and 510, are formed, lower folded flap closures 606; 610, lie in respective south polar positions. The effect of this is to cause lower anterior transverse strap 590, to lie close to and with mild compressive effect upon those inner primary tabs 362, 364; 374, 376, directed over the inferior aspects of the left and right breasts, respectively.

More importantly, upper folded flap closures 604; 608, lie in respective north polar positions causing upper anterior transverse strap 588, to lie close to those inner primary tabs 358, 368; 370, 380, directed over the superior aspects of the left and right breasts, respectively. Upper folded flap closures 606; 610, are also optimally positioned to cause upper anterior transverse strap 590, to be biased such that outer primary tabs 386 and 388, are substantially and mildly compressively covered.

Turning now to thermal sensing means, we now prefer to use a larger number of sensors than in the original embodiment of this invention. Thus first and second arrays 612 and 614, are deployed, respectively, on the breast-facing aspects 498 and 508, of each of contactor pads 328 and 330. First and second arrays 612 and 614, each comprises seven thermal sensors, arranged as six sensors 616–626; 628–638, disposed symmetrically, one on each of inner primary tabs 358–368; 370–380, of ribbon PCBs 330; 332, together with one further sensor 640 and 642, disposed on outer primary tabs 386 and 388 and directed towards each axilla. Sensors 616–626, 640 and 628–638, 642, have no covering in order to ensure that there is no thermal barrier interposed between them and the surfaces of subject breasts.

Since the development of the original embodiment of this invention, we have continued to investigate available sensors and maintain our preference for an integrated circuit precision temperature transducer of analog type which produces an output current proportional to absolute temperature. However, there are now available temperature-voltage based types which could be used with little difference in performance in general use and with possible advantages in certain specific applications. It will have been noted that primary tabs 358–368; 386 and 370–380; 388, of all ribbon PCBs 330; 332, are provided with second exposed grouped multiple soldering points, exemplified at 430, in FIG. 13, which constitute connection means for bridging wiring connections for most preferred sensor means and also connection means for micro-miniature trimming components and bridging wiring connections for alternate versions of this most preferred embodiment which employ temperature-voltage based type sensors.

We most prefer a temperature-current sensor of the AD588JH type (Intersil Corporation, Fla., USA) in a metal can package type TO-52. As may best be seen by reference to FIG. 13, sensor 616, exemplary of sensors 616–626; 640, and 628–638; 642, has a metal can package 644, with a body portion 646, which is of substantially cylindrical form of general diameter about 4.7 mm and overall height of about 3.7 mm. Flat-topped upper surface 648, of body portion 646, meets cylindrical side surface 650, at a rounded periphery 652, having a radius of about 0.5 mm. A lower, flanged portion 654, of can package 644, has a diameter of about 5.4 mm and a depth of about 0.4 mm. Under-surface 656, of can package 644, is epoxy resin and from it originate three stiff wire legs 658–662, spaced apart from one another and each having a manufactured length of about 13 mm. Most importantly, functional surfaces 648; 650, are used unsheathed, in order to ensure intimate contact with the breast surface and to maximize thermal transfer. Advantages of the AD588JH temperature transducer over the AD590 temperature transducer used in the original embodiment are both structural and functional. The AD588JH offers improved linearity and easier and more precise calibration over the target temperature range. Advantages of the TO-52 can package over the TO-92 can package used in the AD590 temperature transducer reside in the cylindrical shape of the TO-92 and the fact that its metal outer can and smaller resin mass provide improved thermal transfer.

Thin insulating and spacing means are in the form of a plastics disk washer 664, of similar diameter to flanged portion 654, of can package 644, and provided with three perforations 666–670, of similar size to and spaced apart in the same manner as perforated soldering points 432–436. Wire legs 668–662, are each received intimately into and through both perforated disk washer 664, and perforated soldering points 432–436 and are non-releasably secured to 432–436, by soldering and thereafter are trimmed as nearly flush as possible to minimize any residual nibs. Plastics disk washer 664, is interposed between under-surface 656, of can package 644 and perforated soldering points 432–436, respectively, to prevent any possibility of a short circuit between flanged portion 654, of can package 644 and perforated soldering points 432–436.

Exemplary closed cell foam layer 668, is preferably die cut and provided with a substantially circular hole 672, so positioned as to register with and pass over flanged portion 654, of can package 644 and fit intimately over plastics disk washer 664. Circular die-cut hole 540, of cover 532, fits intimately around body portion 646 and also lies intimately above and upon flanged portion 654, of can package 644. Plastics disk washer 664, has an advantageous spacing effect of increasing the exposed profile of can package 644 and, in the fully assembled condition, body portion 646, stands about 3 mm proud of cover 532.

It will now be appreciated that by the provision of perforated soldering points, exemplified by 432–436, the logical requirement that sensor connection must always be on breast-facing aspects 498; 508, of ribbon PCBs 330; 332, is satisfied. As previously indicated, a ribbon PCB 332, is formed by rotating a ribbon PCB 330, in a pre-assembly state, through 180° about an axis disposed centrally along the length of third straight portion 350, it follows that sensor connection will always be made on a first surface 674, of ribbon PCB 330, and on a second surface 676, of ribbon PCB 332. By brief reference to FIG. 13, it may be seen that this results in second exposed grouped multiple soldering points, exemplified at 430, being visible on first surface 674, of ribbon PCB 330, which upon assembly, becomes front-facing aspect 496, of contactor pad 328, but not on second surface 676, of ribbon PCB 332, which upon assembly, becomes front-facing aspect 506, of contactor pad 330.

Exemplary closed cell foam layers 568 and 570, register with front-facing aspect 496 and breast-facing aspect 498, respectively, of exemplary novel primary tab 368. Closed cell foam layer 568, is entire and has the primary function of preventing radiant and conductive heat loss from primary tab 358 and most especially from associated sensor 616. Closed cell foam layer 568, has the secondary function, derived from its structural features of thickness and construction, of mitigating, by cushioning means, the potentially deleterious effects of any residual solder nibs or trimmed wire ends resulting from the manufacturing process, thereby ensuring that cover 532, does not become abraded or pierced.

In the case of closed cell foam layer 570, the primary function is to mitigate the potentially deleterious effects of any residual solder nibs or trimmed wire ends, thereby ensuring that cover 532, does not become abraded or pierced with the intention, in particular, since it is located on breast-facing aspect 498, of preventing any undesirable breast contact. The secondary function of closed cell foam layer 570, namely prevention of heat loss is, however, important, since, if 570, were not interposed between cover 532 and PCB 330, the proximity of copper tracking within PCB 330, could lead to undesirable lateral conductive heat loss in the context of an apparatus intended to measure temperature differences to ±0.01° C.

It will now be appreciated that, in this improved version of harness 312, of the instant invention, we have disclosed structural and functional improvements, eliminated a number of components and numerous manufacturing steps and, additionally, the weight has been reduced. Furthermore, covered ribbon PCBs 330; 332, drape much more readily than sheathed cables 120; 122, of the original embodiment of this invention. Advantage is taken of these improved drape characteristics in straight portions 350; 352, of ribbon PCBs 330; 332, which constitute soft and very flexible connecting leads. It will have been noted that covers 532; 534, provided on contactor pads 328; 330, do not extend to second ends 354; 356, of straight connecting lead portions 350; 352, of ribbon PCBs 330; 332. Each of uncovered regions 536; 538, which constitute connecting areas of PCBs 330; 332, is adapted by the provision of eleven discrete exposed soldering points 678–698; 700–720, constituting electrical connection means for soldered connection to data-logging means.

Turning now to data-logging means, these are provided in the form of a data-logger 314, Data-logger 314, has a substantially oblong case 722, fitted with on a light adjustable strap 724, provided with quick release connection means in the form of a quick release buckle 726, for suspension of data-logger 314, around the neck of a test subject. Connecting lead portions 350; 352, of ribbon PCBs 330; 332, which are conveniently about 320 mm long, are folded through 180° to facilitate receival into data-logger 314, along top long horizontal edge 728, of case 722. Within data-logger case 718, there are provided mechanical securing means in the form of crimping means (not shown) and electrical connection means in the form of soldering points (not shown) constituting permanent soldered receival and connection means for corresponding electrical connection soldering points 678–698; 700–720, of connecting areas regions 536; 638, of ribbon PCBs 330; 332.

Data-logger 314, which provides significantly improved functionality, safety and security over monitor unit 14, disclosed in the original embodiment of the instant invention, is provided with electronic microcircuitry which may best be understood by reference to FIG. 26, which is a block circuit diagram, labeled, not numbered. Data-logger 314, is based around a PIC17C66 microprocessor (Microchip Technology Incorporated, AZ, USA) which is used to control data collection, storage and subsequent downloading of recorded data to host PC 316. Data-logger 314, is a sixteen-channel device, of which fourteen channels are used to monitor outputs from each sensor comprising the two 7-sensor left and right breast sensor arrays 612 and 614. Two channels are also used to confirm the integrity of harness 312. Data-logger 314, is provided with clock timing means and the processor is capable of polling every sensor at intervals selected to be from five seconds to one hour for periods of up to seven days. Individual sensors are each calibrated to ±0.01° C. at the time of manufacture of data-logger 314, by adjusting the calibration resistance. This high level of accuracy, which is not found in the prior art, is essential in this apparatus in order to fulfill the purpose of breast thermometry testing in the context of breast cancer risk and breast cancer. Each of the sensors is polled in rapid sequence, using analog multiplexers type DG404 (Intersil Corporation, Fla., USA). Each of the sensor readings is fed into an operational amplifier, which conditions the signal so that it can be processed. This is achieved by converting the analog signal into a digital one using a 12 bit analog to digital converter. Once in digital form, the data from a set of readings are stored in 4 Mb non-volatile flash memory (Advanced Micro Devices, Calif., USA) until the microprocessor is instructed to upload data to host PC 316. The operations of writing and addressing, the duration of the readings, as well as the time between readings, are all controlled by the microprocessor. Data-logger 314, is powered using two rechargeable batteries of the type known as 'AAA'. Separate voltage levels are used for the analog and digital parts of the circuit in order to reduce interference and these are controlled using regulator chips to maintain correct values. Separate control amplifiers are provided in data-logger 314, to monitor outputs from an ambient temperature sensor 730, mounted sub-flush on the outer upper surface 732, of case 722, of data-logger 314, and also from an additional sensor 734, which is used to measure a non-breast body surface reference temperature, typically at a distant point such as over the trapezius muscle of a test subject. Reference temperature sensor 734, is attached to data-logger 314, by a flying lead 736 and is provided with subject mounting means in the form of a soft fabrics patch 738, which may be secured in place on a subject with low-adhesion surgical tape (not shown).

Data-logger 314, is provided with display means in the form of LEDs 740, 742 and 744, which, when lit indicate 'power on', 'test running' and 'low battery status', respectively. Further display means are conveniently in the form of a multi-line, multi character LCD 746. LCD 746, indicates electrical status of data-logger 314 and harness 312, under a variety of conditions and also shows test-critical and test subject security data, including unique subject identifiers, hereinafter described. Push button switches 748, 750 and 752, are clearly marked and control 'power on/off', 'function display' and 'test initiation', respectively. Provided that data-logger 314, has been brought to readiness according to a carefully controlled protocol, hereinafter described, a temperature sensing cycle is initiated by pressing 752. Data-logger 314, switches off automatically at the end of a sensing cycle.

Interaction between data-logger 314 and host PC 316, is managed with serial interface means integral with host PC 316 and in the form of an internal PC card which includes a single upload/download data port, indicated at 318. Interface means 318, also provides automatic battery charging service means in the form of multiple charging ports indicated by way of example at 754, for any data-logger or series of data-loggers attached to it.

At an appropriate time, stored data within the non-volatile flash memory of data-logger 314, are uploaded to host PC 316, via upload/download data port, indicated at 318. After uploading data from any particular subject test to PC 316 and until the download of security data from the PC to data-logger 314, for the next test, LCD display 746, will show the subject name and test number from the last performed test. Other information can be read from LCD display 746, by toggling 'function display' button 750 and by noting the condition of LEDs 740, 742 and 744.

Host PC 316, includes an entry level, or better, motherboard and microprocessor, preferably an Intel™ Pentium™ III type, or better, and the operating system is preferably a limited, partial installation of Microsoft™ Windows 98™. Host PC 316, is also provided with a dedicated software program written in Visual Basic™. Commands which control the outflow of data to host PC 316, are set from the keyboard 324 and mouse 320, of host PC 316, and sent to the microprocessor of data-logger 314, via upload/download data port 318. Data are date-stamped using an internal real time clock (RTC) within data-logger 314. System variables, such as test period and time between sensor readings, are set and downloaded in a similar manner and new values are stored in the non-volatile flash memory of data-logger 314, for controlling subsequent test parameters. PC software is protected by a hardware security device well known to those skilled in the computer art as a 'dongle' (not shown) which, if not connected to PC 316, will prevent all operational access. The 'dongle' may, optionally, incorporate means for integrating a credit system for levying a monetary charge for each test.

In improved system 310, access to the dedicated software program is subject to multi-level password access and also time-out control. Thus any operator, whether one authorized to manage a data-logger 314, for testing on a subject, or one authorized to use PC 316, for the inputting of data, or an engineer or other person authorized to change system variables, will be required to prove such authorization in order for system 310, and in particular the dedicated software program, to function. Access is obtained by first logging a unique password, and then other suitable unique identifier details, such as name, status and, if applicable, employee number, to a designated field displayed on an opening screen on VDU 322, of PC 316. Access will time-out at a predetermined time at the end of each work day unless temporarily defeated by a task in progress, following the completion of which, access time out will prevail so that if continued access is required it will be necessary for operators to log on once more, thus ensuring that any out-of-hours access is logged to system 310. Time out occurs, in any event, at midnight each day.

The dedicated software program provides improved screen data displays and these range from the simple numerical display of temperature data in spreadsheet style to elaborated graphics. All displays follow an informal international standard used by surgeons to reference landmarks on the human breast. This involves representation of the breast from a 'within-subject' viewpoint and then addressing first the upper outer quadrant and proceeding clockwise to the upper inner quadrant.

A first spreadsheet-style display presents ambient, body reference and breast sensor temperature readings in columns and also shows each polling interval during the data collection period. A second spreadsheet style display presents ambient and body reference temperatures and then displays breast sensor data as variances from the body reference temperature at each polling interval during the data collection period. In the first display, temperatures which are in excess of specified variance tolerance limits from expected temperatures are automatically highlighted and in the second display variances which exceed specified tolerance limits from expected values are automatically highlighted. In both cases, these data may be scrolled in any desired direction and a column heading and row frame is provided to facilitate comparison across a row. Both these data subsets may be toggled between the spreadsheet style and a conventional multi-line graphical display.

A third spreadsheet style display is a summary of the average readings, for each of the breast sensors, throughout the entire data collection period, together with the average, for each of the breast sensors, of variances from the body reference temperature. Out of tolerance anomalies are excluded, but an absolute count of anomalous readings, and that number expressed as a percentage of all readings, may be displayed for each breast sensor.

As may be seen by reference to FIG. 27, which is unnumbered, a dedicated graphical representation is in the form of masks each comprising a modified ovoid locus having a tendency to be pear-shaped to mimic the breast sensor layout patterns on each breast with the left breast to right of screen and right breast to left of screen. Sensor positions are represented in their correct spatial disposition on the locus as circles of sufficient size to allow numerical data appearing within them to be easily readable. Data displayed includes the numerical temperature reading for each sensor and also its variance from the body reference temperature, expressed numerically, but also in a graded color, from blue through to red, to indicate an increasing magnitude of variance from body reference temperature. Excess variances may be automatically highlighted by means, for instance, of reverse video on those pixels carrying such a signal. This graphic display may be scrolled through successive polling data subsets. An on-screen telltale box indicates time from start of test of each subset viewed. All data subsets and their screen display groupings from a given subject record are retrievable from a database using a suitable query and may be used for statistical analysis and comparison.

Preferred Method of Use of New and Most Preferred Embodiment

Since the disclosure of the original embodiment of the instant invention, we have gained a much fuller appreciation of the importance of providing women with better and earlier information on their breast health status. Much of this information has been gathered from extended conversations with oncologists, breast surgeons, breast cancer nurses, counselors specializing in the field and breast cancer sufferers themselves and their relatives. Some of what was learned has been referred to and incorporated hereinbefore, such as the view that the interface means between the test subject and any test system must be acceptable to women and routine service providers alike and that accurate information is also a mandatory requirement. To amplify this lafter point, poor or inaccurate information is, in some ways, more dangerous than no information at all, since treatment strategies, including surgery—mastectomy—may depend on the results of instrumented physiological testing.

Furthermore, we have encountered press reports of occasional, but disastrous, examples of patient records which have become mixed up, leading to one patient undergoing inappropriate surgery and another not being diagnosed with a life threatening disease. For example, in one case a woman was told she had breast cancer when, in fact, this was not so. She opted for prophylactic mastectomy of the second 'unaffected' breast. It is not known whether, in this example, the other patient, declared healthy but who actually had breast cancer, died from the disease later or not. Other examples of mishandling of records have included transposition of left and right breast data leading to mastectomy of an unaffected breast, leaving a diseased breast, initially at least, intact.

We have also learned that, if an accurate and absolutely secure system of providing meaningful information on breast health were available, it would be of great value not only in determining the presence or absence of breast cancer and in determining the risk in women who do not currently have the disease of subsequently developing it, there would also be a number of other important applications. These would include, non-exhaustively, the following:

1. Investigating and monitoring any thermometric response that there may be to positive dietary intervention or other non-surgical intervention strategies in women already diagnosed as being at risk of developing breast cancer, whether the high risk status of such women was been determined by thermometric means, by investigation of their genetic status, or other means;

2. Subject to suitable trials, improving the quality of counseling to women considering prophylactic mastectomy of a second and apparently unaffected breast. Mammography as a check technique is limited because of radiation concerns and also magnetic resonance imaging is limited because many women do not find it tolerable;

3. Accurate thermometric assessment could be useful in optimizing the time of surgery and for assessing surgical outcomes in very large tumors, where drugs are used to shrink the tumor to aid and facilitate surgery.

These additional and extended uses for the apparatus of the instant invention provide good arguments to support the use of a greater number of sensors in each breast sensor array. More fundamental, however, is that the instant invention is concerned, primarily, with the assessment of risk in subjects who appear to be generally healthy, of developing breast cancer later in life. In this group, the aim is to collect temperature data generated by a general physiological response to the tidal hormonal flow throughout the menstrual cycle at a particular point in that cycle. On the face of it, therefore, there is no need to collect data from any specific point or points on the breast nor to be concerned by the absence of data from a small number of specific points. However, breast cancer is highly prevalent in the subject population and it is not possible to tell, in advance, whether any given subject, presenting for routine risk assessment, may actually be harboring breast cancer. In mass applications of the instant invention, this scenario will not infrequently be encountered and there is an implicit duty of care upon any service provider to collect not only general indicative data but also, so far as reasonably possible, more specific data which may help to localize a lesion, if present.

The preferred method of use of the new and improved harness and the applicability of the significantly enhanced performance and security measures in the cooperation between the data-logger and the host of the new and most preferred embodiment, will always be the same, regardless of the application. The preferred method of use in the primary application of breast cancer risk assessment in women who do not, so far as is known, currently have the disease, is also, in general, similar to that employed with the original embodiment. In the extended applications, where breast cancer is already known to be present, the use of serial progesterone assays may or may not be used to determine a specific test day.

The primary intended application for system 310, is in screening women between twenty and fifty years of age and who have not reached the menopause, to detect whether or not they may be at risk of developing breast cancer at some future date. System 310, is so designed that it may be readily used for mass screening in large populations of women, has a relatively short attendance period at a test location and involves the accurate measurement of a plurality of breast surface temperatures.

Reliable epidemiological data exist on the incidence of breast cancer which suggest that as many as one in twelve women in Europe and perhaps one in ten women in the USA, dies from breast cancer, it is inevitable that in any large scale screening program, numerous subjects will be tested who actually have the disease. Since it is also now known that breast surface temperature data, collected accurately at the appropriate point in the menstrual cycle, using progesterone assay to determine that point, are substantially similar in both the at-risk-but-with-no-disease-currently-present group and the active-disease group and further, that those data are different from the not-at-significant-risk group, the instant system 310, has potential for secondary use in confirmation of the presence of active disease.

The preferred method of use of the instant system 310, in the primary application, involves the subject to be investigated first being counseled, upon recruitment, as to the nature of the test. At least one month prior to the test, she is provided with a home-use urine dip test kit and a saliva collection kit. The urine dip test kit is in the form of a series of paper strips impregnated with a suitable agent which reacts to the surge of luteinizing hormone in the urine which occurs at ovulation, by a color change from green to yellow. Such a test may be obtained commercially under the name Unipath™. The method of use of this test kit and a salivary progesterone assay is substantially as described in relation to the original embodiment.

Based on the results of the salivary progesterone assays from the laboratory, the investigator or investigating group selects the appropriate day for the subject to attend a test location and invites her to do so. In a subject with a normal twenty-eight day cycle this will normally be day seventeen of the next cycle; in women with differing cycles it will normally be the 'day seventeen equivalent'.

At any test location, on any test day, whether tests are to be carried out for the primary application or for an extended application of the new and improved embodiment of the improved instant system 310, all authorized operators must log on to improved system 310, by entering passwords and identifier details. Furthermore, access will time-out at a pre-determined time at the end of each work day unless temporarily defeated by a task in progress, following the completion of which, access time out will prevail so that if continued access is required it will be necessary for operators to log on once more, thus ensuring that any out-of-hours access is logged to system 310. Time out occurs, in any event, at midnight each day.

The authorized operator of host PC 316, is required, prior to any test, to input a minimum number of mandatory entries, concerning the subject, to a new 'Subject Record' which is a file in a database. The 'Subject Record' file itself has a unique alpha numeric identifier which is automatically generated on the basis of an incremental sequence. The mandatory fields which must be entered into a 'Subject Record' include subject surname, subject forenames; subject address, including zip or postal code, date of birth and social security number (in the USA) or equivalent (such as National Insurance Number in the U.K.). Upon completion of entry of mandatory data, an automatic search of the database is carried out, according to defined criteria, which ensure that any similar 'Subject Record', such as that of a family member or relating to a previous test on the same subject, is brought to the attention of the operator. 'Subject Records' in the database, which is advantageously searchable, additionally provide fields for general practitioner name and office address, specialists' names, office addresses and hospital affiliations, drug or other clinical trial participation, progesterone assay and other pathology test details, if any, and text notes. A higher level of access, also by password, is provided for reprogramming test parameters, such as sensor polling interval and test duration, and this would be restricted to either a specially trained and authorized person at a test center or a peripatetic system engineer.

When the requisite minimum mandatory entries to the 'Subject Record' have been entered, host PC 316, is capable of allowing the provision of signals to data-logger 314, connected to data port 318, to render it ready for use. However, this will not be permitted unless host PC 316, recognizes the unique identifiers of the operator associated with data-logger 314. If the data-logger operator is also the PC operator, it is necessary that this information is input at the outset and it is required to be reconfirmed before PC 316, will allow data-logger 314, to be readied for use.

Once the security protocol has been satisfied, PC 316, interrogates data-logger 314, connected to data port 318, to ensure that it does not hold data, and also that its battery status is adequate to provide power for up to three hours before a test is started, for the duration of a test which is to be performed and for a reasonable period following the test for it to be brought back to PC 316. It is necessary for connected data-logger 314, to have 'Power On' status and this is indicated by illuminated LED 740. Provided that data-logger 314, is void of data and the battery power reserve is adequate, PC 316, automatically generates a unique, incrementally sequenced 'Test Number', associated irrevocably with the new 'Subject Record' and downloads this to data-logger 314, together with the subject surname and first name, all of which appear on data-logger LCD display 746, and remain displayed thereon until any subsequent upload of data from data-logger 314, to PC 316. Data-logger LCD 746, also displays the message 'Ready To Run'. If a test is not initiated by the end of three hours, measured by the on board RTC of data-logger 314, it will time out and cannot be used until it is reconnected to PC data port 318, and readied once more.

It will have been noted that not in all applications of the improved system 310, will the test be carried out on a day pre-determined by progesterone assays, however, the dedicated program of host PC 316, will, by default, provide prompt means requesting progesterone assay results and for initiating a progesterone assay ordering and control sequence. If progesterone assays are not to be done in a particular case this will require the prompt to be defeated by a suitable input. Where improved system 310, is generally used for tests which do not require progesterone assays, a suitably authorized person may alter the appropriate system variables to switch off the associated prompts.

Data-logger 314, now in 'Ready To Run' condition, together with its associated and permanently connected harness 312, is taken to the test environment, preferably a dedicated room, where the ambient temperature should be maintained at 22° C.±2° C. A female helper or nurse, who is also operator of data-logger 314, and must be logged on to host PC 316, provides the subject with privacy and requests her to doff her upper garments. The subject is asked to confirm her first name and surname verbally and is then asked to check the spelling of both names by inspection of data-logger LCD display 746. In the event of any discrepancy, data-logger 314, must not be used until the error has been corrected and this will involve temporarily postponing the test, returning data-logger 314, to host PC 316, reconnecting it to data port 318, aborting its status, abandoning the incorrect 'Subject Record' and 'Test Number', and generating new ones in order to return data-logger 314, to readiness. If the subject identity confirmation procedure is not followed, and more than one subject is present at the test location, the entire security of the system could be compromised.

With the assistance of the helper operator, the subject is fitted with the apparatus. First data-logger 314, which is lightweight, is suspended from the neck of the subject on light adjustable strap 724, by closing quick release buckle 726, and adjusted so that it rests in a position of comfort on the upper chest of the subject just above the breasts. Next, with the two flexible contactor pad leads 350; 352, from the left and right breasts extending upwards towards the neck area and towards data-logger 314, flexible annular frustum breast accommodating structures 500; 510, are adjusted, by sliding them on transverse anterior straps 588; 590, to positions where they will each fit, one on each breast. This is done in such a manner that the nipple, areolar area and a further portion of each of the left and right breasts passes through flexible annular frustum breast accommodating structures 500; 510, respectively, until contactor pads 328; 330, are pressed into gentle and intimate contact with each breast surface. Harness 312, is then secured in place with buckle elements 578 and 586, on posterior adjustable straps 574 and 582. Further careful sliding of breast accommodating structures 500; 510, on transverse anterior straps 588; 590, is used to finely adjust the positions on the breasts until each contactor pad 328; 330, is located concentrically about a nipple. Anterior transverse straps 588; 590 and single vertical strap 600, are then finally adjusted so that, when under moderate tension, they cause primary tabs 358–368; 386 and 370–380; 388, of contactor pads 328; 330, to be splayed into gentle compressive contact with the surfaces of the breasts.

It should be noted that, as with harness 12, of the original embodiment, the subject may wear her own brassiere, or a sports type elasticated brassiere, or no brassiere according to her wishes and the professional guidance of the operator helper. It is important that the subject wears a substantial and reasonably close fitting over-garment, to limit or prevent any generalized heat loss. This is donned, with the assistance of the operator helper, once the harness position has been finalized. Data-logger 314, with a length of contactor pad leads 350; 352, is guided out through the neck of the over-garment to be placed on the upper chest outside it. Contactor pad leads 350; 352, are folded to facilitate this procedure. The flying lead 736, of body reference temperature sensor 734, is led over one shoulder, inserted under the rear neck of the over-garment and mounting patch 738, is secured over the trapezius muscle with a piece of low adhesion surgical tape.

The subject is then seated comfortably in the test room and this should provide as welcoming and stress-free an environment as possible. It is helpful to provide the subject with reading materials and she may wish to be provided with a lightweight dressing gown for ordinary comfort. It is preferable that no drinks are taken by the subject during a test period and that the subject is encouraged to sit quietly and avoid exertion.

When ready, the operator helper depresses the push button 'Test Initiation' switch 752, on data-logger 314, to initiate the test cycle. LCD display 746, on data-logger 314, changes to display the message 'Test Running' and provides a clock display showing the minutes of the test period remaining. LED 742, is also illuminated whilst the test is in progress. Subject data collection commences, automatically, thirty minutes after initiation of the test cycle, in order to provide an adequate period for temperature equilibration to occur between the subject and contactor pads 328; 330, of harness 312. Preferred sensor polling intervals are typically between five and sixty seconds. Throughout the entire duration of each test, data-logger 314, monitors sensor 730, mounted on data-logger case 722, and displays the ambient temperature on LCD display 746. Since data-logger 314, is worn outside the over-garment, this provides means for the operator helper to check ambient temperature in the test room easily from time to time. At the end of a test period, data-logger 314, stops sensor polling and, LCD 746, displays the message 'Test Finished—Upload Data' and 'Test Running' LED 742, goes out.

Upon completion of the test, the subject may return to the private area to doff the over-garment and harness 312 and to dress in her normal clothing prior to departure from the test location. Data-logger 314, including permanently attached harness 312, is then taken back to host PC 316, by the operator helper where it is connected both to charging port 754 and to data-port 318. This action causes LCD display 746, on data-logger 314, to display a 'Charging Battery' message. Immediately upon connecting data-logger 314, to data port 318, of host PC 316, a diagnostic test is run on the integrity of the data connection. Provided that the integrity of the connection is passed as satisfactory, host PC 316, then automatically interrogates data-logger 314, first to establish the identity of the unique 'Test Number' which it provided to data-logger 314, earlier. Host PC 316, uses the unique 'Test Number' to identify the unique 'Subject Record' and having done this, opens the associated file and automatically uploads the test data from data-logger 314. Once uploading is complete, host PC 316, automatically erases and clears t he non-volatile memory of data-logger 314, and confirms that this has been done with a screen message. Data-logger 314, may now be readied once more, or it may be disconnected from data port 318 and left connected to charging port 754, to recharge, or it may be totally disconnected and stored until next required.

It should be noted that if a test is curtailed or aborted for any reason, which could include subject non-compliance or data-logger 314, being powered down (which would not lead to data loss), the upload procedure must still be followed in order to clear the memory and this must be done before a return to ready status for another test will be all owed by host PC 316. The dedicated program will file any incomplete or irrational data set but will flag both the file and any data subsequently displayed from it. It is not possible to initiate a second test run on data-logger 314, which already contains any data from a first run, whether the first run was completed or not.

The sturcture, design and sizing of contactor pads 328; 330, and of harness 312, in general, are such that, not only is a good fit obtained on both large and small breasts with large and small areolar areas, excellent and improved contact is also maintained between sensors 616–626; 640, and 628–638; 642 and both the superior and inferior aspects of the breast surfaces due to novel primary tabs 358–368; 386 and 370–380; 388, being splayed against them. Because breast accommodating structures 500; 510, of contactor pads 328; 330, are softer, more conformable and have improved architecture over those of the original embodiment they adapt particularly well to breast curvature, even on the concave upper aspect. This is in marked contradistinction to many prior art devices which are generally somewhat rigid and have a consequent tendency to 'tent' over the upper aspect, often holding functional surfaces away from the breast surface. Even though the sensor cans of the original embodiment were barely perceptible to most subjects, the cylindrical cans of the sensors used in the new and most preferred embodiment have been demonstrated, during comparative tests under confidentiality arrangements on a number of subjects, to be strongly preferred, though it is not possible to say to what extent the presence and splaying compressive function of novel primary tabs influenced this conclusion. Subject test data is evaluated by a person suitably skilled and trained to make comparisons with known norms of breast surface and body reference temperatures with a view to interpretation and reaching conclusions concerning the breast status of subjects. Any of the spreadsheet style screen displays, or their graphical alternates or the dedicated special graphical display may be selected according to choice. The comparisons, interpretations and conclusions may all vary according to the specific purpose for which the collected data is intended to be used. Evaluation notes may be saved in a 'Subject Record' in text form and may be output to hard copy as a 'Test Results Summary'. As with other persons who need to access any part of the dedicated program of host PC 316, the trained person carrying out the evaluation of data must necessarily enter a unique password and other suitable identifier details such as name, status and, if applicable, employee number to host PC 316, in order to achieve access at a level which will allow opening of 'Subject Records', viewing and manipulation of data and the making of text entries to records. Collected data may not be changed and any attempt to do so registers on host PC 316, as a system violation.

In the event that the interpretation of the data is that the subject requires further investigation, treatment or other follow up, she would normally be informed promptly, possibly on the day the test is carried out and interpreted, especially when strategies clearly need to be implemented on an urgent basis. Further investigation may well involve an early retest with the instant system as well as other tests with a view to establishing whether or not she may have existing cancer, or the extent of existing cancer, or the optimal time for surgery for cancer. It is statistically likely that if the instant test is deployed on any significant scale for the assessment of breast cancer risk, the subject population will include some women who have the undiagnosed condition. If a subject is deemed as at high risk, as interpreted from data collected with the instant test, but negative to other tests for actual cancer, she may be informed and counseled that she may develop breast cancer subsequently. This knowledge, far from being a prophecy of doom, allows surveillance, prevention and future intervention strategies to be planned and implemented. These factors, in turn, improve the chances of preventing the disease or, should it prevail, successfully treating it at an early stage. Handled well at counseling, it is eminently possible to engender a strongly positive psychological response in the subject.

Alternatively, if the subject has already had other tests which suggest that she may have breast cancer or has physical signs which suggest breast cancer, the results from tests using the instant system 310, may be used to confirm or deny previous findings.

Even when test results indicate no cause for significant concern, this information is desirably communicated to subjects as quickly as possible in order to alleviate or prevent any unnecessary stress. However, since such subjects are sometimes reassured, even to the point of euphoria, it is incumbent upon those who give this news to communicate to subjects that it is very much in their own interests to be retested at a suitable interval which may be, say, two years. In any case, the dedicated program of host PC 316, incorporates an automatic review and call-back routine by default with interval period parameters constituting one of the system variables.

From the foregoing, it will now be apparent that the new and improved embodiment of the present invention provides a system capable of making accurate measurements of temperatures on the surface of the human breast that is clearly differentiated from the prior art by its structure. The new and improved embodiment not only incorporates improved means for the collection, recordal and storage of these measurement data but also incorporates improved means for their effective manipulation and display. Additionally, the new and improved embodiment incorporates stringent password and personal identifier security measures constituting improved means for ensuring the integrity of collected data, subject security and traceability of those responsible for collection and management of data in a potentially life-critical mass screening test.

Further, that use of the instant system, according to the method hereinbefore disclosed, constitutes a method not only for the assessment of the risk of future development of breast cancer in women who do not currently have the disease and for the detection of breast cancer in women who may have the disease but also for monitoring responses to dietary and other intervention strategies for high risk women, improving the quality of counseling to those considering prophylactic mastectomy and optimizing the time of surgery in very large tumors.

It will be apparent to those skilled in the art that numerous modifications or changes may be made without departing from the spirit or the scope of either the present invention or its method of use. Thus the invention is only limited by the following claims.

What is claimed is:

1. An apparatus for measurement of temperatures on the surface of human breasts, wherein is provided a system comprising harness means provided with temperature sensing means in the form of substantially similar first and second arrays each having a plurality of sensors and having connection means extending between each of said sensor means and attached data-logging means selectively connectable to interface means interfacing with host computer means wherein;

said harness means are in the form of a harness including first and second flexible annular frustum breast accommodating structures, variably disposable apart at a rational distance so as to provide one for each breast and so sized and constructed that the frustum has a diameter selected so as to accommodate that portion of the breasts of a majority of human females extending over the nipple and to or beyond the areolar area of said breasts when said breasts are respectively located concentrically within said frustum in each of said first and second flexible annular frustum breast accommodating structures and;

said harness further including body strap means providing releasable securing means for securing said harness to a majority of human subjects and;

said connection means comprising first and second flexible printed circuits each extending uninterrupted between said first and second flexible annular frustum breast accommodating structures and said attached data-logging means and having a plurality of conducting means in the form of insulated conducting tracks, each of said conducting tracks from said first printed circuit extending from each of said sensor means forming said first array to said data-logging means and each of said conducting tracks from said second printed circuit extending from each of said sensor means forming said second array to said data-logging means and;

said data-logging means comprising a data logger having housing means in the form of a case provided with temperature monitoring cycle initiating means, power supply means for electronics means for selectively polling each of said sensor means of each of said first and second arrays at rational intervals in order to collect output data therefrom, means for monitoring ambient temperature and a body surface reference temperature, display means and means for storing said data and uploading said data via said interface means to said host computer means and;

said interface means comprising an interface between said data-logger means and said host computer means and;

said host computer means comprising a computer and dedicated software program for the management of security, receival, manipulation, elaboration and display of said data uploaded from said data-logging means.

2. The apparatus of claim 1, wherein each of said sensors of said first and second arrays of sensors is disposed upon one of a plurality of flexible and splayable tabs, said splayable tabs being disposed apart on the inner and outer margins of an inner or breast-facing contact surface of said first and second flexible annular frustum breast accommodating structures and arranged such that no hindrance or barrier to thermal transfer is interposed between said sensors and said human breast surfaces said splayable tabs of first and second flexible annular frustum breast accommodating structures being so constructed as to inherently provide means for preventing heat loss from all surfaces of said sensors not in contact with said human breast surfaces.

3. The apparatus of claim 1, wherein said harness may be used without a brassiere.

4. The apparatus of claim 1, wherein said harness may be used with a brassiere.

5. The apparatus of claim 1, wherein said first and second flexible annular frustum breast accommodating structures and said first and second flexible printed circuits constituting connection means to said data-logger are all provided with cleanable flexible covering means.

6. The apparatus of claim 1, wherein body strap means are in the form of elasticated first upper and second lower anterior straps mutually attached at respective first and second ends to form first and second 'V' configurations and elasticated first and second posterior straps provided at respective first ends with first and second elements respectively of quick release buckle means and joined at respective second ends to said first and second 'V' configurations formed by said mutual attachments of said first and second ends of said first upper and second lower anterior straps said first upper anterior strap being further provided substantially secured at right angles at its mid point with a further strap for adjusting tension between said first upper anterior strap and said lower anterior strap.

7. The apparatus of claims 1 and 5, wherein said first and second flexible annular frustum breast accommodating structures are adapted on their respective upper and lower outward facing aspects by the provision of releasably securable folded flap receival and closure means for the slidable releasable receival of said first upper and second lower anterior straps respectively.

8. The sensors of claim 1, wherein said sensors are of the 'temperature in—current out' type.

9. The sensors of claim 1, wherein said sensors are of the 'temperature in—voltage out' type.

10. The data-logging means of claim 1, wherein said data-logger is provided with means for individually calibrating each of said sensors.

11. The apparatus of claim 1, wherein said power supply for said remote data-logging means is provided by rechargeable battery means.

12. The apparatus of claim 1, wherein said data-logging means are provided with a plurality of switching means and indicator means including temperature monitoring cycle initiating means a liquid crystal display and a plurality of light emitting diodes.

* * * * *